US008534281B2

(12) United States Patent
Davies et al.

(10) Patent No.: US 8,534,281 B2
(45) Date of Patent: *Sep. 17, 2013

(54) MANIFOLD FOR USE IN MEDICAMENT DISPENSER

(75) Inventors: Michael Birsha Davies, Ware (GB); Mark Andrew Hailey, Ware (GB); Mark Gregory Palmer, Ware (GB); Richard Ian Walker, Ware (GB)

(73) Assignee: Glaxo Group Limited, Greenforo, Middlesex (GB)

( * ) Notice: Subject to any disclaimer, the term of this patent is extended or adjusted under 35 U.S.C. 154(b) by 973 days.

This patent is subject to a terminal disclaimer.

(21) Appl. No.: 12/096,820

(22) PCT Filed: Dec. 11, 2006

(86) PCT No.: PCT/GB2006/004612
§ 371 (c)(1), (2), (4) Date: Jun. 10, 2008

(87) PCT Pub. No.: WO2007/068896
PCT Pub. Date: Jun. 21, 2007

(65) Prior Publication Data
US 2008/0308102 A1    Dec. 18, 2008

(30) Foreign Application Priority Data

Dec. 12, 2005 (GB) .................................. 0525237.4
Nov. 23, 2006 (GB) .................................. 0623405.8

(51) Int. Cl.
*A61M 16/00* (2006.01)
(52) U.S. Cl.
USPC ..................................................... 128/203.15
(58) Field of Classification Search
USPC ............. 128/203.12, 200.24, 203.15, 203.21; 221/69, 70, 71
See application file for complete search history.

(56) References Cited

U.S. PATENT DOCUMENTS 2,587,215 A   2/1952   Priestly
3,565,071 A   2/1971   Cobb et al.
(Continued)

FOREIGN PATENT DOCUMENTS

CA    2093809 A1    2/1993
CN    1054893 A     10/1991
(Continued)

OTHER PUBLICATIONS

U.S. Appl. No. 11/722,188 filed Jun. 20, 2007.
(Continued)

*Primary Examiner* — Lynne Anderson
*Assistant Examiner* — Bradley Philips
(74) *Attorney, Agent, or Firm* — Robert J. Smith

(57) ABSTRACT

A manifold for use in a medicament dispenser device for the delivery of medicament powder from an open blister pocket of a blister pack comprises a body, the body defining a chimney having a chimney inlet and a chimney exit for directing airflow from said chimney inlet to the chimney exit; the body further defining a chamber having a chamber inlet and a chamber exit, wherein the chimney exit and the chamber inlet lie side-by-side each other such that when the open blister pocket of the blister pack is positioned adjacent thereto the airflow is directed from the chimney exit to the chamber inlet via the open blister pocket to entrain the medicament powder and enable transport thereof in the airflow from the chamber inlet to the chamber exit, and wherein one or more bleed holes are provided between the chimney and the chamber such that bleed airflow is able to be directed into the chamber to disruptively impact the airflow that transports the entrained medicament powder.

61 Claims, 28 Drawing Sheets

(56) References Cited

U.S. PATENT DOCUMENTS

Figure 1:
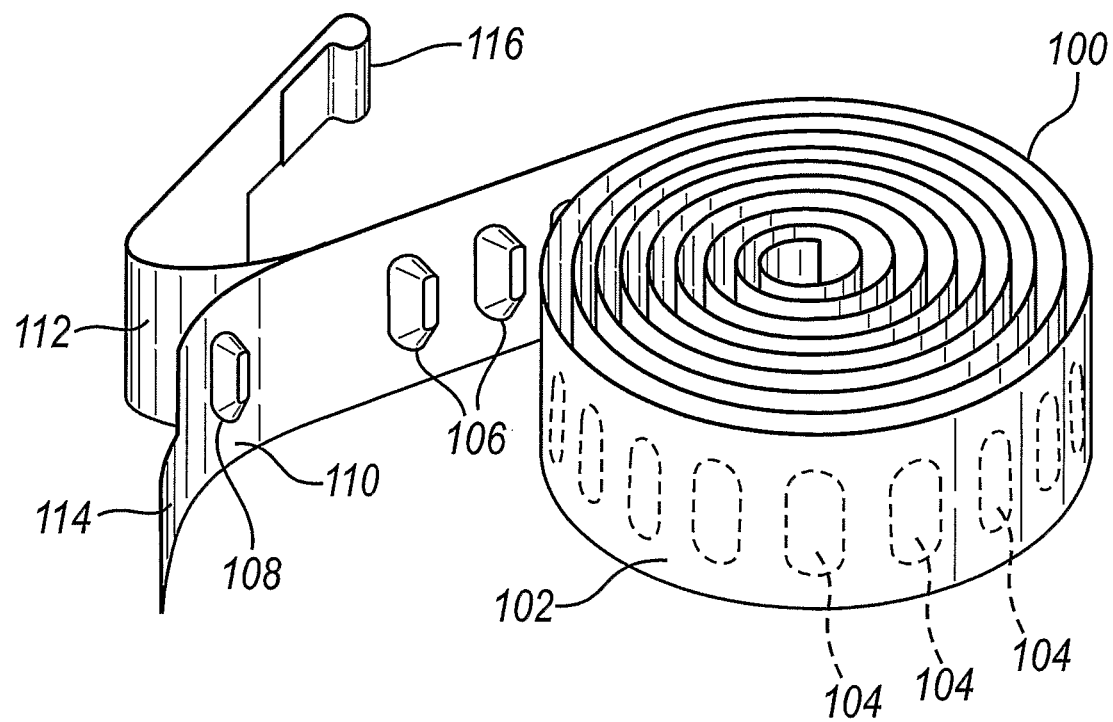

| | | | |
|---|---|---|---|
| 3,973,566 | A | 8/1976 | Mathes |
| 5,035,237 | A | 7/1991 | Newell et al. |
| 5,239,993 | A | 8/1993 | Evans |
| 5,372,128 | A | 12/1994 | Haber et al. |
| 5,469,843 | A | 11/1995 | Hodson |
| 5,492,112 | A | 2/1996 | Mecikalski et al. |
| 5,533,502 | A | 7/1996 | Piper |
| 5,590,645 | A | 1/1997 | Davies et al. |
| 5,619,985 | A | 4/1997 | Ohki et al. |
| 5,657,749 | A | 8/1997 | Cox |
| 5,694,920 | A | 12/1997 | Abrams et al. |
| 5,715,810 | A | 2/1998 | Armstrong et al. |
| 5,740,794 | A | 4/1998 | Smith et al. |
| 5,765,552 | A | 6/1998 | Zanen et al. |
| 5,881,719 | A | 3/1999 | Gottenauer et al. |
| 6,029,661 | A | 2/2000 | Whaley et al. |
| 6,065,472 | A | 5/2000 | Anderson et al. |
| 6,209,538 | B1 | 4/2001 | Casper et al. |
| 6,273,086 | B1 | 8/2001 | Ohki et al. |
| 6,615,826 | B1 | 9/2003 | Gabrio et al. |
| 6,655,381 | B2 | 12/2003 | Keane et al. |
| 6,715,485 | B1 | 4/2004 | Djupesland |
| 6,722,364 | B2 | 4/2004 | Connelly et al. |
| 6,792,945 | B2 | 9/2004 | Davies et al. |
| 6,845,772 | B2 | 1/2005 | Braithwaite et al. |
| 6,983,748 | B2 | 1/2006 | Brown et al. |
| 2001/0029948 | A1 | 10/2001 | Ingle et al. |
| 2002/0053344 | A1 | 5/2002 | Davies et al. |
| 2003/0183229 | A1 | 10/2003 | Smith et al. |
| 2004/0025875 | A1 | 2/2004 | Reber et al. |
| 2004/0168687 | A1 | 9/2004 | Asking et al. |
| 2004/0250812 | A1 | 12/2004 | Davies et al. |
| 2005/0154491 | A1 | 7/2005 | Anderson et al. |
| 2005/0268909 | A1 | 12/2005 | Bonney |
| 2006/0196504 | A1 | 9/2006 | Augustyn et al. |
| 2007/0137645 | A1 * | 6/2007 | Eason et al. ............. 128/203.15 |

FOREIGN PATENT DOCUMENTS

| | | |
|---|---|---|
| CN | 2614064 | 5/2004 |
| EP | 0711572 A2 | 5/1996 |
| EP | 0745401 A2 | 12/1996 |
| EP | 1062962 A1 | 12/1999 |
| JP | 4-507357 A | 12/1992 |
| JP | 9140794 A | 6/1997 |
| JP | 4220266 A | 2/1999 |
| JP | 2005-533581 A | 11/2005 |
| JP | 8501233 | 3/2012 |
| WO | 91/02558 A1 | 3/1991 |
| WO | 92/09322 A1 | 6/1992 |
| WO | 94/06497 | 3/1994 |
| WO | 94/08552 A2 | 4/1994 |
| WO | 97/25086 A2 | 7/1997 |
| WO | 97/40876 A2 | 11/1997 |
| WO | 99/13930 A | 3/1999 |
| WO | 99/47099 | 9/1999 |
| WO | 00/64520 A1 | 11/2000 |
| WO | 01/26720 | 4/2001 |
| WO | 02/00280 A2 | 1/2002 |
| WO | 02/24263 A2 | 3/2002 |
| WO | 02/053216 A2 | 7/2002 |
| WO | 02/089881 A1 | 11/2002 |
| WO | 03/075988 A1 | 9/2003 |
| WO | 2004/011067 A1 | 2/2004 |
| WO | 2004/093848 A2 | 11/2004 |
| WO | 2005/002654 A2 | 1/2005 |
| WO | WO 2005002654 A2 * | 1/2005 |
| WO | 2005/014089 A1 | 2/2005 |
| WO | 2005/037353 A | 4/2005 |
| WO | 2006/066908 A | 6/2006 |
| WO | 2006/066909 A1 | 6/2006 |
| WO | 2006/066910 A1 | 6/2006 |
| WO | 2007/012871 A1 | 2/2007 |

OTHER PUBLICATIONS

U.S. Appl. No. 11/722,185 filed Jun. 20, 2007.
Office Action dated Oct. 19, 2010 for U.S. Appl. No. 11/722,188.
Amendment filed Jan. 18, 2011 in response to Office Action dated Oct. 19, 2010 for U.S. Appl. No. 11/722,188.
Final Office Action dated Feb. 8, 2011 for U.S. Appl. No. 11/722,188.
Amendment After Final filed Mar. 29, 2011 in response to Final Office Action dated Feb. 8, 2011 for U.S. Appl. No. 11/722,188.
Advisory Action dated Apr. 6, 2011 in response to 37 CFR 1.312 Amendment After Final dated Mar. 29, 2011 for U.S. Appl. No. 11/722,188.
Non-Final Office Action dated Nov. 10, 2011 for U.S. Appl. No. 12/096,823.
Amendment After Non-Final filed Feb. 8, 2012 in response to Non-Final Office Action dated Nov. 11, 2011 for U.S. Appl. No. 12/096,823.
U.S. Appl. No. 12/096,823 filed Jun. 10, 2008.
Simons, F.; Antihistamines; Middleton's Allergy: Principles and Practice; 6th Edition; Chapter 51; pp. 834-863, 2003.
U.S. Appl. No. 11/722,193 filed Jun. 20, 2007.
U.S. Appl. No. 12/096,823, Final Rejection mailed Apr. 13, 2012.
U.S. Appl. No. 12/096,823, Request for Continued Examination and response to Final Rejection, dated Jul. 11, 2012.
U.S. Appl. No. 11/722,185, Examiner Initiated Interview Summary dated Mar. 21, 2013.
U.S. Appl. No. 11/722,185, Notice of Allowance and Issue Fee Due dated Mar. 21, 2013.
U.S. Appl. No. 11/722,185, Amendment after Final Office Action dated Feb. 21, 2013 entered Mar. 21, 2013.
U.S. Appl. No. 11/722,185, Advisory Action dated Feb. 6, 2013.
U.S. Appl. No. 11/722,185, Amendment after Final dated Jan. 23, 2013, entered Feb. 6, 2013.
U.S. Appl. No. 11/722,185, Final Rejection dated Nov. 23, 2012.
U.S. Appl. No. 11/722,185, Amendment dated Nov. 13, 2012.
U.S. Appl. No. 11/722,185, Non-Final Office Action dated Aug. 13, 2012.
U.S. Appl. No. 11/722,185, Amendment filed Jul. 27, 2012.
U.S. Appl. No. 11/722,185, Office Action dated May 3, 2012.
U.S. Appl. No. 12/096,823 Non Final Office Action dated May 7, 2013.

* cited by examiner

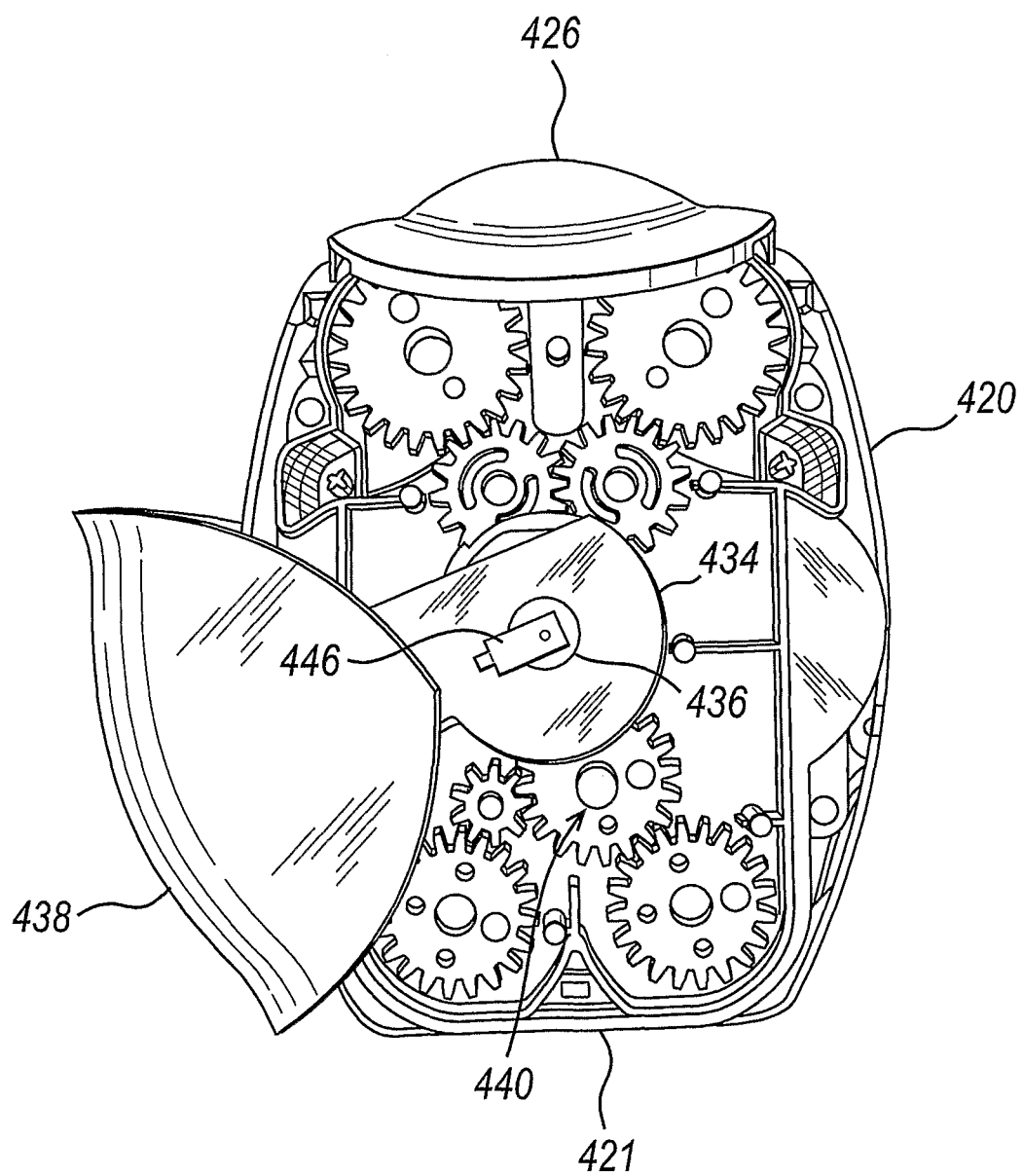

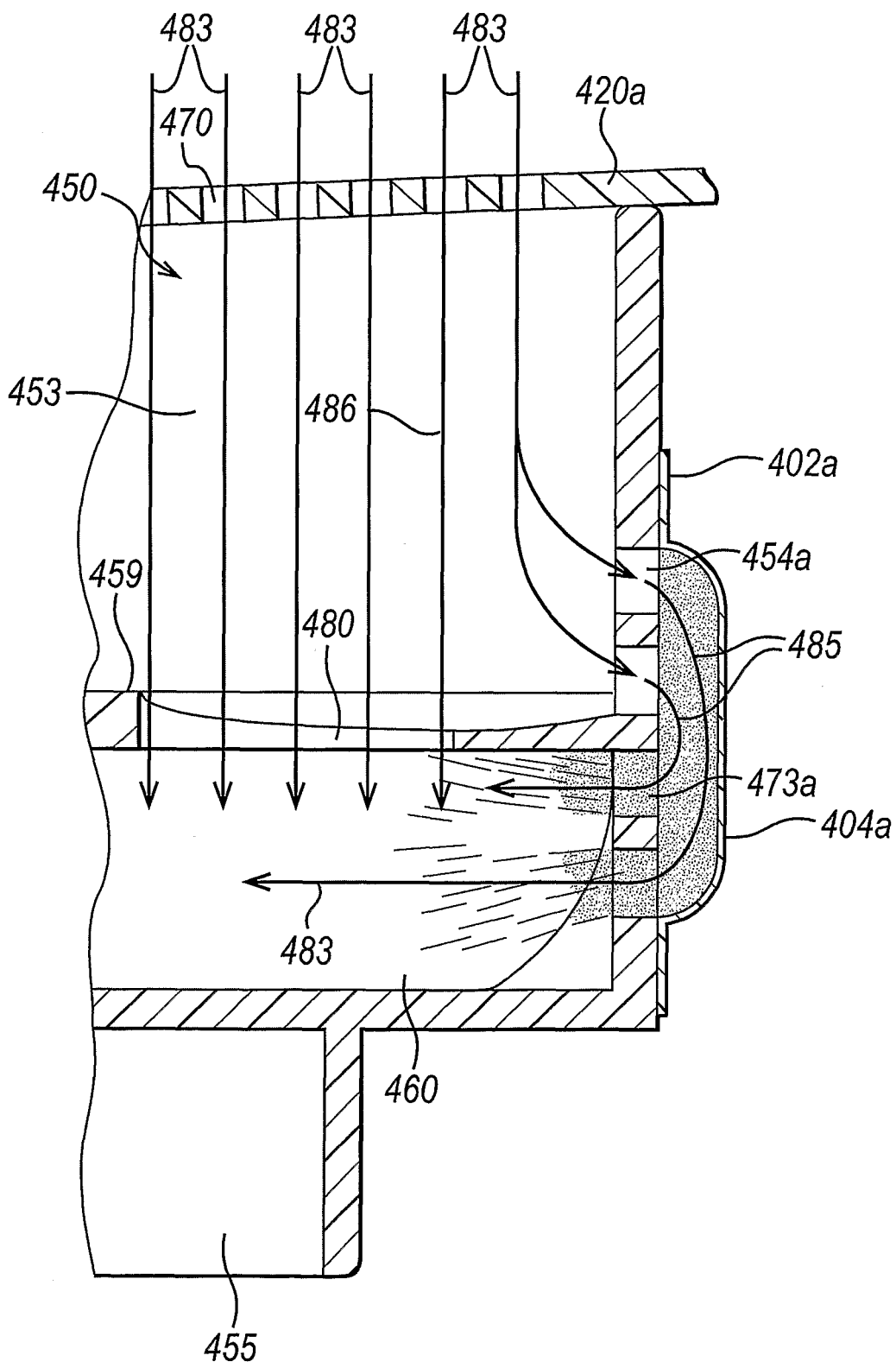

MANIFOLD FOR USE IN MEDICAMENT DISPENSER

CROSS-REFERENCE TO RELATED APPLICATIONS

This application is filed pursuant to 35 USC 371 as a United States National Phase Application of International Patent Application Serial No. PCT/GB2006/004612 filed on 11 Dec. 2006, which claims priority from UK patent application No. 0 525 237.4 filed on 12 Dec. 2005 and UK patent application No. 0 623 405.8 filed on 23 Nov. 2006, the entire contents of which are hereby incorporated herein by reference.

TECHNICAL FIELD

The present invention relates to a manifold that is suitable for use in a medicament dispenser for dispensing dry powder medicament, for example from a blister pack form medicament carrier. The manifold assists effective release of medicament powder for inhalation by a patient, for example from an opened blister pocket to a mouthpiece of the dispenser, and thence for inhalation by a patient.

BACKGROUND TO THE INVENTION

The use of inhalation devices in the administration of medicaments, for example in bronchodilation therapy is well known. Such devices generally comprise a body or housing within which a medicament carrier is located. Known inhalation devices include those in which the medicament carrier is a blister pack containing a number of blister pockets for containment of medicament in dry powder form. Such devices typically contain a mechanism for accessing a medicament dose by opening one or more blister pockets. The mechanism for example, comprises either piercing means or peeling means to peel a lid sheet away from a base sheet of the blister pack. The powdered medicament is then liberated from the opened blister pocket(s) for inhaled delivery to the patient.

Inhalation devices of the type described above comprise an element, generally referred to as a manifold, for guiding airflow towards one or more opened blister pocket(s) for liberating the powder contained therein; and subsequently guiding that liberated powder to a mouthpiece for inhalation by a patient. It is appreciated that the characteristics of the manifold are important in both ensuring effective liberation of powder and in subsequently guiding that liberated powder to the mouthpiece.

It is now appreciated that the form of the manifold can affect the particle size characteristics of the liberated medicament powder, which characteristics are known to be pharmaceutically important. In particular, it is now appreciated that fine particle fraction can be influenced by the form of the manifold. As known in the art, “fine particle fraction” or FP Fraction generally refers to the percentage of particles within a given dose of aerosolised medicament that is of “respirable” size. It is desirable that the form of the manifold acts such as to increase the FP Fraction of the liberated powder that is made available at the mouthpiece for inhalation by the patient.

It is further appreciated that manifold performance (e.g. FP fraction of dispensed medicament powder) can be influenced by the arrangement of a chamber through which the liberated medicament powder is transported (i.e. entrained within an airflow) to be made available at the mouthpiece. More particularly, it is now appreciated that it is beneficial that the chamber is arranged to promote break up (e.g. de-aggregation or de-agglomeration) of the liberated medicament powder that is transported there through.

In accordance with one aspect of the present invention, the manifold is provided with both a chimney with a chimney inlet and chimney exit; and a chamber with a chamber inlet and a chamber exit. In use, all airflow into the manifold is via the chimney inlet. The chimney exit and chamber inlet lie side-by-side each other such that when a medicament powder-containing, open blister pocket of a blister pack is positioned adjacent thereto at least a portion of that airflow can be directed from the chimney exit to the chamber inlet via the open blister pocket to entrain said medicament powder and enable transport thereof in the airflow from the chamber inlet to the chamber outlet. To promote break up of that medicament powder, one or more bleed holes are provided between the chimney and the chamber such that bleed airflow may be directed into the chamber to disruptively impact the airflow that transports the entrained medicament powder.

It may thus be appreciated that, in use, the total airflow entering the chimney of the manifold is ‘separated’ into that portion which is directed at the open blister pocket to entrain the medicament powder and that portion which is directed through the one or more bleed holes as bleed air. One advantage of the present manifold is that it may be fine tuned to determine the percentage of total airflow that constitutes each of these ‘separated’ portions and to thereby, allow for fine tuning of manifold performance.

Prior art manifolds (including those described by earlier patent publications WO98/30262, WO98/11929, WO 02/102,444, U.S. Pat. Nos. 2,587,215, 5,383,850, EP-A-1, 106,196, WO 94/08552, WO 94/11044, U.S. Pat. Nos. 5,590, 645 and 5,113,855) have been described to comprise bleed holes to a chamber or mouthpiece element. These prior art manifolds are designed, in use, to draw bleed air through an air inlet which communicates directly with the external environment (i.e. directly with the outside air).

SUMMARY OF THE INVENTION

According to one aspect of the invention there is provided a manifold for use in a medicament dispenser device for the delivery of medicament powder from an open blister pocket of a blister pack, the manifold comprising a body, said body defining a chimney having a chimney inlet and a chimney exit for directing airflow from said chimney inlet to said chimney exit;

the body further defining a chamber having a chamber inlet and a chamber exit, wherein the chimney exit and said chamber inlet lie side-by-side each other such that when said open blister pocket of said blister pack is positioned adjacent thereto said airflow may be directed from the chimney exit to the chamber inlet via the open blister pocket to entrain said medicament powder and enable transport thereof in the airflow from the chamber inlet to said chamber outlet, and wherein one or more bleed holes are provided between the chimney and the chamber such that bleed airflow may be directed into the chamber to disruptively impact the airflow that transports the entrained medicament powder.

There is provided a manifold that is suitable for use in a medicament dispenser device for the delivery of medicament powder from an open blister pocket of a blister pack.

Thus, there is also provided a medicament dispenser device suitable for the delivery of medicament powder from an open blister pocket of a blister pack, the dispenser device comprising a housing; within said housing, a dispensing mechanism for the dispensing of medicament powder from an open blister pocket of a blister pack receivable thereby; and a manifold as described herein.

The manifold comprises a body that is generally sized and shaped for receipt by a medicament dispenser device, of which it typically comprises a component part. The manifold itself may either be comprised as a single, integral component or as a sub-assembly or part of an adjacent component, and is typically formed as a moulded part.

In aspects, the manifold is either integral with or separable from the other components of the medicament dispenser device. In one aspect, the manifold is provided as a separable snap-fit component to the medicament dispenser device, and the manifold and/or medicament dispenser device is provided with snap-fit features (e.g. located on the body of the dispenser device) to enable this mode of fitting.

Suitably, the manifold is arranged for receipt by a medicament dispenser device at a location that is intermediate between a mouthpiece for the delivery of medicament in inhaled form by a patient; and an opening station, at which an opened blister pocket of the blister pack is presented to the manifold (i.e. at which its medicament contents may be accessed and entrained). Suitably, the manifold is provided with snap-fit features to enable snap-fitting thereof to the mouthpiece such as to form a snap-fitted manifold and mouthpiece sub-assembly.

The body of the manifold defines a chimney that has a chimney inlet and a chimney exit. In use, air is drawn through the chimney inlet (e.g. as a result of patient inhalation) to create airflow therein. The chimney acts to direct that airflow from the chimney inlet to the chimney exit.

The body of the manifold also defines a chamber that has a chamber inlet and a chamber exit. Air and medicament powder entrained therein (see below) may be drawn through the chamber inlet to the chamber exit. A mouthpiece generally locates adjacent to the chamber exit. In one particular aspect, that part of the body defining the chamber exit and the mouthpiece comprise a common component.

The chimney exit and chamber inlet lie side-by-side (i.e. adjacent or close to) each other such that when said open blister pocket of said blister pack is positioned adjacent thereto the airflow may be directed from the chimney exit to the chamber inlet via the open blister pocket to entrain the medicament powder contents thereof.

Transport of the so-entrained medicament particles is thereby enabled in the airflow from the chamber inlet to the chamber outlet.

The manifold may define more than one chimney exit and chamber inlet and typically would do so where the manifold is designed for use with a medicament dispenser device for dispensing of medicament from more than one open blister pocket at a time. Typically, one chimney exit and one chamber inlet lying side-by-side will be provided to dispense powder from each open blister pocket.

In one aspect, the manifold herein is suitable for use in a medicament dispenser device for the delivery of medicament powder from an open blister pocket of each of plural blister packs, the manifold comprising plural pairings of chimney exit and chamber inlet, each said pairing associated with an open blister pocket of one of said plural blister packs. Thus, for example in a preferred medicament dispenser device herein arranged to dispense powder from a pair of opened blister pockets, each one of the pair associated with a single elongate strip form blister pack, the manifold will be provided with a pair of chimney exits and associated chamber inlets, each lying side-by-side each other.

In aspects, the manifold geometry is arranged such that only a proportion of the total airflow entering the manifold through the chimney inlet is directed via the chimney exit towards the open blister pocket. Suitably, from 3 to 50%, preferably from 5 to 25%, more preferably from 15 to 25% of the total airflow (e.g. about 20%) is directed via the chimney exit towards the open blister pocket and thence, via the chamber inlet into the chamber. That is to say, from 97 to 50%, preferably from 95 to 75%, more preferably from 85 to 75% (e.g. about 80%) of the total airflow is directed through the one or more bleed holes into the chamber.

In an embodiment of the invention, where the manifold is for use with two blister packs, such as those hereinafter described with reference to the accompanying Figures, in use 80% or approximately 80% of the total airflow entering the manifold chimney (through the chimney inlet) passes though the bleed hole(s), the balance passing though the opened pockets.

The manifold herein is suitable for use in a medicament dispenser device in which the patient breathes in to create the airflow and bleed airflow through the manifold. The manifold and medicament dispenser device herein is designed to be suitable for use by a patient (e.g. asthmatic) with relatively poor breathing ability. A typical asthmatic patient might achieve a flow rate of around 30 to 100 liters/min through a medicament dispenser device.

Typically, the manifold provides an airflow resistance of 1 to 5 kPa (e.g. 2-3 kPa) for a typical airflow entering the chimney of 60 liters/minute, at which flow rate around 10% of the airflow is directed through the open pocket. The airflow entering the chimney may also vary, typically being from 30 to 100 liters/minute.

It will be appreciated that in use, the pressure drop and flow rate achievable by a patient depends upon both the level of airflow resistance of the manifold and/or medicament dispenser device and the breathing ability (respiratory effort) of the patient. As will be appreciated from the later description, the one or more bleed holes provided thereto may in particular, be used to control the overall airflow resistance of the manifold.

The airflow resistivity of a particular manifold and/or medicament dispenser device can be found by dividing the square root of the pressure drop (in kPa) by the flow rate (in liters/min). Low airflow resistivity of the manifold and/or medicament dispenser device is generally preferable because it enables the patient to take a deep breath and thereby transport the medicament particles (as delivered from the dispenser device) to the lung.

It will be appreciated that the exact orientation of the chimney exit and chamber inlet will be determined to an extent by the shape of the blister pocket, and the desired function of entrainment of medicament powder particles in the airflow directed into the pocket. In one aspect, the open blister pocket has a generally elongate oval profile and the chimney exit and chamber inlet lie side-by-side and in use, are positioned above opposite ends of the elongate oval open pocket profile.

It will also be appreciated that the shape and dimensions of the chimney exit and chamber inlet will be determined to an extent by the shape of the blister pocket, and the desired function of entrainment of medicament particles in the airflow through the pocket. It has been found that reducing the cross-sectional area of chimney exit and chamber inlet can improve FP fraction performance at the expense of increased airflow resistance and potentially a reduction in pocket emptying performance. In one aspect, the chimney exit and chamber inlet define an essentially circular profile and have a diameter of from 1-7 mm, particularly 2-5 mm. Other profile shapes for the chimney exit and chamber inlet are also envisaged including ovular, rectangular, rectangular with rounded edges and crescent-shaped.

Suitably, the chimney of the manifold herein is arranged to create turbulence in the airflow at the open blister pocket. That is to say, the chimney is arranged such that in use, turbulent airflow is presented at the open blister pocket. Such turbulent airflow has been found to assist in the entrainment of the medicament powder contents of the open blister pocket, and thereby to assist in emptying of the pocket of its medicament powder contents.

In one aspect, the turbulence arises as a result of the creation of shear stress, which assists in entrainment of the medicament powder by the airflow. Shear stress is generally defined to mean velocity gradient normal to the direction of airflow. Thus, a region of high shear stress ('high shear') is one in which there is a relatively large velocity gradient over a relatively short distance.

The Applicant believes that the presence of such turbulence can be particularly beneficial where the medicament powder comprises non-cohesive powder components (e.g. one that is non-sticky or only loosely associated e.g. non-agglomerated). The well-known Carr Index may be used to quantify the cohesiveness of a particular powder for delivery by the manifold and medicament dispenser device herein. Methods for measuring Carr Index are described in the following references: Carr, R L (1965) Chem Eng 72(1) page 162; Carr, R L (1965) Chem Eng 72(2) page 69; and Pharmaceutics: The Science of Dosage Form (1988) Ed. Aulton, M E, Churchill Livingstone, N.Y.

In one aspect herein, turbulent flow is created at the open blister pocket by providing plural chimney exits to the chimney, each of which directs airflow at the open blister pocket. In one particular aspect, the plural chimney exits are positioned such that in use, plural airflow jets are directed towards each other to produce a turbulent (e.g. high shear) interaction. The plural chimney exits (and hence, plural airflow jets) are suitably positioned at an angle (θ) relative to each other wherein θ is typically from 150° to 30°, preferably from 120° to 60°.

In another aspect herein, turbulent flow is created at the open blister pocket by shaping the chimney and/or chimney exits to produce a non-linear airflow. In one particular aspect, the chimney and/or chimney exits are shaped to produce a helical (e.g. vortex-like) airflow that is inherently turbulent.

In a further aspect herein, an obstacle is positioned within the chimney and/or at the chimney exit to disruptively create a non-linear airflow. In one particular aspect, a crosspiece or divider (e.g. knife-edge form) is provided within the chimney and/or at the chimney exit to disrupt the airflow and to produce turbulent regions of high shear stress.

Suitably, the chimney of the manifold herein is arranged to create regions of acceleration or deceleration in the airflow at the open blister pocket. That is to say, the chimney is arranged such that in use, accelerating or decelerating airflow is presented at the open blister pocket. Such accelerating or decelerating airflow (whether turbulent or not) assists in the entrainment of the medicament powder contents of the open blister pocket, and thereby to assist in emptying of the pocket of its medicament powder contents.

The chimney exit and chamber inlet may each comprise one or more simple openings (i.e. apertures) or alternatively, in aspects certain features may be provided thereto including a 'cross-piece' (e.g. cruciform-shaped) provided at the opening(s) of one or both thereof.

Suitably, the chimney and chamber of the manifold are arranged to be side-by-side each other or one on top of the other to thereby assist with the requirements for (i) the chimney exit and chamber inlet to lie side-by-side each other and (ii) for one or more bleed holes to be provided between the chimney and chamber, as now described in more detail.

The manifold herein provides that entrained medicament powder is transported via the chamber by airflow from the chamber inlet to the chamber outlet. One or more bleed holes (or passages/channels) are provided between the chimney and the chamber such that bleed airflow may be directed into the chamber to disruptively impact the airflow that carries the entrained medicament powder. The presence of so-located one or more bleed holes improves the overall performance (e.g. FP fraction performance) of the manifold.

In particular, it is beneficial for the bleed airflow to promote the break up (e.g. to de-aggregate or de-agglomerate) of the entrained medicament powder in the chamber. In particular, exposing the entrained medicament powder to regions of differential force arising as a result of the introduction of the bleed airflow from the chimney to the chamber assists in promoting the desired powder break up in the chamber.

The promotion of such break up can be particularly beneficial where the medicament powder comprises cohesive powder components (e.g. one that comprises particles that tend to associate with one another or one in which the particles are agglomerated).

Suitably, the one or more bleed holes are provided to a wall that is common to (and acts as a divider between) the chimney and the chamber. Suitably, the chimney and the chamber share a common wall and at least one of, preferably all of, the one or more bleed holes are provided to said common wall.

The one or more bleed holes typically have a total cross-sectional area (i.e. the cross-sectional area of all of the bleed holes added together) of from 1-35 $mm^2$, preferably from 10-30 $mm^2$, most preferably from 15-25 $mm^2$. The one or more bleed holes may define any suitable profile including oval, circular, D-shaped and elongate slot.

In one aspect, the one or more bleed holes are circular or ovular and each bleed hole has a diameter of from 1-7 mm, preferably from 2-5 mm. In another aspect, the one or more bleed holes are D-shaped and have a maximum diameter of from 1-10 mm, preferably from 3-7 mm. In another aspect, the one or more bleed holes comprise or consist of elongate slots and have a length of from 1-20 mm, preferably from 3-10 mm and a width of from 0.5-3 mm, preferably from 0.7-2 mm.

In one particular aspect, two elongate slot form bleed holes arranged in parallel fashion are provided between the chimney and chamber. Preferably, the parallel elongate slot form bleed holes are arranged to be parallel to the air flow within the chamber.

In one aspect, the one or more bleed holes are provided adjacent to (i.e. neighbouring) the chimney exit and/or chamber inlet.

In another aspect, the one or more bleed holes are spaced from the chimney exit and/or chamber inlet. Typically, the spacing of the one or more bleed holes from the chamber inlet amounts to at least 10%, preferably at least 20%, more preferably at least 30% of the length of the chamber measured from the chamber inlet to the chamber exit.

In one aspect, the one or more of the bleed holes are directed towards a wall of the chamber, thereby creating a region of high shear close to that wall and causing the particles to collide with said wall. Preferably, the overall geometry of the chamber is arranged such as to direct the airflow into these regions of high shear and/or to cause collisions with the wall. An additional advantage of directing bleed air at walls of the manifold is to prevent deposition of medicament particles thereon.

Where plural bleed holes are provided, these are suitably directed towards each other such that the resulting bleed jets interact with each other to create regions of high shear. Preferably, the overall geometry of the chamber is arranged such as to direct the airflow into these regions of high shear.

Suitably, in use, the one or more bleed holes direct one or more air jets to impact upon at least one internal surface of the chamber to create at least one zone of high shear thereat, greater than 3 Pa at an air flow rate of 60 liters/minute for the air entering the chimney.

Suitably, in use, medicament powder from the pocket is directed into said at least one zone of high shear within the chamber to break up any agglomerate particle components thereof.

Suitably, in use, the at least one zone of high shear acts such as to reduce the deposition of powder on said at least one internal surface of the chamber.

It will be appreciated that the provision of such one or more bleed holes also results in reduced airflow resistance because a proportion of the airflow (as originally drawn into the chimney) is not being drawn across the open blister pocket. The provision of bleed holes may therefore potentially impact the effectiveness of emptying of the opened blister pocket of its medicament contents. A compromise between the creation of regions of accelerating airflow by providing one or more bleed holes (good for powder break up in the chamber) and the reduction of airflow resistance (and potentially impacting upon pocket emptying) must therefore be struck. As a general rule, the airflow resistance of the manifold should not be reduced to below a level wherein pocket emptying is compromised at a minimum flow rate of 30 liters/minute for the air entering the chimney.

Typically, the manifold herein is arranged such that from 3 to 50%, preferably from 5 to 25%, more preferably from 15 to 25% (e.g. about 20%) of the airflow entering the chimney inlet is directed via the chimney exit towards the open blister pocket. The remainder of the airflow (e.g. about 80%) is therefore not directed towards the open blister pocket and instead passes through the one or more bleed holes to the chamber. In general terms, for a weakly cohesive powder it is desirable that less airflow is directed through the pocket than for a strongly cohesive powder.

In aspects herein, the size and/or location of any inlet, outlet and/or one or more bleed hole(s) of the manifold is tuned to achieve the desired level of airflow through the pocket and/or airflow resistance and/or shear within the manifold, in use. It will be appreciated that such tuning may take into account the cohesiveness or otherwise of the medicament powder to be delivered through the manifold.

Additionally, powder break up in the chamber may be further promoted if the chamber geometry and shape is arranged of itself, to create regions of high differential force (e.g. high shear). Suitable regions of high shear may be created if the diameter and/or shape of the chamber varies suitably along its length (i.e. along the path of airflow that it defines) such that airflow and entrained powder flowing therethrough tend to encounter walls of the chamber. Such encounters with walls are always regions of high shear (i.e. high speed or airflow next to low speed of airflow) because at the wall itself the airflow speed is effectively zero.

In another aspect, powder break up may be still further promoted in the chamber if the chamber is arranged such that regions of accelerating or decelerating airflow are created therein. That is to say, powder break up is promoted if an airway and entrained powder experiences region of accelerating or decelerating airflow on flowing through the chamber. Preferably, the overall geometry of the chamber is arranged such as to direct the airflow carrying the entrained particles into these regions of accelerating airflow.

It will be appreciated that in use, the presence or otherwise of accelerating or decelerating airflow in the manifold herein can depend on either the patient inhalation profile or the manifold geometry. Thus, a patient inhalation profile that involves a change from slow inhalation to rapid inhalation will result in a 'patient created' region of accelerating airflow. On the other hand, a manifold geometry that (for any patient inhalation profile) results in regions of slow moving airflow being created adjacent to regions of fast moving airflow results a desired region of accelerating airflow. Alternatively, the manifold may be provided with features such as flaps or valves that open up in response to a particular airflow pressure thereby creating an 'acceleration' from zero flow (i.e. flap or valve closed) to permitted flow (i.e. flap or valve open).

Suitably, in use, the manifold is arranged to modify the effect of a user's inhalation profile to increase the acceleration experienced by the powder when it is aerosolised in the blister pocket.

Suitably, in use, the manifold is arranged to modify the effect of a user's inhalation profile to increase the acceleration experienced by the powder as it travels through the chamber from the blister pocket to the patient.

Enhanced propensity for a given patient inhalation profile to give rise to regions of accelerating airflow may suitably be created if the cross-sectional area (e.g. diameter) of the chamber is reduced in the direction of flow. It will be appreciated that a smaller cross-sectional area will mean that the air has a higher velocity for a given flow rate. The acceleration for a given inhalation profile will therefore be proportionally greater.

Suitable regions of accelerating or decelerating airflow also may be created at the manifold if the cross-sectional area (e.g. diameter) of the chamber is arranged to vary in diameter, for example to narrow along its length (i.e. along the path of airflow that it defines) such that airflow and entrained powder flowing there through encounters a narrower cross-section or alternatively to broaden along its length (i.e. along the path of airflow that it defines) such that airflow and entrained powder flowing there through encounters a broader cross-section.

It will be appreciated that any such reduction of chamber cross-sectional area will also result in increased airflow resistance, and therefore may potentially impact the effectiveness of emptying of the opened blister pocket of its medicament contents. A compromise between creating regions of accelerating airflow by reducing chamber cross-sectional area (good for powder break up) and increasing airflow resistance (and potentially impacting upon pocket emptying) must therefore be struck.

In one aspect, the diameter of a chamber of circular profile narrows from about 14-16 mm at the chamber inlet end to about 5-8 mm at the chamber exit end.

In another aspect, the diameter of a chamber is about 5-7 mm across its entire length (as opposed to a conventional diameter of about 14-16 mm).

In a further aspect, powder break up may be still further promoted in the chamber if the chamber is arranged such that mechanical obstacles are created therein. That is to say, powder break up is promoted if an airflow/entrained powder experiences mechanical obstacles on flowing through the chamber.

Suitable mechanical obstacles that may be provided to the chamber comprise or consist of baffles, propellers, paddles, vanes and venturi forms. Alternatively, the chamber itself may be shaped with features (e.g. with defined surface indentations or protrusions) that provide mechanical obstacles.

The manifold performance may be further enhanced if the manifold is arranged such as to delay the emptying of the medicament powder contents of the blister pocket.

In one aspect such delay is achieved by reducing the amount of air that flows through the open blister pocket. Such reduction must not however, be too pronounced since insufficient airflow through the pocket can prevent the complete emptying of the medicament contents of the open blister pocket. Such reduction of airflow through the open blister pocket is achieved by providing the manifold with one or more bleed holes positioned such as to 'divert' airflow from the opened pocket.

The manifold performance may be enhanced where the manifold is arranged such as to delay the emptying of the medicament powder contents of the blister pocket until regions of differential force (e.g. high shear/accelerating air) capable of causing powder break up are created in the chamber. If the pocket empties too early the powder to be broken up will have passed the through the high differential force zones before they are fully established so delaying the empting of the pocket will improve manifold performance by ensuring that more of the powder experiences a region of high shear.

Suitably, the manifold herein is arranged such as to delay the emptying of the medicament powder contents of the blister pocket until a predetermined flow rate through the manifold chamber (i.e. not just through the blister pocket) is achieved by the inhaling patient. Whilst the value for the predetermined flow rate may be fine tuned, it is generally desirable that it has a value of between 5 to 45 liters/minute, preferably 20 to 30 liters/minute.

Desirably, the manifold herein acts overall such as to enhance the uniformity of medicament dose delivered thereby.

Desirably, the manifold herein acts overall such as to increase the Emitted Dose (ED) of the medicament powder that is made available at the chamber exit/mouthpiece for inhalation by the patient. The ED is generally measured by collecting the total amount of medicament powder emitted from the dispenser device for example, using a dose sampling apparatus such as a Dose Uniformity Sampling Apparatus (DUSA). The ED may also be expressed as a percentage (% ED) of the measured dose (MD) contained within the particular blister(s) from which medicament powder is liberated. Thus, in this case, % ED is calculated as (ED/MD)×100%. It is desired that the % ED is at least 95% by weight, preferably more than 98% by weight.

Desirably the manifold herein also acts such as to increase the FP Fraction of the medicament powder that is made available at the chamber exit/mouthpiece for inhalation by the patient.

The term "fine particle fraction of emitted dose" or FP Fraction (ED) refers to the percentage of particles within a given Emitted Dose of aerosolised medicament that is of "respirable" size, as compared to the total emitted dose. A particle size range of from 1-6 μm is generally considered to be of "respirable" size. The FP Fraction (ED) may thus be calculated as a percentage of the Emitted Dose (ED). Thus, in this case, FP Fraction (ED) is calculated as (FPF/ED)×100%. It is desired that the FP Fraction (ED) is at least 25% by weight, preferably more than 30% by weight of the Emitted Dose of particles made available at the chamber exit/mouthpiece.

The FP Fraction may also be defined as a percentage of the measured dose (MD) contained within the particular blister(s) from which medicament powder is liberated. Thus, in this case, FP Fraction (MD) is calculated as (FPF/MD)×100%. It is desired that the FP Fraction (MD) is at least 25% by weight, preferably more than 30% by weight.

The manifold herein is typically provided (as a component part thereof) to a medicament dispenser device that is arranged to receive a blister pack having one or more blister pockets containing medicament in dry powder form.

Suitably, the medicament dispenser device comprises a housing, which can have any suitable shape or form. One preferred form is that of a shell-like housing formed by a mating assembly of two shell halves, which may either be hinged or alternatively, fully separable one half from the other. The housing is formed from any suitable material, but most typically comprises a plastic polymeric material that is relatively robust but is also readily manufactured by a volume manufacturing process.

The housing is suitably provided with an air inlet. This typically takes the form of a hole or holes of suitable shape and size provided to the wall of the housing. The air inlet is suitably positioned such as to locate in a position that would not typically be covered or blocked up by the fingers and/or thumb of a user during normal use thereof. The air inlet is suitably covered at least in part, by a protective grille or other feature which acts such as to prevent blockage and/or to minimize undesirable entry of dirt and other particulate contaminants thereto.

Suitably, enclosed by the housing, there is provided a dispensing mechanism for the dispensing of medicament powder from an open blister pocket of at least one blister pack receivable thereby. Details of suitable dispensing mechanisms are provided by the later description. Associated with the dispensing mechanism and in communication (i.e. fluid/air flow communication) with the air inlet, there is provided a manifold herein.

Suitably, the medicament dispenser device provides that airflow is drawn into the chimney of the manifold solely through the air inlet provided to the housing. That is to say, all air flowing into the manifold does so via the air inlet and the chimney of the manifold.

Thus, during such use the patient inhales through the mouthpiece, which creates negative pressure in the manifold, which causes air to be drawn from outside of the dispenser device through the air inlet and into the chimney of the manifold via the chimney inlet, which is in fluid communication with (e.g. juxtaposed to) the air inlet. At least part of that airflow is then directed from the chimney exit to the chamber inlet via the open blister pocket to entrain the medicament powder contents thereof.

Preferably, the air inlet provides the sole entry point for air flow into the medicament dispenser device, and particularly to the open blister pocket of the blister pack, during inhaled use of the dispenser device by a patient. Thus, suitably no other air inlet or other air entry point is provided to the housing and the housing itself provides a relatively air tight barrier to the entry of outside air therein by any other means.

Suitably, the cross-sectional area of the air inlet provided to the housing of the medicament dispenser device is greater than (for example, at least one and a half times, preferably double) the cross-sectional area of any part of the manifold, which incoming air will experience (downstream) in the manifold. Thus, the cross-sectional area of the air inlet is suitably greater than any of the cross-sectional area of the chimney; the total cross-sectional area of the chimney exit and one or more bleed holes; and the cross-sectional area of the chamber. The rationale for this is that the air inlet cannot therefore act such as to constrict or otherwise affect the nature of the air flow through the dispenser device and thus, all control of air flow (and air pressure etc.) is as a result of the manifold geometry and layout (including the selection of cross-sectional areas for any manifold part).

In one aspect, the blister pack comprises multiple blisters for containment of medicament product in dry powder form. The blisters are typically arranged in regular fashion for ease of release of medicament therefrom. The blisters may have any suitable shape including those with a square, circular, ovular or rectangular profile.

The particular form, including shape and cross-sectional area, of the blister pocket affects the airflow properties, and particularly airflow resistance and pressure drop experienced at the open pocket when a patient inhales through the manifold herein.

By way of an example: a typical dose of medicament powder in a blister pocket is 17 µl. If the pocket took the form of a sphere, to accommodate this dose it would have a radius of 1.7 mm and a cross-sectional area of 8.0 mm$^2$ A flow of 60 l/min through an area of 8 mm$^2$ equates to an average velocity of 125 m/s. The pressure drop due to this flow will be approximately equal to:

$$\Delta P = \frac{K\rho v^2}{2}$$

(where $\rho$=density of air=1.3 kg/m$^3$, V=mean velocity=125 m/s and K=a geometric factor).

For a sudden contraction from a large cross-section to 8.0 mm$^2$, K=0.5 (approx.) so the pressure drop will be 5.1 kP. For a sudden expansion from 8.0 mm$^2$ to a large cross-sectional area K=1 (approx.) so the pressure drop will be 10.2 kPa Thus, a pocket geometry with an 8.0 mm$^2$ inlet and an 8.0 mm$^2$ outlet would have a resistance of 15.3 kPa at 60 liters/minute.

The resistivity of the pocket is =$\sqrt{(15.3)/60}$=0.065 (kPa)$^{0.5}$ min/l so for a pressure drop of 2 kPa the flow would be =$\sqrt{(2)/0.065}$=22 l/min, this is about ⅓ of the total flow.

In the case of a blister pocket suitable for use with the well-known Diskus (trade mark) device as sold by GlaxoSmithKline Plc, and as described in more detail hereinbelow, the medicament powder is more stretched out (not in a sphere) the cross-section in the pocket is in the region of 4 mm$^2$ so the average velocity at 60 liters/minute would be 250 m/s.

For a simple inlet-outlet system (as above) the pressure drop at 60 liters/minute would be 61.2 kPa, the resistivity would be 0.130 (kPa)$^{0.5}$ minute/liter and the flow for a pressure drop of 2 kPa would be 11 liters/minute (18% of flow). For a blister pocket suitable for use with the well-known Diskus (trade mark) device, the resistivity would be about 0.15 (kPa)$^{0.5}$ minute/liter and the flow for a pressure drop of 2 kPa would be 9.4 liters/minute (16% of flow of 60 liters/minute).

In one aspect, the multi-dose blister pack comprises plural blisters arranged in generally circular fashion on a disc-form blister pack. An example of a medicament dispenser device suitable for dispensing medicament powder from such a disk-form blister pack is the well-known Diskhaler (trade mark) device as sold by GlaxoSmithKline Plc.

In another aspect, the blister pack is elongate in form, for example comprising a strip or a tape. Preferably, the blister pack is defined between two members peelably secured to one another. U.S. Pat. Nos. 5,860,419, 5,873,360 and 5,590,645 in the name of Glaxo Group Ltd describe medicament packs of this general type. In this aspect, the device is usually provided with an opening station comprising peeling means for peeling the members apart to access each medicament dose.

Suitably, the medicament dispenser device is adapted for use where the peelable members are elongate sheets that define a plurality of medicament containers spaced along the length thereof, the device being provided with indexing means for indexing each container in turn. More preferably, the medicament dispenser device is adapted for use where one of the sheets is a base sheet having a plurality of pockets therein, and the other of the sheets is a lid sheet, each pocket and the adjacent part of the lid sheet defining a respective one of the containers, the medicament dispenser device comprising driving means for pulling the lid sheet and base sheet apart at the opening station. An example of medicament dispenser device of this type is the well-known Diskus (trade mark) device as sold by GlaxoSmithKline Plc.

In one aspect, the blister form medicament pack comprises
(a) a base sheet in which blisters are formed to define pockets therein containing a an inhalable dry powder medicament formulation;
(b) a lid sheet which is sealable to the base sheet except in the region of the blisters and mechanically peelable from the base sheet to enable release of said inhalable dry powder medicament formulation,
wherein said base sheet and/or said lid sheet have a laminate structure comprising (a) a first layer of aluminium foil; and (b) a second layer of polymeric material of thickness from 10 to 60 micron.

The base and lid sheets are typically sealed to one another over their whole width except for the forward end portions where they are typically not sealed to each other at all. Thus, separate base and lid sheet forward end portions are presented at the end of the strip.

Suitably, the polymeric material has a water vapour permeability of less than 0.6 g/(100 inches$^2$) (24 hours) (mil) at 25° C. The water vapour permeability is suitably measured by ASTM test method no. ASTM E96-635 (E).

Suitably, the polymeric material comprises a material selected from the group consisting of polypropylene (e.g. in oriented or cast form; standard or metallocene); polyethylene (e.g. in high, low or intermediate density form); polyvinyl chloride (PVC); polyvinylidene chloride (PVDC); polychlorotrifluoroethylene (PCTFE); cyclic olefin copolymer (COC); and cyclic olefin polymer (COP).

Suitably, the lid sheet comprises at least the following successive layers: (a) paper; bonded to (b) plastic film; bonded to (c) aluminium foil.

The aluminium foil is typically coated with a layer (e.g. of heat seal lacquer; film or extrusion coating) for bonding to the base sheet material.

The thickness of each of the layers of the lid sheet may be selected according to the desired properties but is typically of the order of from 5 to 200 micron, particularly from 10 to 50 micron.

The plastic layer is in one aspect, suitably selected from polyester (non-oriented, monaxial, or biaxial oriented), polyamide, polypropylene or PVC. In another aspect the plastic film is an oriented plastic film, suitably selected from oriented polyamide (OPA); oriented polyester (OPET); and oriented polypropylene (OPP). The thickness of the plastic layer is typically from 5 to 40 µm, particularly 10 to 30 µm.

The thickness of the aluminium layer is typically from 10 to 60 µm, particularly 15 to 50 µm such as 20 to 30 µm.

In aspects, the paper layer comprises a paper/extrusion layer, optimally laminated to aluminium.

In one particular aspect, the lid sheet comprises at least the following successive layers: (a) paper; bonded to (b) polyester; bonded to (c) aluminium foil; that is coated with a heat seal lacquer for bonding to the base sheet. The thickness of each layer may be selected according to the desired properties but is typically of the order of from 5 to 200 micron, particularly from 10 to 50 micron.

The bonding may in aspects be provided as an adhesive bond (e.g. solvent-based adhesive wherein the solvent is organic or water-based); solvent free adhesive bond; extrusion-laminated bond; or heat calandering.

Suitably, the base sheet comprises at least the following successive layers: (a) oriented polyamide (OPA); adhesively bonded to (b) aluminium foil; adhesively bonded to (c) a third layer of thickness from 10 to 60 micron comprising a polymeric material. The polymeric material preferably has a water vapour permeability of less than 0.6 g/(100 inches$^2$) (24 hours) (mil) at 25° C. The third layer will bond with the lid sheet, which is generally treated with a heat seal lacquer.

The thickness of each non-polymeric layer of the base sheet may be selected according to the desired properties but is typically of the order of from 5 to 200 micron, particularly from 20 to 60 micron. In accord with the invention, the thickness of the polymeric layer is selected to reduce moisture ingress, and is from 10 to 60 micron, particularly from 25 to 45 micron, preferably from 30 to 40 micron.

Suitably, the polymeric material is selected from the group consisting of polypropylene (in oriented or cast form; standard or metallocene); polyvinyl chloride (PVC); polyethylene (in high, low or intermediate density form); polyvinylidene chloride (PVDC); polychlorotrifluoroethylene (PCTFE); cyclic olefin copolymer (COC); and cyclic olefin polymer (COP). Optionally, other layers of material are also present.

Various known techniques can be employed to join the lid and base sheet and hence to seal the blisters. Such methods include adhesive bonding, radio frequency welding, ultrasonic welding and hot bar sealing.

The base sheet herein is particularly suitable for forming by 'cold form' methods, which are conducted at lower temperatures than conventional methods (e.g. at close to room temperature). Such 'cold form' methods are of particular utility where the medicament or medicament formulation for containment within the blister is heat sensitive (e.g. degrades or denatures on heating).

The blister pack is suitably receivable by a medicament dispenser comprising the manifold herein that also comprises a housing for receipt of the pack. In one aspect, the medicament dispenser has unitary form and the housing is integral therewith. In another aspect, the medicament dispenser is configured to receive a refill cassette and the housing forms part of that refill cassette.

Suitably, the interior of the housing is shaped, or alternatively provided with specific guiding features, to guide the blister form medicament pack appropriately into the housing. In particular, the guiding should ensure that the blister pack is suitably located to interact with internal mechanisms (e.g. indexing and opening mechanisms) of the housing.

Suitably, the medicament dispenser device has an internal mechanism for dispensing the distinct dry powder medicament doses carried by the blisters of the blister pack for administration to the patient (e.g. by inhalation). Suitably, the mechanism comprises,
a) a receiving station for receiving the blister pack;
b) a release station for releasing a distinct medicament dose from a blister of the blister pack on receipt thereof by said receiving station; and
c) an indexing station for individually indexing the distinct medicament doses of the blister pack,
wherein the manifold herein is positioned to be in communication with the medicament dose releasable by said release station.

The mechanism comprises receiving means (e.g. a receiving station) for receiving the blister pack.

The mechanism further comprises release means for releasing a distinct medicament dose from a blister of the blister pack on its receipt by the receiving station. The release means typically comprises means for mechanically peeling apart the blister strip.

A manifold herein is positioned to be in communication with the distinct medicament powder doses releasable by said release means. Delivery of the so-released medicament to the patient for inhalation thereby, is preferably through a single outlet that communicates with or forms an integral part with the manifold. The outlet may have any suitable form. In one aspect, it has the form of a mouthpiece for insertion into the mouth of a patient; and in another it has the form of a nozzle for insertion into the nasal cavity of a patient.

The mechanism also comprises indexing means for individually indexing the distinct medicament dose-containing blisters of the blister form medicament pack. Said indexing typically happens in sequential fashion, for example accessing dose portions sequentially arranged along the length of the blister form medicament pack.

Optionally, the medicament dispenser also includes counting means for counting each time a distinct medicament dose of the blister form medicament pack is indexed by said indexing means.

In one aspect, counting means is arranged to count each time a distinct medicament dose of the medicament carrier is indexed by said indexing means. Suitably, the indexing means and counting means engage directly or indirectly (e.g. via a coupling) with each other to enable counting of each indexation.

Suitably, the counting means is provided with (or communicates with) a display for displaying to the patient the number of distinct doses left to be taken or the number of doses taken.

In one preferred aspect, the medicament dispenser takes the form of a dispenser for use with a blister form medicament pack herein having multiple distinct pockets for containing inhalable medicament doses, wherein said pockets are spaced along the length of and defined between two peelable sheets secured to each other, said dispenser having an internal mechanism for dispensing the medicament doses contained within said medicament pack, said mechanism comprising,
a) an opening station for receiving a pocket of the medicament pack;
b) a peeler positioned to engage a base sheet and a lid sheet of a pocket which has been received in said opening station for peeling apart such a base sheet and lid sheet, to open such a pocket, said peeling means including a lid driver for pulling apart a lid sheet and a base sheet of a pocket that has been received at said opening station; and
c) an indexing station for individually indexing the distinct pockets of the medicament pack,
wherein the manifold herein is positioned to be in communication with an opened pocket through which medicament dose is deliverable from such an opened pocket.

Suitably, the indexing means comprises a rotatable index wheel having recesses therein, said index wheel being engageable with a medicament pack in use with said medicament dispenser such that said recesses each receive a respective pocket of the base sheet of a blister strip in use with said medicament dispenser.

According to another aspect of the present invention there is provided a medicament dispenser comprising (e.g. loaded with) at least one dry powder medicament-containing blister pack herein.

The manifold herein has hereinbefore been described in terms of its use with a medicament dispenser device suitable for dispensing medicament from the opened pocket of a blister pack. It will be appreciated that the manifold may also be employed for use with any medicament dispenser device suitable for dispensing medicament from an open cavity, wherein that cavity might for example, be provide by an opened capsule of a capsule form pack.

Thus, according to a further aspect of the invention there is provided a manifold for use in a medicament dispenser device for the delivery of medicament powder from an open cavity of a medicament pack, the manifold comprising
a body,
said body defining a chimney having a chimney inlet and a chimney exit for directing airflow from said chimney inlet to said chimney exit;
the body further defining a chamber having a chamber inlet and a chamber exit,
wherein the chimney exit and said chamber inlet lie side-by-side each other such that when said open cavity is positioned adjacent thereto said airflow is directed from the chimney exit to the chamber inlet via the open cavity to entrain said medicament powder and enable transport thereof in the airflow from the chamber inlet to said chamber outlet,
and wherein one or more bleed holes are provided between the chimney and the chamber such that bleed airflow is able to be directed into the chamber to disruptively impact the airflow that transports the entrained medicament powder.

Suitably, the medicament dispenser herein is packaged within a package (i.e. an outer package, for example in the form of an overwrap) comprising a packaging material that is designed to reduce ingress of environmental moisture to the dispenser (and medicament pack thereof) packaged thereby.

The package is suitably formed any material which is impervious to or substantially impervious to moisture. The packaging material is preferably permeable to volatiles which may escape from the plastics forming the body of the inhaler and/or the blister form medicament pack, by diffusion or otherwise, thereby preventing a build-up in pressure.

Further aspects and features of the invention are disclosed in the accompanying claims and in the following detailed description of exemplary embodiments made with reference to the accompanying Figures.

BRIEF DESCRIPTION OF THE DRAWINGS

FIG. 1 shows a perspective view of a blister pack-form medicament carrier in elongate strip form suitable for use with a medicament dispenser device in accord with the present invention;

FIG. 2 shows a sectional side view of a medicament dispenser device comprising the medicament carrier of FIG. 1, the dispenser device being suitable for adaptation in accord with the present invention;

FIG. 3*a* shows a highly schematic, sectional side view of the base unit of a second medicament dispenser device comprising a pair of the medicament carriers of FIG. 1 and suitable for use in accord with the present invention;

FIG. 3*b* shows a highly schematic perspective view of a detail of the base unit of FIG. 3*a;*

FIGS. 4*a* to 4*c* show in perspective view sequential steps for preparing a third medicament dispenser device for dispensing use by a patient, the device containing a pair of the medicament carriers of FIG. 1;

FIGS. 5*a* to 5*c* show in side view corresponding sequential steps for preparing the third medicament dispenser device for use where the dispenser device is shown absent a part of its outer housing;

FIG. 6 shows in exploded perspective view a gear mechanism of the third medicament dispenser device;

FIGS. 7*a* to 7*c* show in side view details of the gear mechanism when prepared for use in sequential steps corresponding to those of FIGS. 4*a* to 4*c* and 5*a* to 5*c;*

FIG. 8 shows in perspective side view a detail of a ratchet 'anti return' mechanism of the third medicament dispenser device;

FIG. 9 shows in perspective side view the dispensing mechanism and the medicament carriers of the third medicament dispenser device;

FIG. 10 shows a part-exploded view of the third medicament dispenser device, absent its mouthpiece;

FIG. 11 shows a side view of one half of the shell housing of the third medicament dispenser device having a manifold provided thereto;

FIG. 12 shows a cut-away view of the third medicament dispenser device;

FIG. 13 shows a cut-away view of an assembly of the mouthpiece and a first manifold of the third medicament dispenser device;

FIG. 14*a* shows a side view of the first manifold in FIG. 13;

FIG. 14*b* is a cross-sectional side view of the first manifold taken on line XIVb in FIG. 15*b* showing its 'in use' relationship with the medicament carriers of the third medicament dispenser device;

FIGS. 15*a* and 15*b* are cross-sectional plan views of the first manifold taken on lines XVa and XVb in FIG. 14*a* respectively illustrating the flow of primary and bleed air therethrough upon inhalation by a patient at the mouthpiece of the third medicament dispenser device;

FIG. 15*c* is a schematic, cross-sectional side view of the first manifold taken on line XVc in FIG. 14*b* showing the flow of primary and bleed air therethrough upon patient inhalation on the mouthpiece of the third medicament dispenser device;

FIG. 16*a* shows a side view of an alternative manifold suitable for use in the mouthpiece and manifold assembly of FIG. 13;

FIG. 16*b* is a cross-sectional side view of the alternative manifold taken on line XVIb in FIG. 17*b* showing its 'in use' relationship with the medicament carriers of the third medicament dispenser device;

FIG. 17*a* shows a cut-away view of the assembly of the mouthpiece and the alternative manifold of the third medicament dispenser device; and FIGS. 17*b* and 17*c* are cross-sectional plan views of the alternative manifold taken on lines XVIIb and XVIIc in FIG. 16*b* respectively illustrating the flow of primary and bleed air therethrough upon inhalation by a patient at the mouthpiece of the third medicament dispenser device.

DETAILED DESCRIPTION OF THE DRAWINGS

FIG. 1 shows a medicament carrier 100 having elongate blister strip form. The medicament carrier 100, which is of the type used in the DISKUS® ADVAIR® dry powder inhaler of GlaxoSmithKline Plc, comprises a flexible strip 102 defining a plurality of pockets 104 each of which contains a dose (or portion thereof) of inhalable medicament powder. The strip 102 is sufficiently flexible to be wound into a roll, as shown in FIG. 1.

The strip 102 comprises a base sheet 110 in which blisters 106 are formed, by cold forming or deep drawing, to define the pockets 104 and a lid sheet 112 which is hermetically sealed to the base sheet 110, except in the region of the blisters 106, to hermetically cover the pockets 104. The hermetic sealing of the base and lid sheets 110, 112 is such that the base and lid sheets 110, 112 are able to be peeled apart to open the pockets 104 for access to the medicament powder. The sheets 110, 112 are sealed to one another over their whole width except for the leading end portions 114, 116 where they are preferably not sealed to one another at all.

The lid 112 and base 110 sheets are each formed of a plastics/aluminium laminate and are adhered to one another by heat sealing. The lid sheet 112 comprises at least the following successive layers: (a) paper; adhesively bonded to (b) polyester; adhesively bonded to (c) aluminium foil; that is coated with a heat seal lacquer for bonding to the base sheet. The base sheet 110 comprises at least the following successive layers: (a) oriented polyamide (OPA); adhesively bonded to (b) aluminium foil; adhesively bonded to (c) a third layer comprising a polymeric material (e.g. polyvinyl chloride).

Alternatively, the lid sheet 112 may be constructed as described in International patent application No. PCT/US06/37438 filed 26 Sep. 2006, the entire content of which International application, and its counterpart US national phase application, is incorporated herein by reference.

The pockets 104 are identical to one another and, with the exception of a test pocket 108 at the leading end of the strip 102, are equi-spaced along the strip length. The pockets 104 are elongate and extend transversely with respect to the length of the strip 102. This is convenient in that it enables a large number of pockets 104 to be provided in a given strip length. The strip 102 may, for example, be provided with thirty, sixty or one hundred pockets 104, but it will be understood that the strip 102 may have any suitable number of pockets 104.

Further details of the strip 102 may be found in U.S. Pat. No. 5,590,645, the entire content of which is hereby incorporated herein by reference.

In embodiments of the present invention, examples of which follow herein, plural such strips 102 are employed in a single medicament dispenser device, wherein each strip provides the component medicament dose portions of a combination medicament product. Each such strip 102 may be of the same size and/or contain the same dose amount (e.g. volume or mass) or in alternative embodiments, strips of different sizes and/or containing different dose amounts may be employed in combination.

Figure 2:
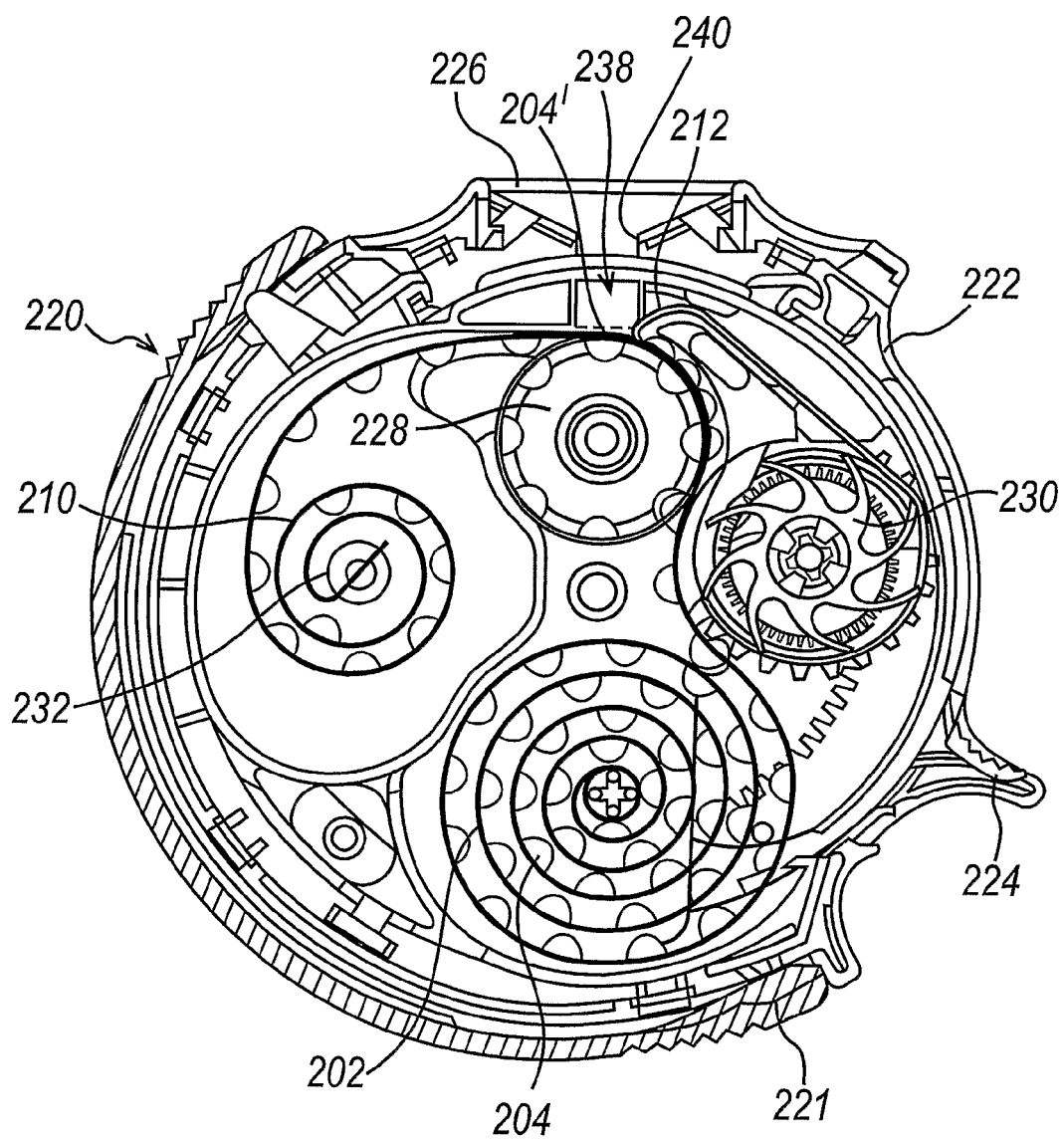

FIG. 2 shows a first hand-held, hand-operable medicament dispenser device in the form of a dry powder inhaler that may be adapted to comprise a manifold in accord with the present invention. The inhaler 220 is of the general type sold by GlaxoSmithKline Plc under the trade mark DISKUS®, details of which are disclosed in U.S. Pat. No. 5,590,645 supra, particularly with reference to FIGS. 13 to 16 thereof. The inhaler 220 contains the medicament carrier of FIG. 1, herein designated 202 with the other strip features being assigned like numerals.

In more detail, the inhaler 220 is arranged to dispense unit doses of medicament powder from pockets 204 of the elongate blister strip 202. The inhaler is comprised of an outer casing 221 enclosing medicament strip 202 within body 222. The patient uses the inhaler by holding the device 220 to his mouth, depressing lever 224, and inhaling through mouthpiece 226. Depression of lever 224 activates the internal mechanism of the inhaler, such that the lid 212 and base 210 sheets of coiled medicament blister strip 202 are separated by peeling apart at index wheel 228 as a result of the pulling action of lid sheet take-up wheel 230. It will be appreciated that once peeled apart, the lid sheet 212 is coiled around the take-up wheel 230. In turn, the separated base sheet 210 coils around base sheet take-up wheel 232. A unit dose of powdered medicament within opened blister pocket 204' is released at opening station 238 and may be inhaled by the patient through manifold cavity 240 and ultimately mouthpiece 226. The exact form of the manifold that would be provided to the manifold cavity 240 is not visible in FIG. 2, but will have a form in accord with the present invention and as shown in the later Figures herein.

Figure 3A:
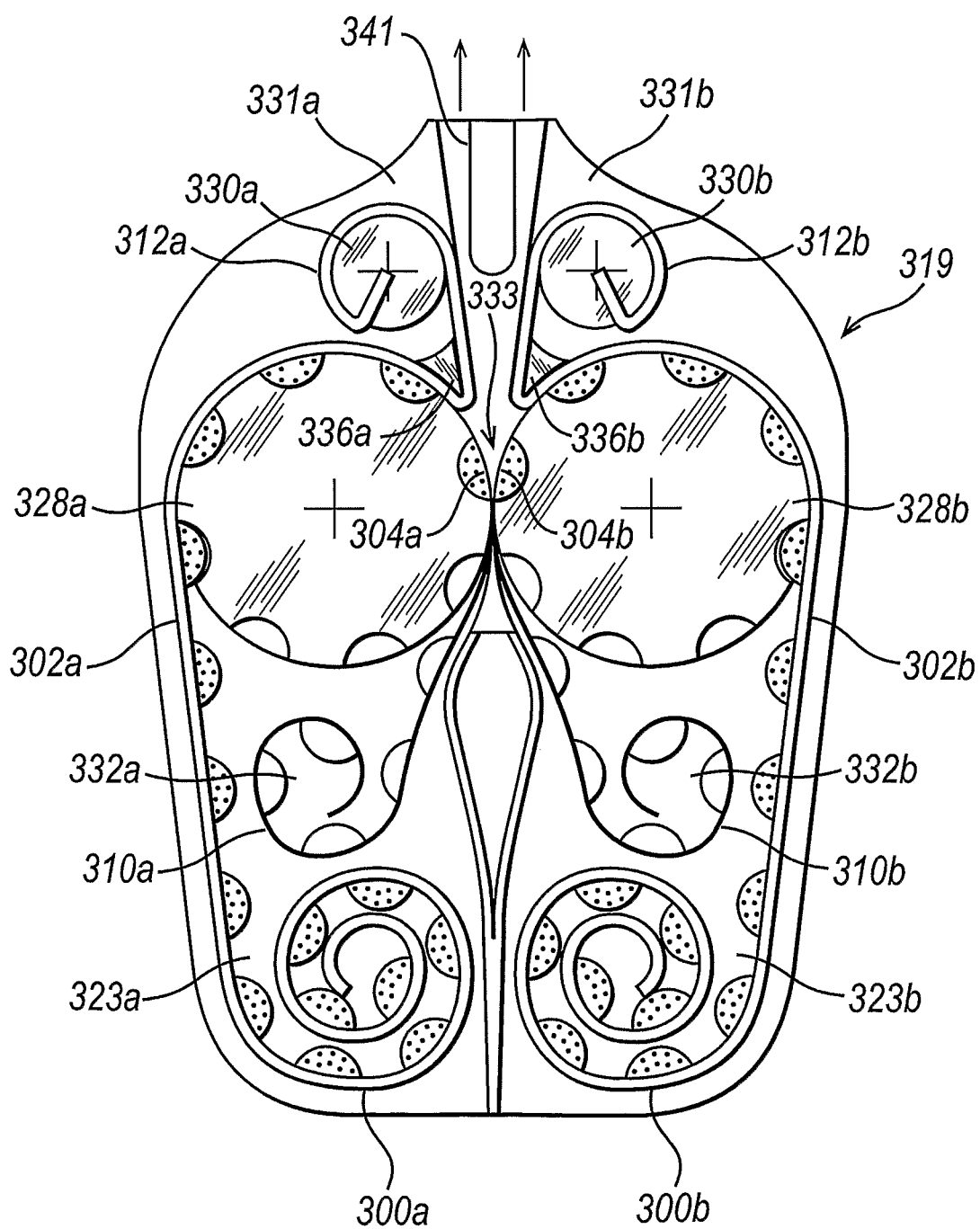
Figure 3B:
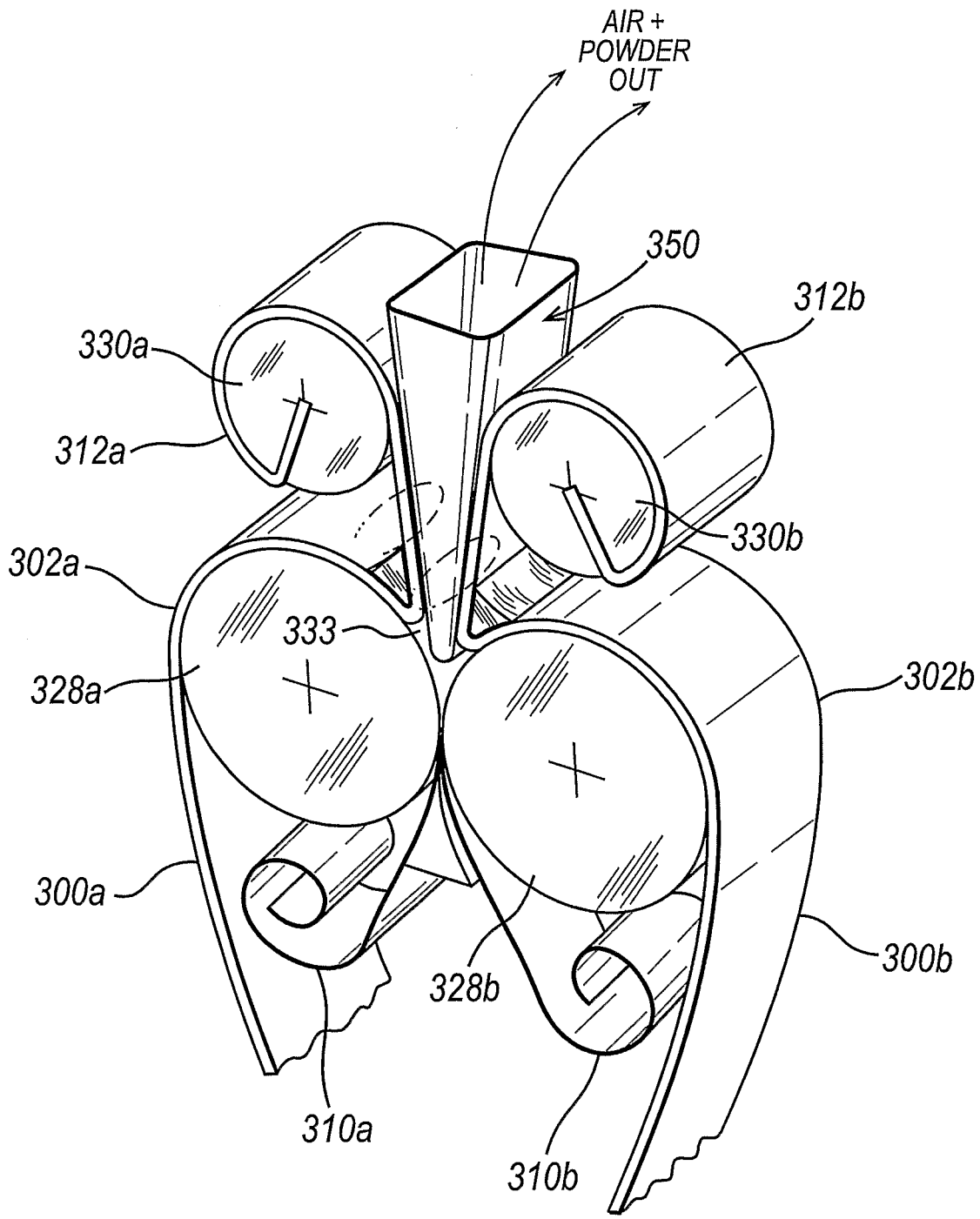

FIGS. 3a and 3b are highly schematic views of a second hand-held, hand-operable medicament dispenser device in accordance with the present invention which is in the form of a dry powder inhaler and of the type disclosed in US-A-2005/0154491 (Anderson et al), the entire content of which is incorporated herein by reference.

That is to say, the second medicament dispenser device is provided with two medicament carriers 300a, 300b in the form of the flexible blister strips 302a, 302b described above with reference to FIG. 1 (like reference numerals being used to designate the features thereof). The flexible blister strips 302a, 302b are identical, the pockets in each being of the same shape and size and being equi-spaced along the strip length.

A first one of the strips 302a contains the same medicament powder in each of its pockets, with the amount of active ingredient(s) also being the same in each pocket of that strip. The other strip 302b similarly contains a common medicament powder in each of its pockets, each such pocket again having the same amount of active ingredient(s) therein. The medicament powder in each strip may contain a single active ingredient or a mixture of active ingredients. However, the medicament powder in one strip contains at least one active ingredient not in the other strip. As to be detailed further hereinafter, on operation of the second medicament dispenser device, a pocket of each blister strip 302a, 302b is peeled open to expose the different medicament powders therein. The patient then inhales on the mouthpiece to simultaneously inhale the powders from the open pockets 304a, 304b of the strips 300a, 300b. The patient thus receives a fixed metered dose of medicament powder of which the different medicament powders from each open pocket 304a, 304b make up respective dose portions.

FIG. 3a illustrates a base unit 319 of the second medicament dispenser device. The first and second medicament-containing blister strips 302a, 302b are positioned within respective left and right chambers 323a, 323b of the base unit 319. Each blister strip 302a, 302b engages a respective multi-pocket index wheel 328a, 328b, and successive pockets are thereby guided towards a commonly located opening station 333. The rotation of the index wheels 328a, 328b is coupled. At the opening station 333, the lid foil 312a, 312b and base foil 310a, 310b parts of each strip 302a, 302b are peelably separable about a respective beak 336a, 336b. The resulting empty base foil 310a, 310b coils up in respective base take-up chambers 332a, 332b. The used lid foil 312a, 312b is fed over its respective beak 336a, 336b and coiled about a lid take-up spindle 330a, 330b in the lid take-up chamber 331a, 331b.

Released powder form medicament from opened pockets 304a, 304b of both the first 302a and second 302b strips is accessible via a manifold 350, which is only shown schematically in FIG. 3b, but which in this embodiment takes the form of one of the manifolds 450, 550 shown in FIG. 14a or FIG. 16a and described in detail with reference to the third medicament dispenser device of FIGS. 4 to 17. The manifold 350 locates at manifold-receiving station 341.

In use, released powder travels from the manifold 350 to a mouthpiece (not shown) in fluid communication therewith for inhalation by the patient. The manifold 350 defines a particular geometry through which the released powders travel for mixing thereof prior to delivery at the mouthpiece. The base unit 319 of FIG. 3a enables different medicament types to be stored separately in each of the strips 302a, 302b but the simultaneous release and delivery thereof to the patient as a 'mixed' multi-active combined inhaled product.

FIG. 3b shows the release of medicament from the open pockets 304a, 304b (FIG. 3a) in more detail. The patient breathes in through the mouthpiece (not shown) resulting in negative pressure being transmitted through the manifold 350 to the opened pockets 304a, 304b (FIG. 3a) of the strips 302a, 302b at the opening station 333. This typically results in the creation of a venturi effect which results in the powder contained within each of the opened pockets 302a, 302b being drawn out through the manifold 350 and thence to the mouthpiece for inhalation by the patient.

FIGS. 4 to 15 provide various views of a third hand-held, hand-operable medicament dispenser device in accordance with the present invention. The third medicament dispenser device is in the form of a dry powder inhaler and, as will be understood by the skilled reader, is similar in term of its function and general principal of operation as the second medicament dispenser device supra.

That is to say, the third medicament dispenser device is provided with two medicament carriers 400a, 400b in the form of flexible blister strips 402a, 402b, as described above with reference to FIG. 1, with like reference numerals being used to designate the features thereof. However, in the strips 402a, 402b the test pocket forms part of the equi-spaced series of pockets 404a, 404b, instead of being spaced farther away. The number of pockets 404a, 404b in each strip 402a, 402b is the same, the precise numbering depending on how many days treatment is intended and the dosing regime. As an example, the strips 402a, 402b would have 31 pockets each for a once-a-day, 30 day treatment programme. The extra pocket is the test pocket.

The flexible blister strips 402a, 402b are identical, the pockets 404a, 404b in each being of the same shape and size and being equi-spaced along the strip length. A first one of the strips 402a contains the same medicament powder in each of its pockets, with the amount of active ingredient(s) also being the same in each pocket of that strip. The other strip 402b similarly contains a common medicament powder in each of its pockets, each such pocket again having the same amount of active ingredient(s) therein. The medicament powder in each strip may contain a single active ingredient or a mixture of active ingredients. However, the medicament powder in one strip contains at least one active ingredient not in the other strip. As to be detailed further hereinafter, when the device has been prepared for use and a patient inhales on a mouthpiece 426 of the device, the patient simultaneously inhales the powder from a single open pocket 404a, 404b of each strip 400a, 400b to receive a fixed metered dose of medicament powder of which the different medicament powders from each open pocket make up respective dose portions.

FIGS. 4a to 4c and FIGS. 5a to 5c each show corresponding sequential steps for preparing the third medicament dispenser device for use. As shown, the third medicament dispenser device comprises a housing 420 provided with a mouthpiece 426 and a mouthpiece cover 438 for covering the mouthpiece 426. Also provided to housing 420 is a window 424 through which a dose count indicia 425 of a dose counter (not shown) is viewed. As will be described in more detail hereinafter, and as will be understood from FIGS. 6 and 9 to 15, the mouthpiece 426 interacts with a manifold 450 located at an opening station 427, the manifold 450 being arranged, in use, to direct medicament powder from the single opened pocket of each strip 400a, 400b at the opening station 427 for inhalation by a patient.

Figure 5A:
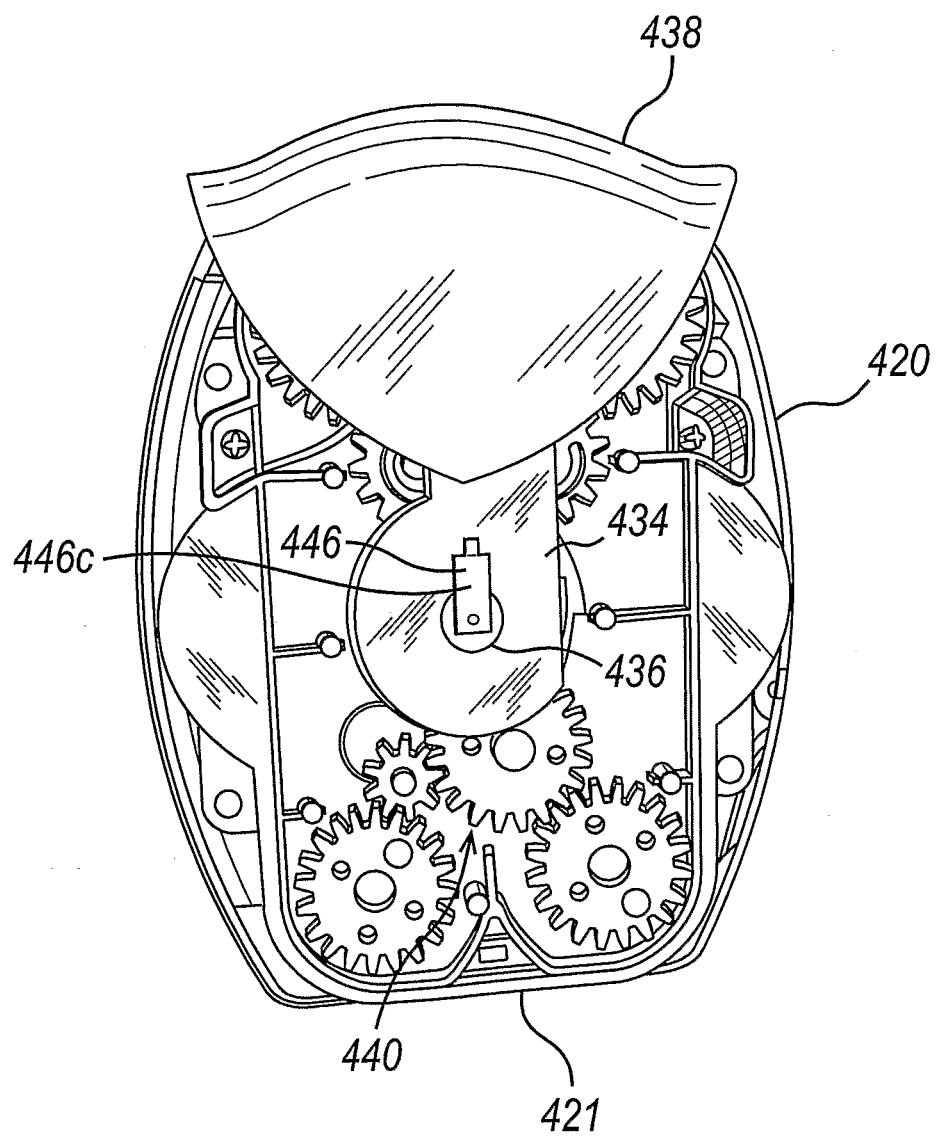

As may be seen in FIG. 5a, the mouthpiece cover 438 has an arm 434 provided with a mounting aperture 436 for mounting for interaction with a ratchet 446 of a complex gear mechanism 440. In use, the mouthpiece cover 438 is rotationally movable about an axis defined by the rotational axis of the ratchet 446.

Figure 4A:
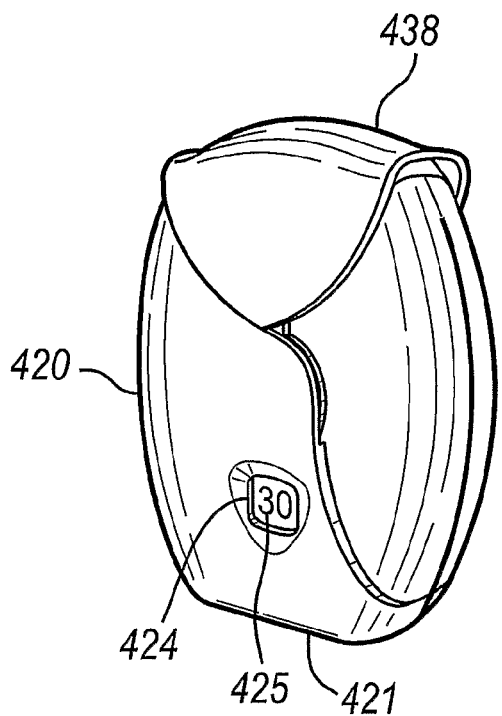

In FIGS. 4a and 5a, the mouthpiece cover 438 is in a first position in which the mouthpiece 426 is covered thereby.

Figure 4B:
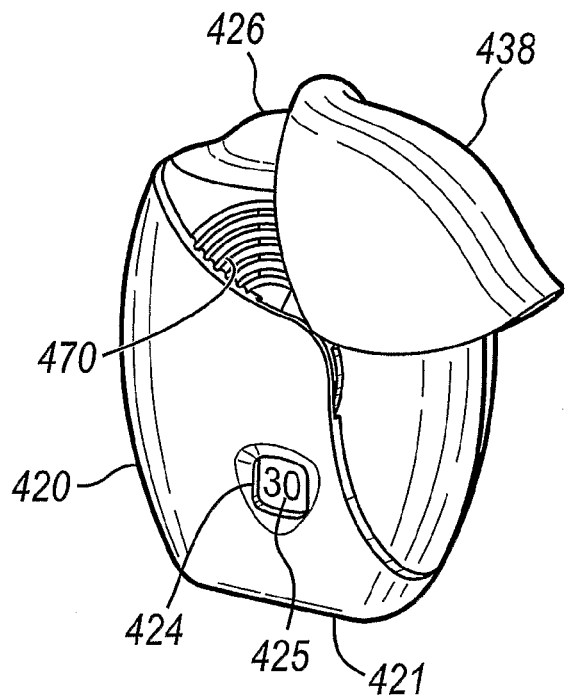
Figure 5B:
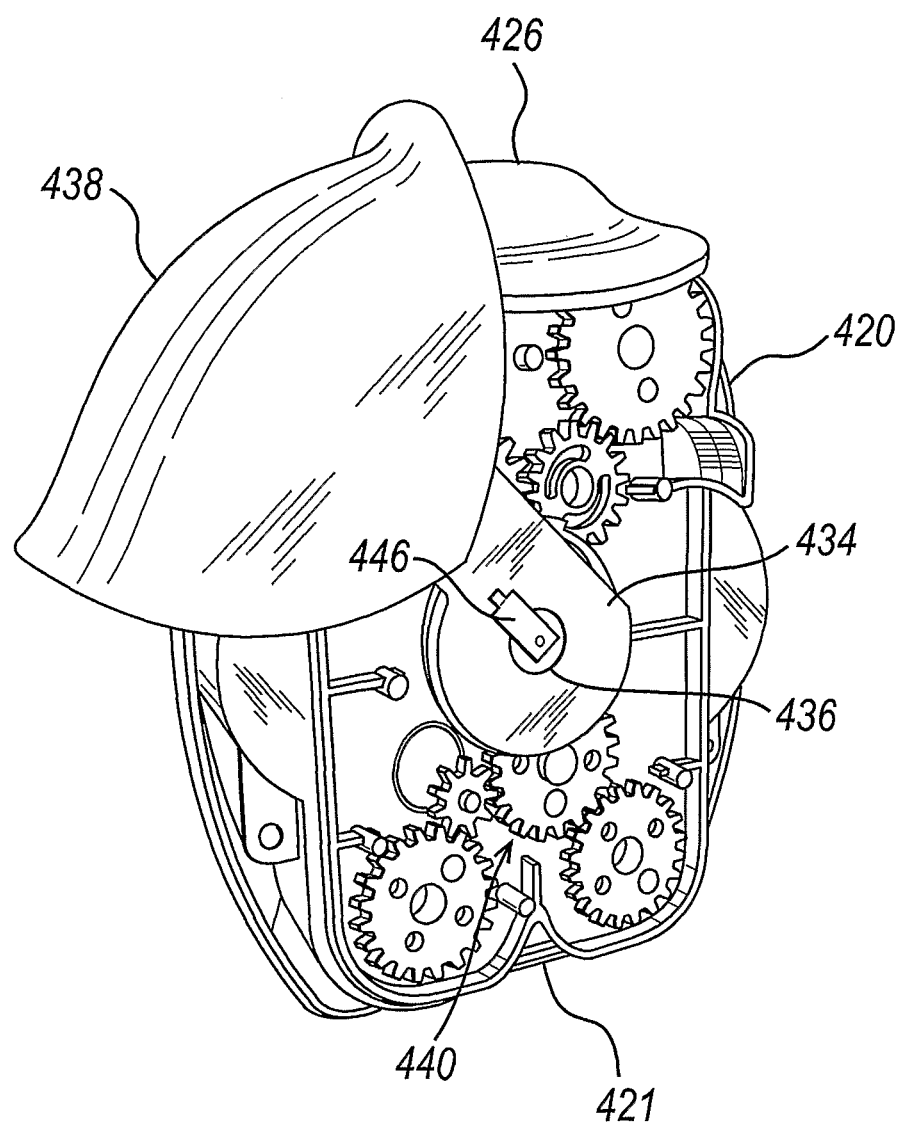

In FIGS. 4b and 5b, the mouthpiece cover 438 has been rotated to a second position, in which the mouthpiece 426 and an air inlet grille 470 are part-uncovered, but in which the gear mechanism 440 and an associated dispensing mechanism, as described in more detail below, is not actuated whereby no medicament dose is made available for inhalation. Additionally, no actuation of the dose counter (not shown) has taken place whereby the count indicia 425 stays the same. The count indicia 425 in this particular embodiment indicates the number of unopened pockets 404a, 404b left on each strip 402a, 402b.

Figure 4C:
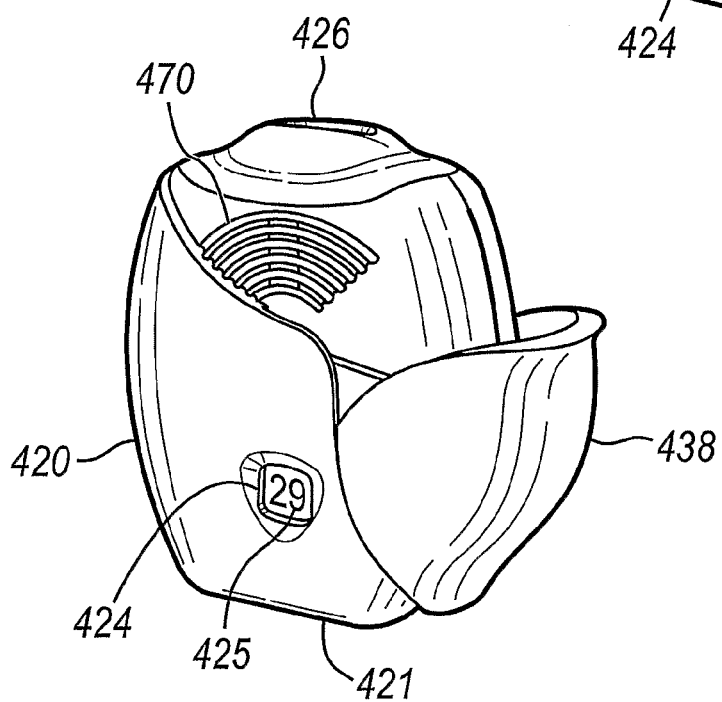

In FIGS. 4c and 5c, the mouthpiece cover 438 has been rotated further to a third position to fully uncover or open the mouthpiece 426 and the air inlet grille 470. Part of the cover 438 extends almost to the base 421 of the housing 420 in this position. As a result of the further movement from the second to third position the gear mechanism (described in more detail with reference to FIGS. 6 and 7a to 7c below) and dispensing mechanism (described in more detail with reference to FIG. 9 below) have been actuated in the dispenser device to make a medicament dose available for inhalation. In other words, the medicament dispenser device is now primed for use. The movement has also resulted in actuation of the dose counter (mechanism not visible) of the medicament dispenser device such as to decrease the dose count indicia 425 by one unit to a new reading of '29'.

After use, the mouthpiece cover 438 is returned to the first position (i.e. as in FIGS. 4a and 5a). This corresponds to the storage ('mouthpiece protected') position of the dispenser device.

Figure 6:
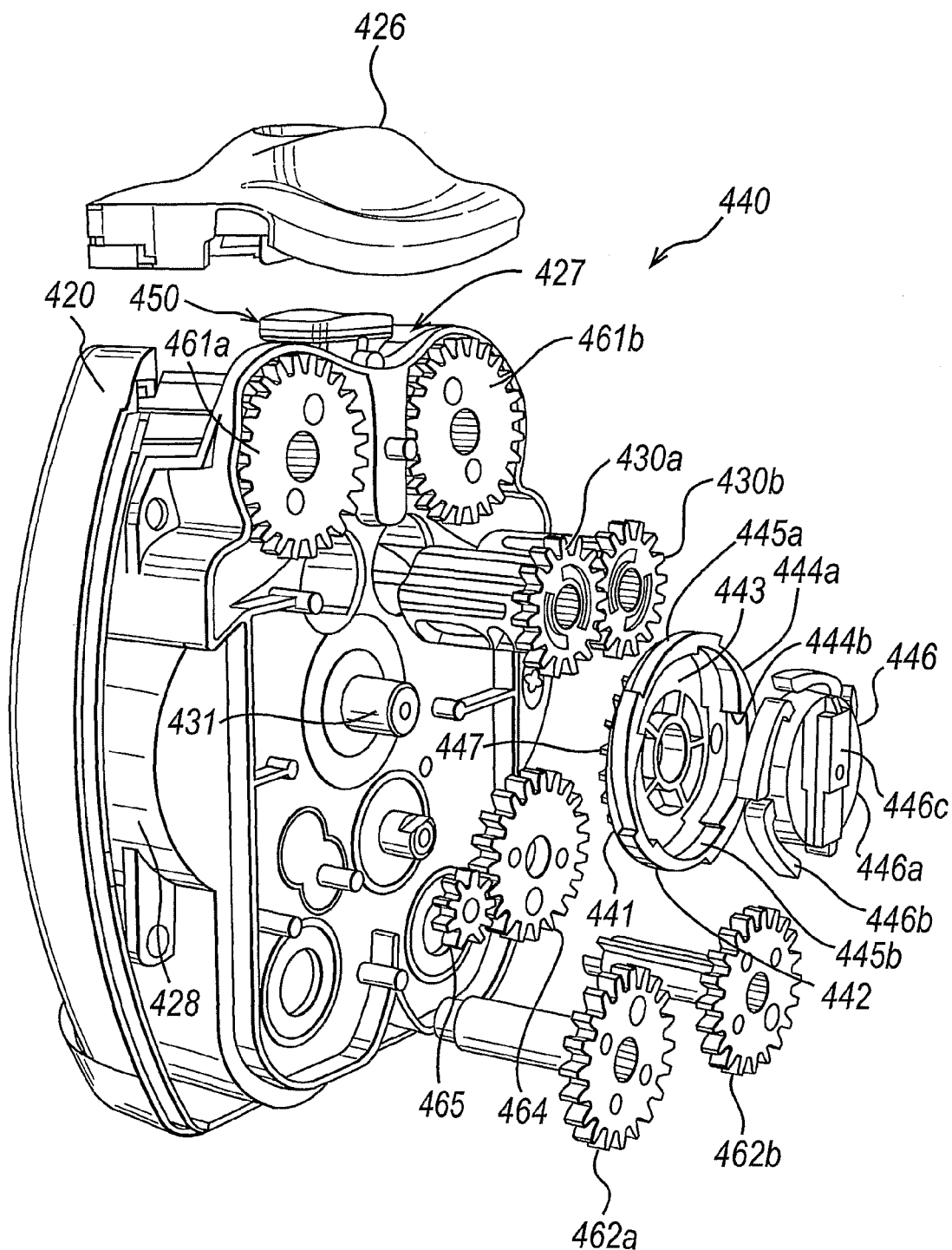

Referring now to FIG. 6, there are shown aspects of the gear mechanism 440. In more detail, housing 420 may be seen to be provided with an internal chassis 428 for outward receipt of the parts of the gear mechanism 440. Within the chassis 428, and as better seen by reference to FIG. 9, there are provided mirror-image ('left' and 'right' hand) dispensing mechanisms 448a, 448b for dispensing medicament. The gear mechanism 440 can be considered to form part of the dispensing mechanisms 448a, 448b.

Figure 9:
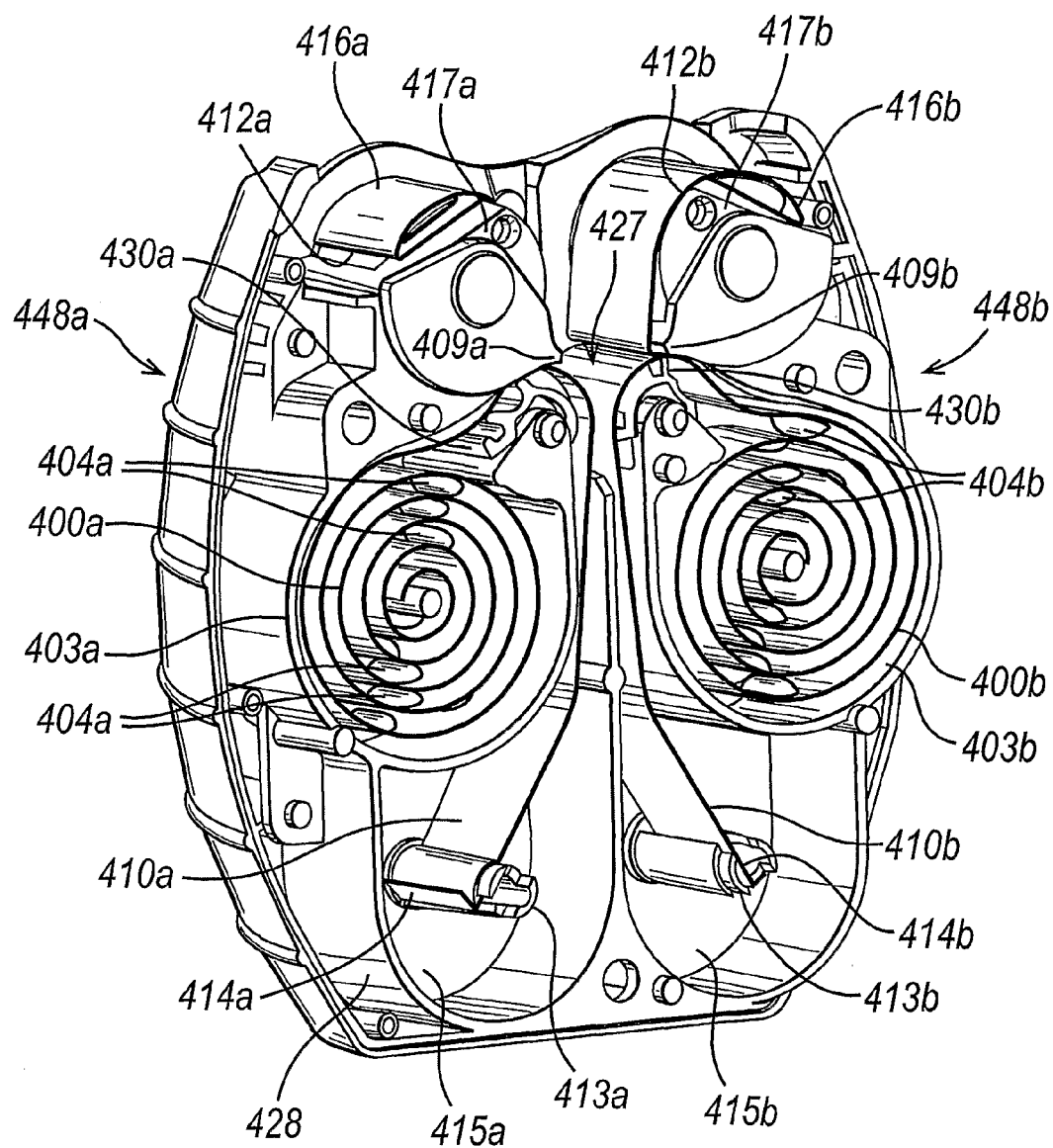

Referring to FIG. 9 in more detail, the first and second medicament-containing blister strips 400a, 400b are positioned within respective left and right chambers 403a, 403b of the chassis 428. Each blister strip 400a, 400b engages in respective multi-pocket index wheel 430a, 430b, of the type used in the DISKUS® inhaler of GlaxoSmithKline, as described and shown in US-A-2005/0126568 (Davies et al)—see FIG. 16, index wheel 416—and in the 'twin strip' inhalation devices of US-A-2005/0154491 (Anderson et al), and successive pockets are thereby guided towards a central opening station 427. At the opening station 427, the lid foil 412a, 412b and base foil 410a, 410b parts of each strip 400a, 400b are peelably separable about beaks 409a, 409b. The resulting empty base foil 410a, 410b coils up in respective base take-up chambers 415a, 415b. Rotatable base take-up spindle 413a, 413b anchors the end 414a, 414b of each respective base foil 410a, 410b in its chamber 415a, 415b. Progressive rotation of each respective base take-up spindle 413a, 413b results in the 'waste' base foil 410a, 410b being wound up therearound into a tight coil. The rotation of each base spindle 413a, 413b is coupled to that of the respective index wheel 430a, 430b.

The used lid foil 412a, 412b feeds over its respective beak 409a, 409b and coils about respective lid take-up wheel 417a, 417b, which also rotate to wind up lid foil 412a, 412b thereon. Each lid take-up wheel 417a, 417b comprises a central hub, to which the ends 416a, 416b of the lid foils 412a, 412b are respectively attached and about which it is wound up, a central spindle (not shown) about which the hub is rotatable and on which is mounted a torsion spring (not visible). This is described in detail in WO-A-2006/018261 (Glaxo Group Limited), in particular the embodiment therein described with reference to FIGS. 1 to 4, which International application, along with the US national phase patent application derived therefrom, is incorporated herein by reference. The function of the torsion spring is to ensure a roughly constant driving tension is provided to each strip 400a, 400b by its lid take-up wheel 417a, 417b over the course of each entire strip length. In particular, each torsion spring acts to compensate for the variation in drive tension associated with the increase in the effective winding diameter of each lid take-up wheel 417a, 417b as used lid foil 412a, 412b gradually becomes wrapped therearound. Thus, uniform indexing of each strip 400a, 400b may be maintained over the entire strip length.

In use, the dispenser device is primed as shown in FIGS. 4a to 4c and 5a to 5c by movement of the cover 438 from the second position (as shown in FIGS. 4b and 5b) to the third position (as shown in FIGS. 4c and 5c) to drivably rotate the index wheels 430a, 430b and lid take-up wheels 417a, 417b to advance each blister strip 400a, 400b, thereby causing the leading unopened pocket thereof to be peeled open. To access the contents of the opened pockets, the patient then breathes in through the mouthpiece 426. As will be described in more detail with reference to FIGS. 10 to 15, this results in negative pressure being transmitted through a manifold 450 to the opened pocket of each strip 400a, 400b at the opening station 427. This in turn results in the medicament powder contained within each of the opened pockets being simultaneously drawn out through the common manifold 450 to the mouthpiece 426 and hence to the patient as an inhaled combination medicament dose.

Referring again to FIG. 6, the gear mechanism 440 may be seen to comprise ratchet gear 442 mounted on drive spindle 431. The ratchet gear 442, like the other gears, is a wheel form having opposed inner and outer faces 441, 443 (relative to the exterior of the dispenser device) and an outer circumferential surface 445a therebetween. The outer face 443 is recessed to define an inner circumferential surface 445b in opposed relation to the outer circumferential surface 445a. As will be seen, the outer and inner circumferential surfaces 445a, 445b are provided with a stepped profile to give respective outer and inner ratchet features 444a, 444b for ratcheted interaction with the ratchet 446, which interaction will be described in more detail with reference to FIGS. 7a to 7c. The ratchet features 444a, 444b are equi-angularly spaced-apart ratchet teeth; in this embodiment there are 5teeth on each circumferential surface 445a, 445b. The teeth 444a on the outer circumferential surface 445a (the 'outer teeth 444a') are offset from the teeth 444b on the inner circumferential surface 445b (the 'inner teeth 444b'). In other words, none of the inner teeth 444b lie on the same radius from the axis of rotation of the gear 442 as the outer teeth 444a.

Figure 7A:
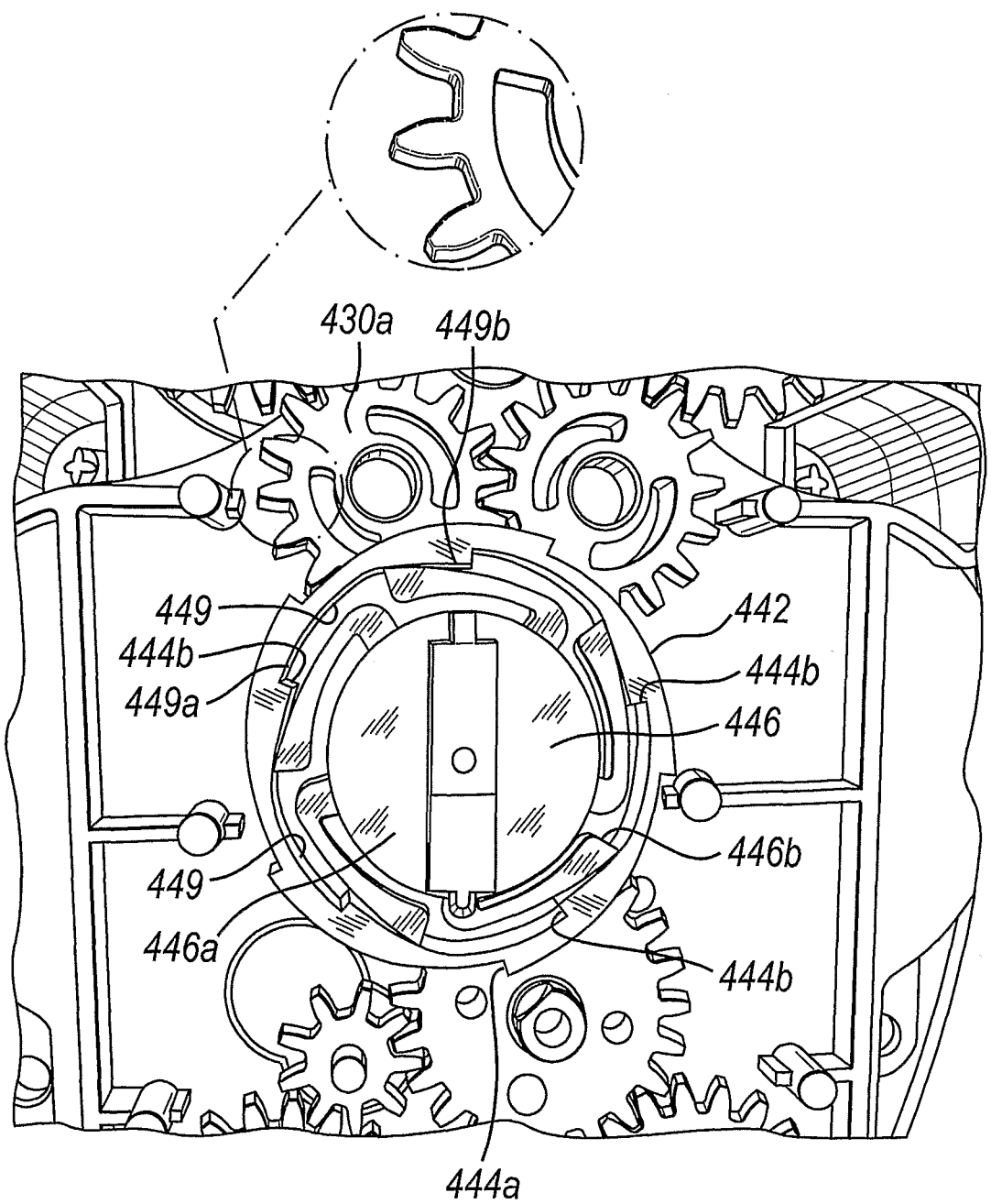

As will be seen from FIG. 7a, the inner circumferential surface 445b comprises surface segments 449 connecting each adjacent pair of inner teeth 444b. Each surface segment 449 consists of first and second sections 449a, 449b which extend inwardly from opposed ends of the segment 449, the first section 449a extending inwardly to the second section 449b from one inner tooth 444b and the second section 449b extending inwardly to the first section 449a from the next adjacent inner tooth 444b. The radius of curvature of the first section 449a is greater than the second section 449b whereby the second section 449b forms a ramp section with respect to the first section 449a.

Referring to FIG. 6, it will be appreciated that the base take-up spindles 413a, 413b and the spindles (not shown) of the lid take-up wheels 417a, 417b are respectively connected to base take-up gears 462a, 462b and lid take-up gears 461a, 461b. The index wheels 430a, 430b are also provided with gears. The inner face 441 of the ratchet gear 442 is provided with drive gear teeth 447 for drive interaction (meshing) with (i) the gear of a first one of the index wheels 430a, and (ii) a first idler gear 464. The gear of the first index wheel 430a meshes with a first one of the lid take-up wheel gears 461a and the gear of the second index wheel 430b, which in turn meshes with the second lid take-up gear 461b. The first idler gear 464 meshes with a first one of the base take-up spindle gears 462b and a second idler gear 465, which in turn meshes with the second base take-up spindle gear 462a. This gear train arrangement provides for indexing of the medicament carriers 400a, 400b and winding on of the base and lid sheets 410a,b, 412a,b on movement of the mouthpiece cover 438 from its second position to its third position.

A more detailed description of a suitable counter mechanism for use in the dispenser device is provided in WO-A-2005/079727 (Glaxo Group Limited) which, along with the U.S. national phase patent application Ser. No. 10/597,551 derived therefrom, is incorporated herein by reference. The base take-up spindle 413b can be used to drive this counter mechanism by engagement with the drive wheel/step-up gear wheel thereof.

Figure 7B:
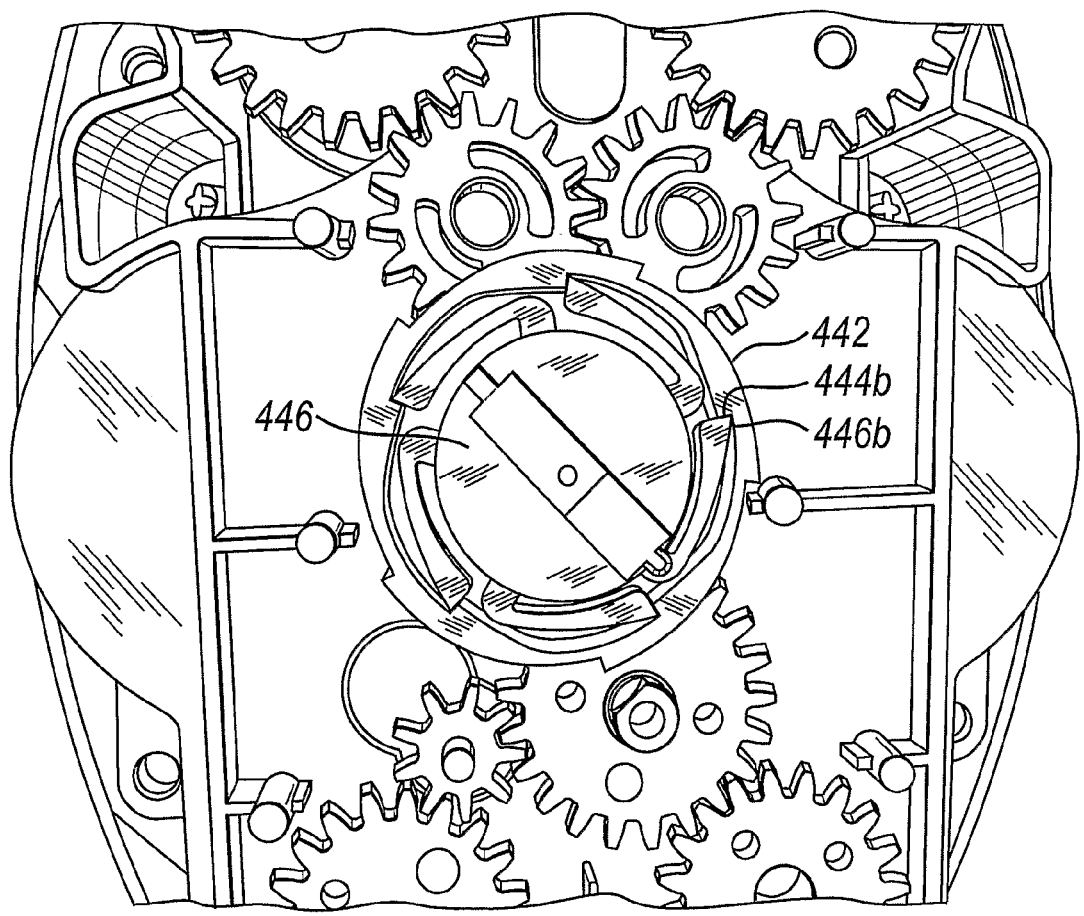
Figure 7C:
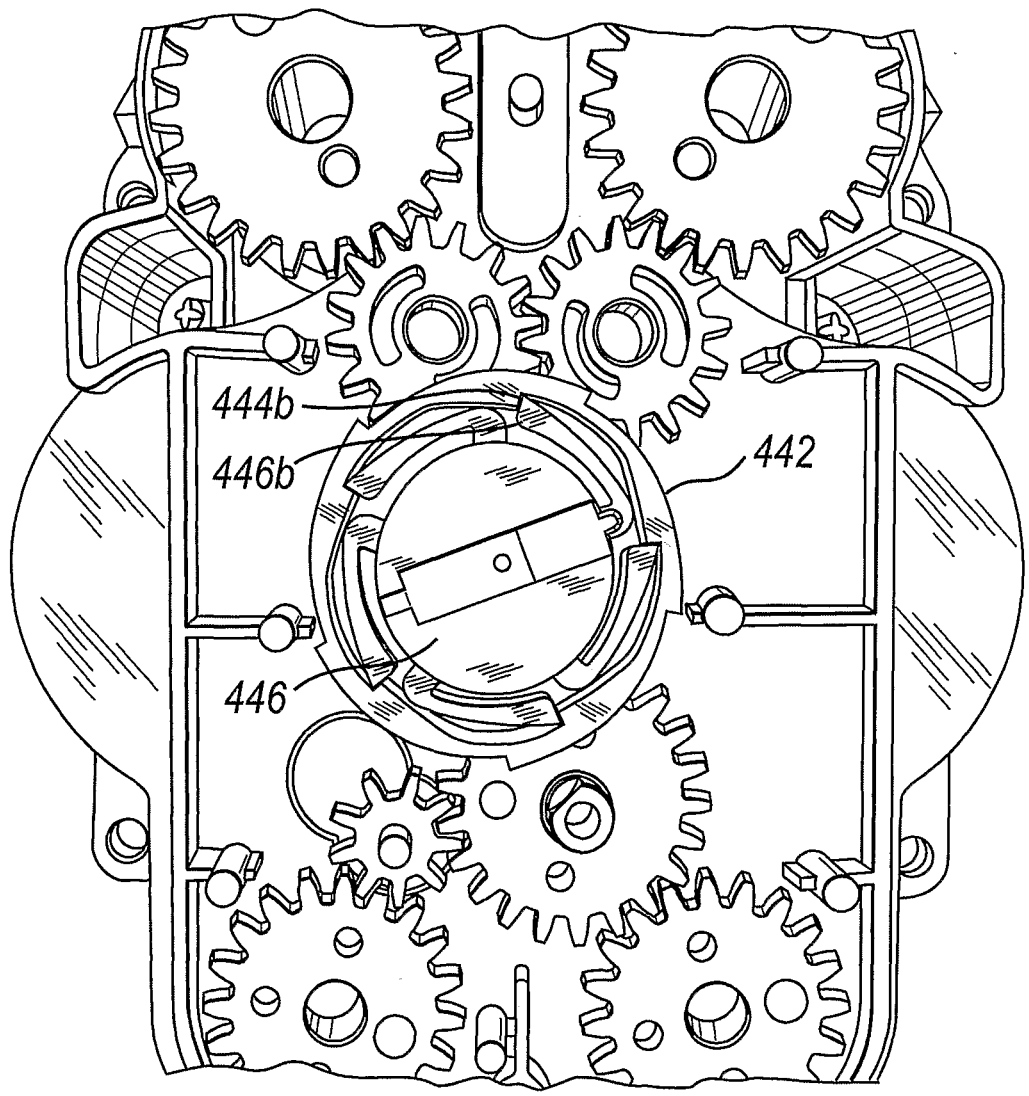
Figure 8:
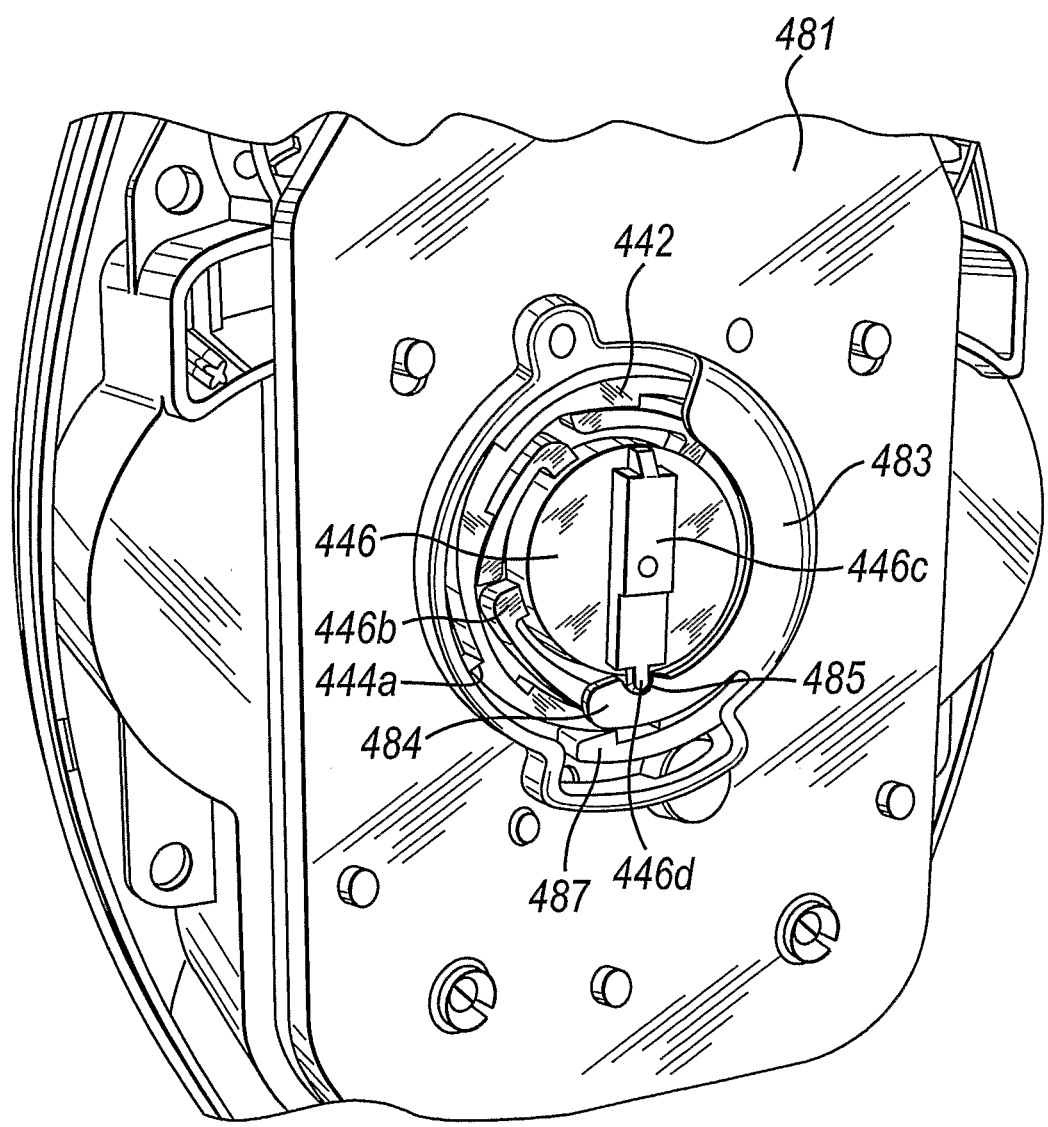

As shown in FIGS. 6 to 8, the ratchet 446 comprises a central hub 446a from the outer circumference of which depend a plurality of equi-angularly spaced-apart, circumferentially-oriented, resilient legs 446b. The ratchet hub 446a further comprises a boss 446c which, as shown in FIG. 5a, fits in the mounting aperture 436 of the mouthpiece cover arm 434 for establishing a direct drive connection between the mouthpiece cover 438 and the ratchet 446 whereby rotary movement of the mouthpiece cover 438 between its first to third positions causes rotary movement of the ratchet 446 in the ratchet gear 442, as will be described in more detail shortly hereinafter. In this particular embodiment, 5 ratchet legs 446b depend from the ratchet hub 446a. In other words, the number of ratchet legs 446b is chosen to match the number of inner teeth 444b of the ratchet gear 442.

Interaction of the ratchet gear 442 with ratchet 446 may be better understood with reference to FIGS. 7a to 7c, which show movement of parts of the gear mechanism 440 of the third medicament dispenser device when prepared for use in sequential steps corresponding to those of FIGS. 4a to 4c.

In the rest position of FIG. 7a (i.e. mouthpiece cover 438 closed), the ratchet 446 is angularly disposed in the ratchet gear 442 so that the inner teeth 444b of ratchet gear 442 are circumferentially spaced from the free ends of the ratchet legs 446b. In the second position of FIG. 7b (i.e. mouthpiece cover 438 partially opened), the ratchet 446 has rotated round in the ratchet gear 442 to slide the ratchet legs 446b over the adjacent surface segments 449 of the inner circumferential surface 445b to engage the inner teeth 444b. It will therefore be appreciated that in this second position, the ratchet gear 442 is ready for movement but has not yet been moved, and hence that the overall gear mechanism 440 and dispensing mechanisms 448a, 448b have not been advanced. In the third position of FIG. 7c (i.e. mouthpiece cover 438 fully opened), both the ratchet 446 and ratchet gear 442 rotate together (by 72° as shown) through inter-engagement of the ratchet legs 446b and the inner teeth 444b such as to advance the overall gear mechanism 440 and dispensing mechanisms 448a, 448b such as to index and advance each medicament carrier 400a, 400b to open a solitary pocket of each and to thereby make the medicament powder contained in each opened pocket available at the manifold 450 at the opening station 427 for simultaneous inhalation by the patient through the opened mouthpiece 426.

Referring to FIG. 8, the dispenser device further comprises an internal retaining plate 481 for covering the gear mechanism 440. The retaining plate 481 is provided with an arcuate shelf 483 which lies over the ratchet gear 442 and the ratchet 446.

One end of the shelf 483 is configured as a resilient finger 484 in which is provided a notch 485. The ratchet 446 includes a protrusion 446d which engages in the notch when the ratchet (and hence the mouthpiece cover 438) is in its first, rest position of FIG. 7a, as shown in FIG. 8. This inter-engagement of the ratchet protrusion 446d and the retaining plate notch 485 acts as a detent to detent the mouthpiece cover 438 in the 'mouthpiece closed' or rest position of FIGS. 4a, 5a, 7a and 8.

The retaining plate 481 yet further comprises a fixed, resilient pawl leg 487 for interaction with the outer teeth 444a of the ratchet gear 442 to form an 'anti-return' feature for the ratchet gear 442. When the mouthpiece cover 438 is opened, to cause rotation of the ratchet 446 and then the ratchet gear 442 once the ratchet legs 446b engage the inner teeth 444b, the pawl leg 487 is not an impediment to the rotary movement of the ratchet gear 442 as the pawl leg 487 rides over the outer teeth 444a due to their orientation and the resilience of the pawl leg 487. However, when the mouthpiece cover 438 is returned to its closed position, in turn rotating the ratchet 446 back to its rest position, the ratchet gear 442 is held against return rotation by engagement of the pawl leg 487 with one of the outer teeth 444a. Accordingly, the reverse rotation of the ratchet 446 on closure of the mouthpiece cover 438 is not transmitted to the gear mechanism 440. Thus, on each occasion the mouthpiece cover 438 is fully opened and closed, the ratchet gear 442 is incremented in one rotary direction only.

When the mouthpiece cover 438 is returned to its first, covering position (FIG. 4a) to rotate the ratchet 446 in the ratchet gear 442 back to its rest position (FIG. 7a), the resilient legs 446b slide back over the inner circumferential surface 445b to be spaced behind different inner teeth 444b ready for next opening of the mouthpiece cover 438.

In FIG. 7a there is shown an enlarged view of one of the gear teeth of index wheel 430a showing the profile thereof. The gear teeth of all of the gears in the gear mechanism are provided with this profile.

In summary, manual movement, by the patient, of the mouthpiece cover 438 from its first position, in which it closes the mouthpiece 426 (e.g. FIG. 4a), to its third position, in which it fully opens the mouthpiece 426 (e.g. FIG. 4c), results in the ratchet 446 driving the gear and dispensing mechanisms 440, 448a, 448b so that each blister strip 402a, 402b is indexed in the dispenser device to cause a single blister pocket 404a, 404b of each strip 402a, 402b to be opened and presented to the manifold 450 at the opening station 427 ready for the patient to simultaneously inhale the powder contents of each newly opened pocket 404a, 404b and thus receive a fixed dose of a combination of different drug actives. After the patient has inhaled the powder contents of each newly opened pocket, the patient manually returns the mouthpiece cover 438 to its first position ready for next use. Upon next use, the next closed pocket 404a, 404b on each strip 402a, 402b will be opened and indexed to the manifold 450 to enable the patient to inhale the next fixed dose of the drug combination. This opening and closing cycle then continues, in accordance with the prescribing regime for the drug combination (e.g. once a day, twice a day etc.), until all of the pockets 404a, 404b are emptied, as will be evidenced by the count indicia 425. As described above, movement of the mouthpiece cover 438 from its first position to the intermediate second position (e.g. FIG. 4b) does not result in indexing/opening of the blister pockets 404a, 404b.

A more detailed description of the manifold 450 of the third medicament dispenser device now follows with reference to FIGS. 10 to 15.

Figure 10:
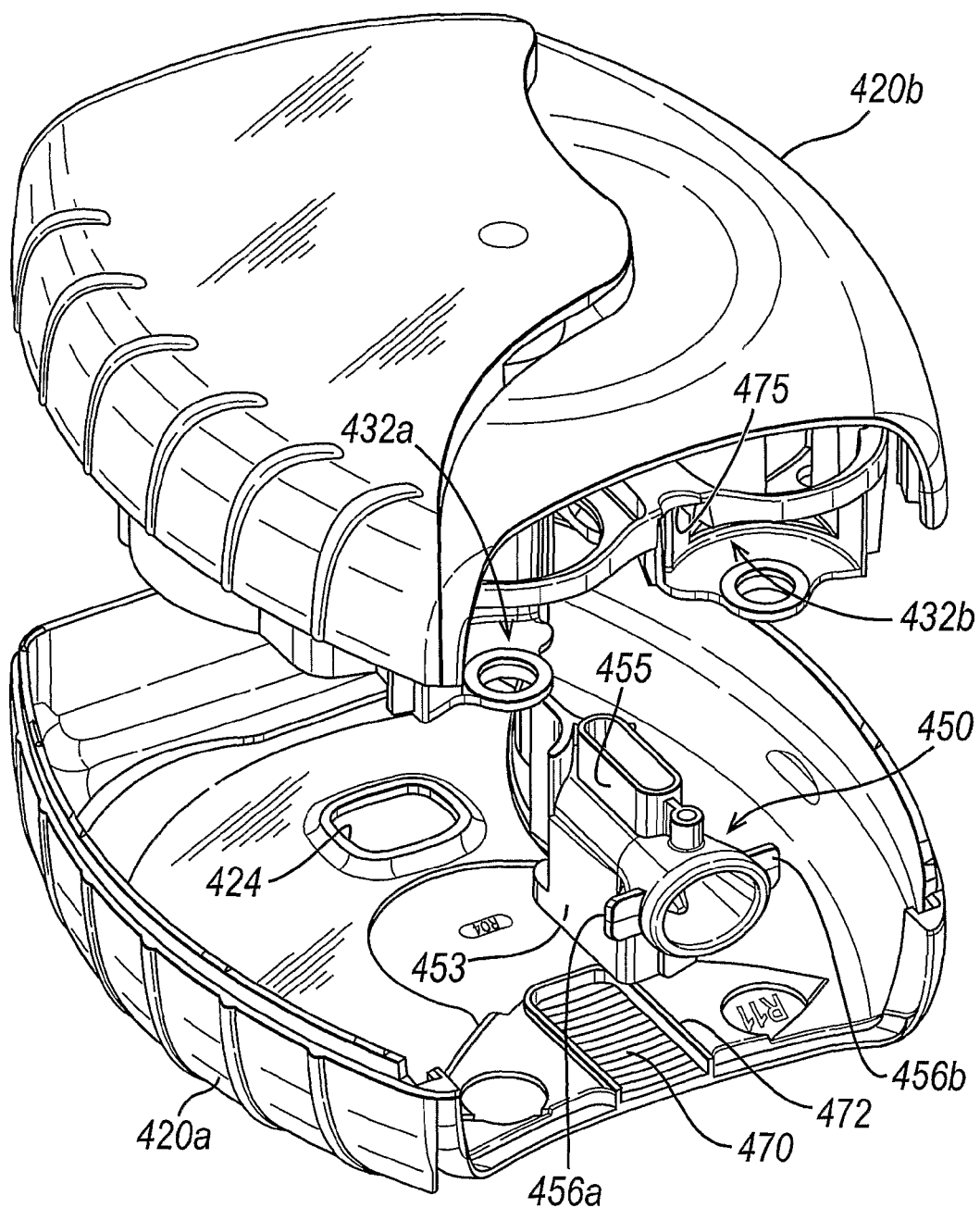
Figure 11:
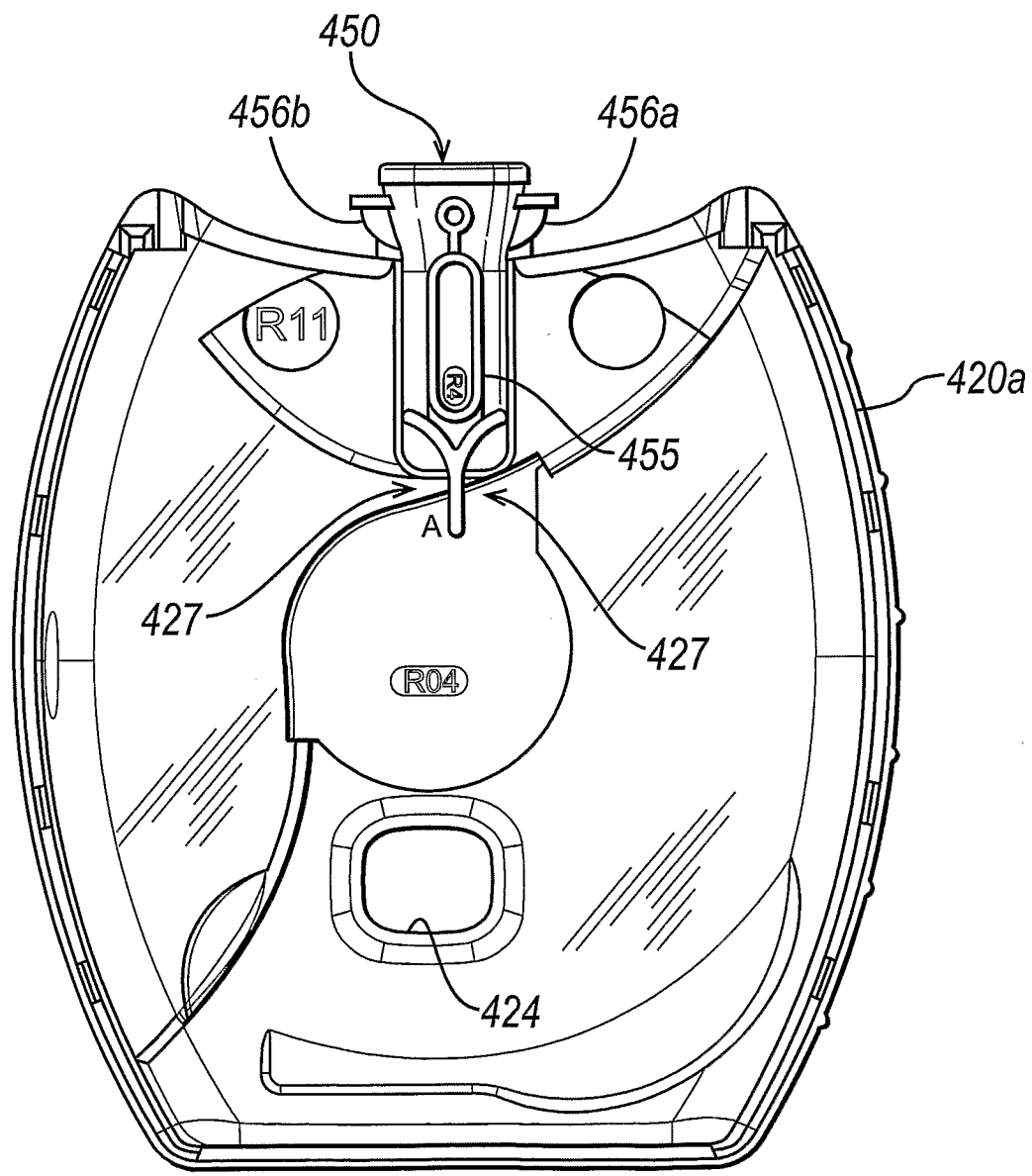

FIG. 10 shows the third medicament dispenser device absent its mouthpiece 426. In more detail, the housing 420 comprises mating first 420a and second 420b shell cover parts, which in combination act to house the dispenser device mechanisms thereof. The manifold 450 is received by the first shell cover part 420a such that a lip defining an inlet 453 to a chimney 452 is received within an inner wall 472 of the first shell cover part 420a which defines the air inlet grille 470.

As described above, and as shown in FIGS. 4a to 4c, the air inlet grille 470 in the first shell cover part 420a is covered by the mouthpiece cover 438 when in its first or closed position (FIG. 4a), part-uncovered when the mouthpiece cover 438 is in its second or part-opened position (FIG. 4b) and fully revealed when the mouthpiece cover 438 is in its third or open position (FIG. 4c).

Figure 12:
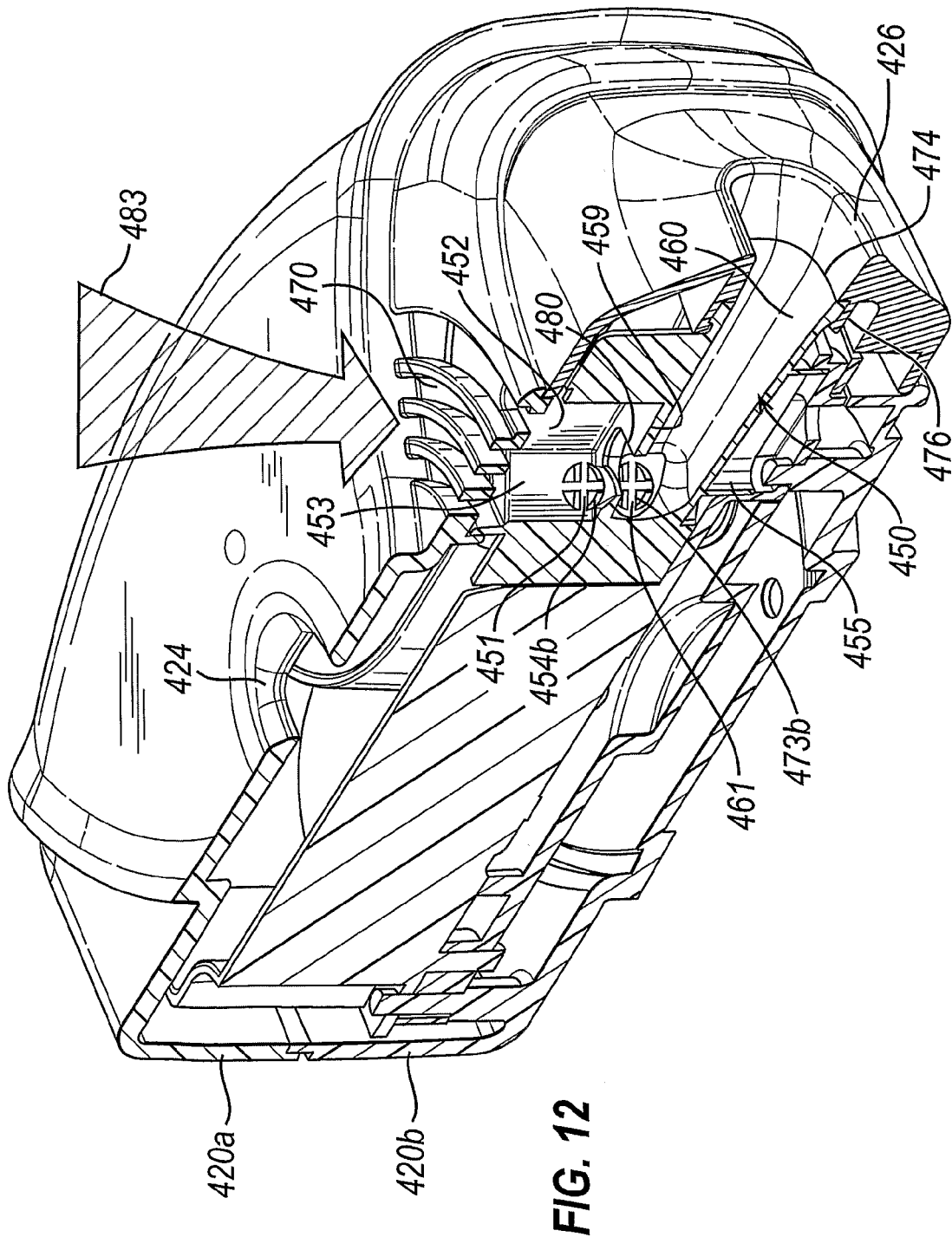

In use, the air inlet grille 470 allows air to pass from outside the third medicament dispenser device into the manifold 450 via the chimney inlet 453 to the chimney 452 in response to inhalation by the patient through the mouthpiece 426, as indicated schematically by arrow 483 in FIG. 12. Notably, this air inlet grille 470 provides the sole intended point of entry of air from the outside into the medicament dispenser device upon patient inhalation at the mouthpiece 426. More particularly, the air inlet grille 470 provides the sole entry point for air outside the dispenser device to pass into the manifold 450 upon patient inhalation on the mouthpiece 426.

The manifold 450 is also received by second shell cover part 420b such that its protruding foot 455 sits within the manifold-receiving cavity 475 thereof. The manifold 450 is provided with a pair of wings 456a, 456b which are assembly features which enable the manifold 450 to be pushed onto the mouthpiece 426.

Figure 13:
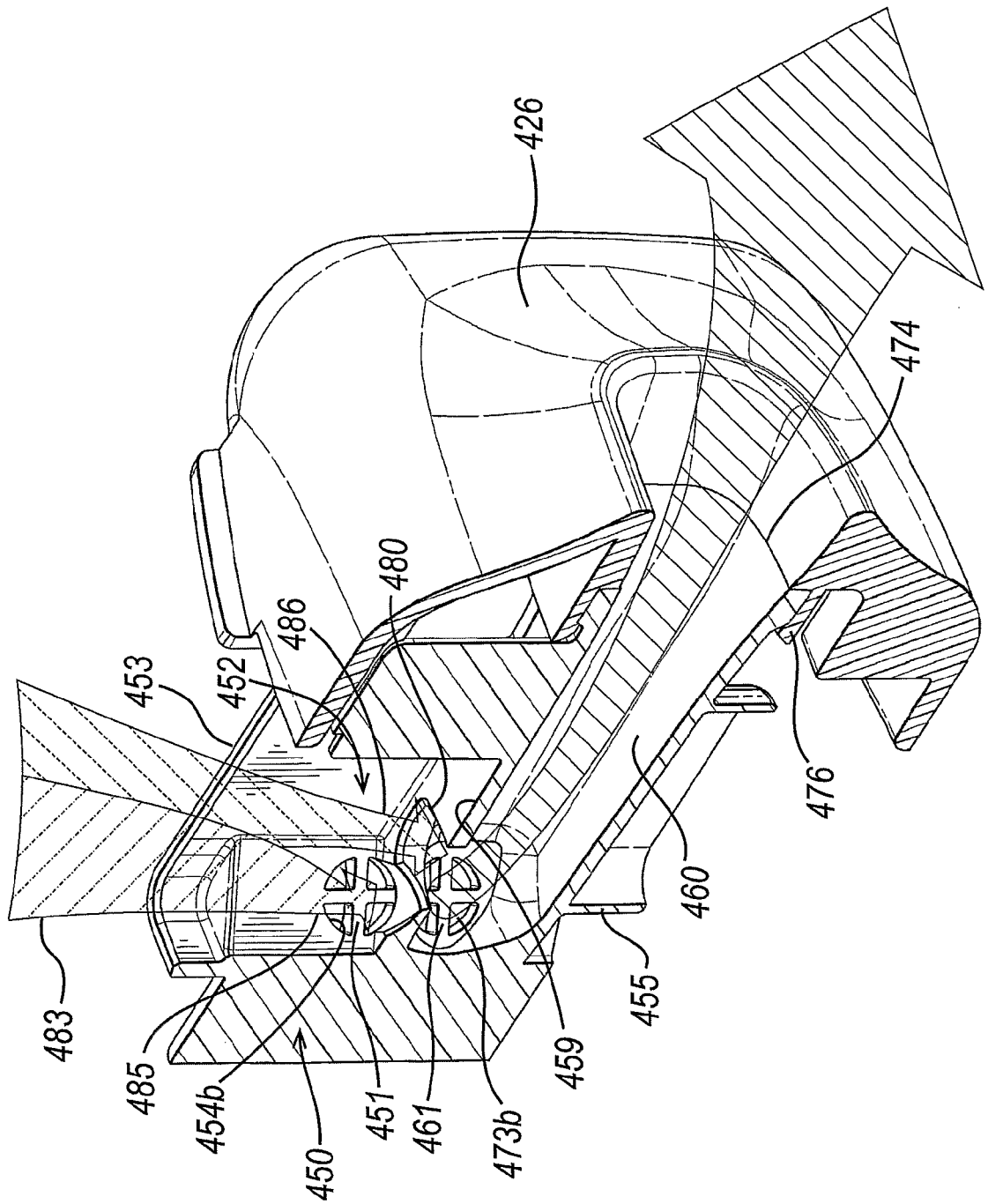
Figure 14A:
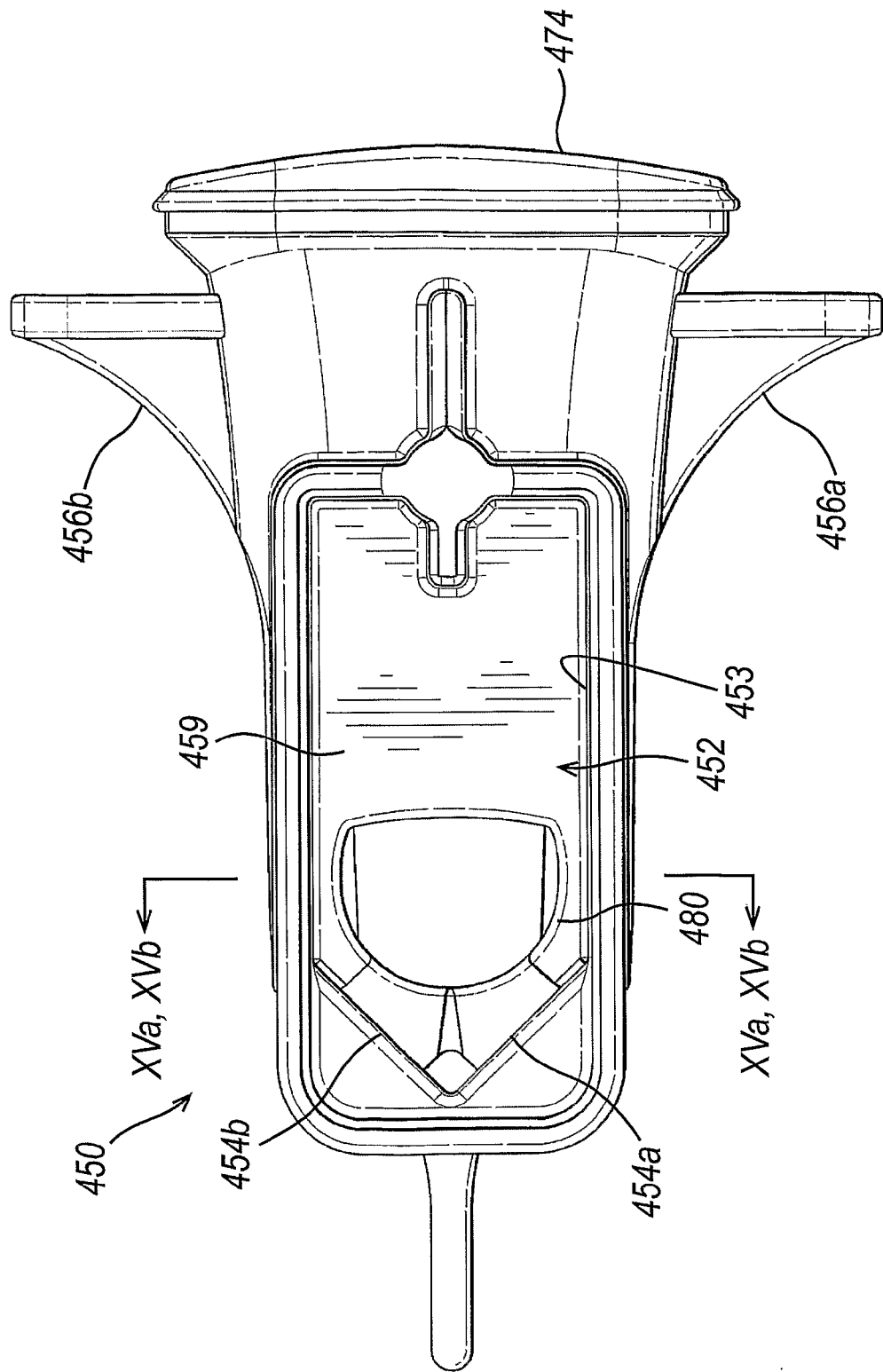
Figure 14B:
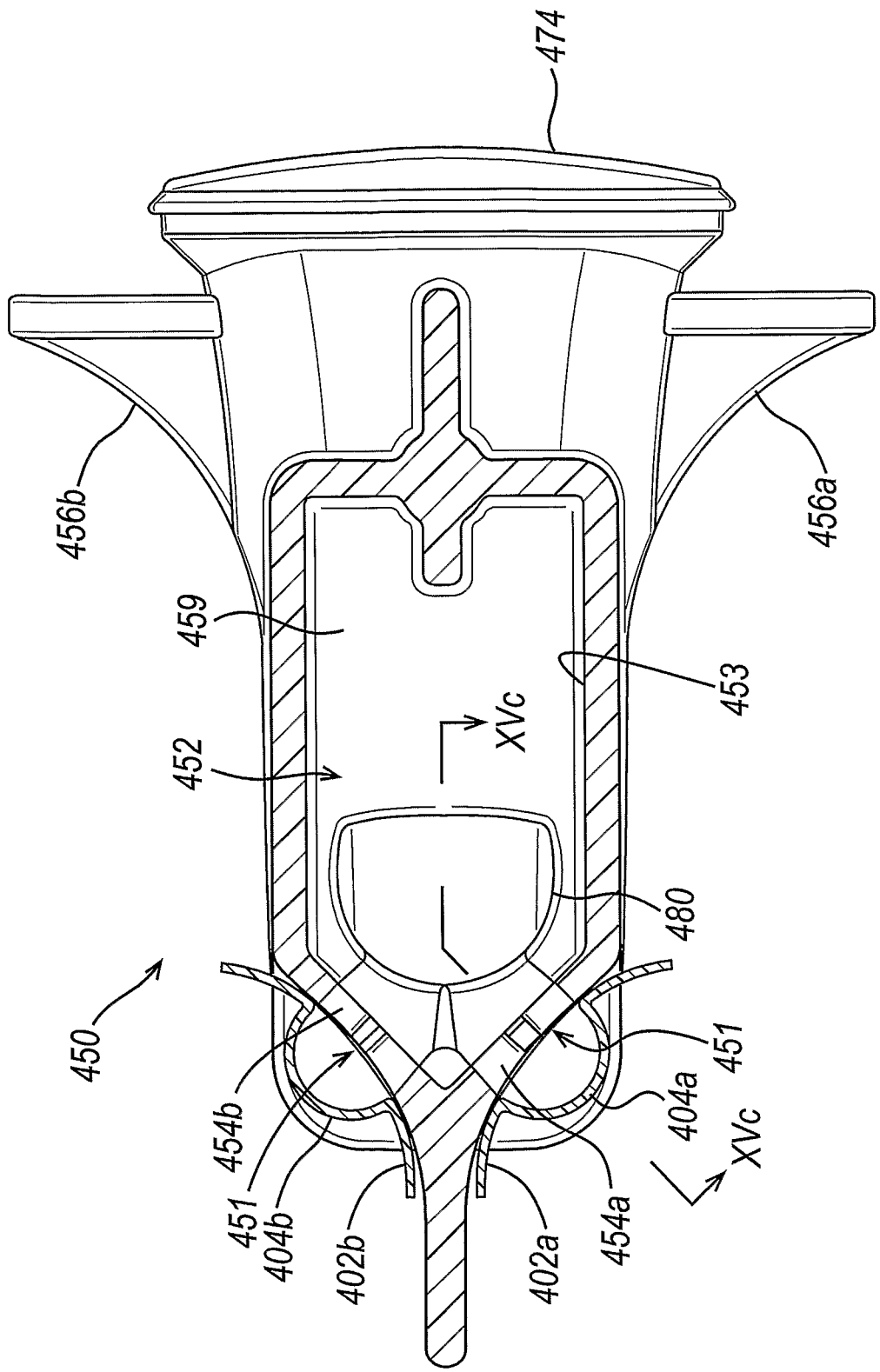

As may also be seen by reference to FIGS. 12 to 15, the manifold 450 has a particular inner structure in which chimney 452 locates above a chamber 460 and partly shares a common wall 459 therewith, which common wall 459 forms the bottom wall of the chimney 452 and part of the top wall of the chamber 460. The terms "above", "bottom" and "top" are only used to describe the relative positioning of features in the manifold 450 in the orientation that the manifold 450 is shown in FIGS. 12 and 13.

The chimney 452 has the chimney inlet 453 and a pair of chimney exits 454a, 454b. In use, the chimney 452 directs inward airflow (as exclusively received through the air inlet grille 470 on patient inhalation at the mouthpiece 426) from the chimney inlet 453 to the pair of chimney exits 454a, 454b. The chamber 460 has a pair of chamber inlets 473a, 473b and a chamber exit 474. The pair of chimney exits 454a, 454b and pair of chamber inlets 473a, 473b are both defined by a pair of circular holes, in this particular embodiment of diameter about 3 mm, and each hole is provided with a respective cruciform 451, 461. Each chimney exit 454a, 454b is paired with one of the chamber inlets 473a, 473b by positioning them adjacent to one another. The mouthpiece 426 is provided to the chamber exit 474 and snap-mounts thereto via snap-mounting feature 476.

As detailed hereinabove, when the mouthpiece cover 438 is fully opened to its third position, the gear and dispensing mechanisms 440, 448a, 448b are actuated to cause each blister strip 400a, 400b to be advanced and a single pocket 404a, 404b of each strip to be peeled open. As will be understood from FIGS. 14b and 15c, the peeled open blister pocket 404a, 404b of each strip 400a, 400b lies adjacent a respective one of the pairs of chimney exits 454a, 454b and chamber inlets 473a, 473b.

Specifically, the open blister pocket 404a of the first blister strip 402a locates adjacent the first chimney exit 454a and the first chamber inlet 473a (as shown in FIG. 15c) and the open blister pocket 404b of the second blister strip 402b likewise locates adjacent the other chimney exit 454b and chamber inlet 473b. As described previously with reference to FIG. 1, the blister pockets 404a, 404b are elongate, extending sideways relative to the longitudinal axis of the strip 402a, 402b. The pockets 404a, 404b can therefore be considered to have first and second sides on opposing sides of the strip longitudinal axis. When the open pockets 404a, 404b are presented to the manifold 450 at the opening station 427, the pockets 404a, 404b are oriented so that the sideways orientation thereof is aligned to the direction between the respective chimney exits 454a,b and chamber inlets 473a,b. Thus, as shown in FIG. 15c, the chimney exits 454a, b and the chamber exits 473a, 473b lie over the different sides of the pockets 404a, 404b, whereby, in use, the air flows through the pockets 404a, 404b in the sideways orientation thereof; i.e. sideways relative to the longitudinal axis (or length direction) of the strip 402a, 402b.

Figure 15A:
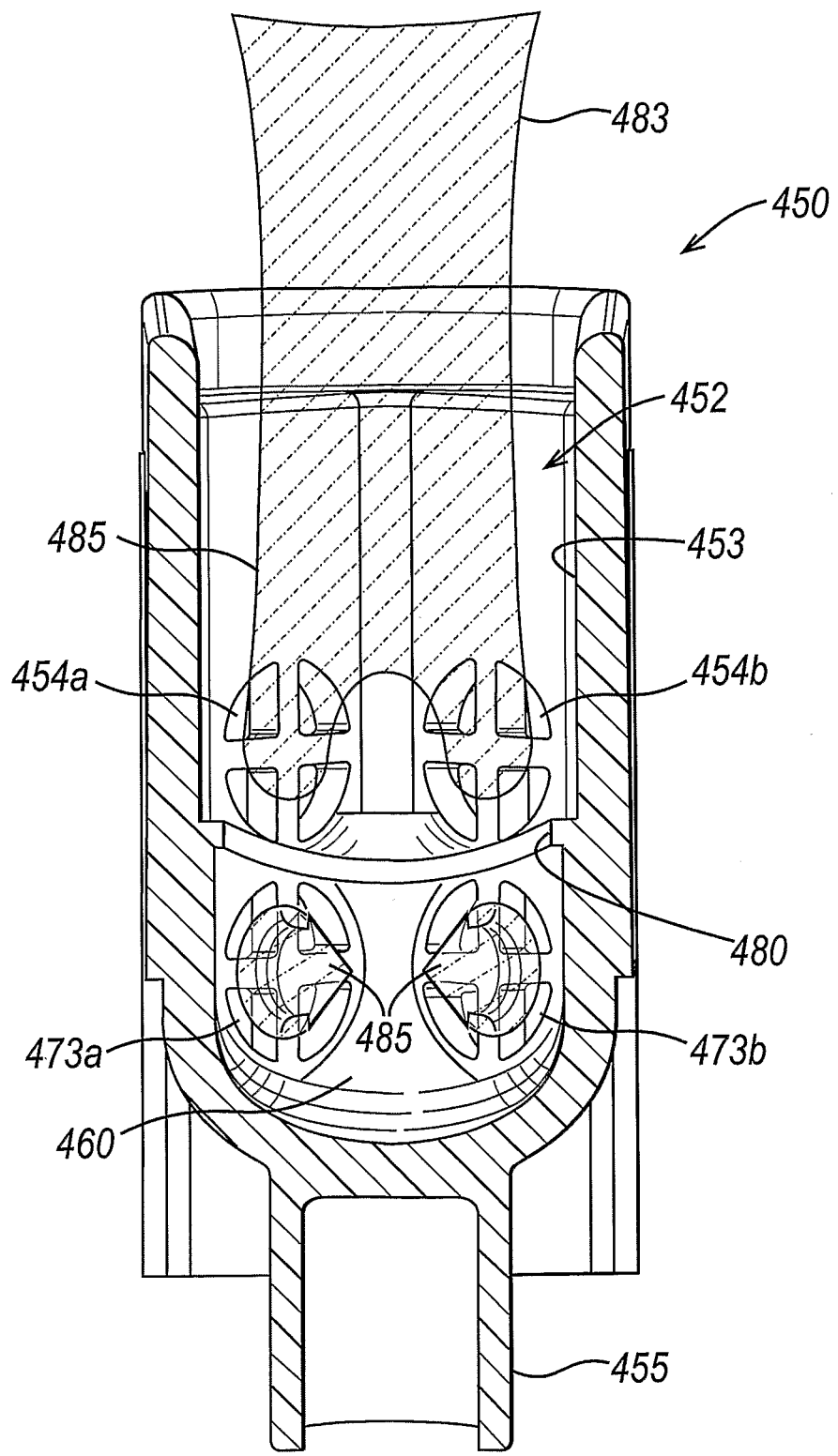

As shown in FIGS. 12, 13 and 15, when a patient inhales at the mouthpiece 426, an airstream 483 flows from outside of the dispenser device into the manifold 450 solely through the air inlet grille 470 into the chimney 452 via the chimney inlet 453, which is in juxtaposed relation with the air inlet grille 470. As graphically represented in FIGS. 13, 15a and 15c, first (or primary) portions 485 of this airstream 483 flow into the opened blister pocket 404a, 404b of each strip 400a, 400b at the opening station 427 via the respective chimney exits 454a, 454b, thereby entraining the medicament powder contained in the pockets in the airstream, and thence out of the pockets 404a, 404b into the chamber 460 via chamber inlets 473a, 473b. The airstream with entrained medicament powder then flows out of the mouthpiece 426 into the patient's respiratory tract.

As shown in FIGS. 12 to 15, a single D-shaped bleed hole 480 is provided to the wall 459 which separates the chimney 452 from the chamber 460. The D-shaped bleed hole 480 locates adjacent to both the chimney exits 454a, 454b and the chamber inlets 473a, 473b. As graphically represented in FIGS. 13, 15b and 15c, in use, the bleed hole 480 acts such as to direct a second portion 486 of the airstream 483 (the "bleed portion") from the chimney 452 directly into the chamber 460 to disruptively impact the first portions 485 of the airstream 483 that transport the entrained medicament powder into the chamber 460 and thereby break up any powder agglomerate components thereof.

Figure 15B:
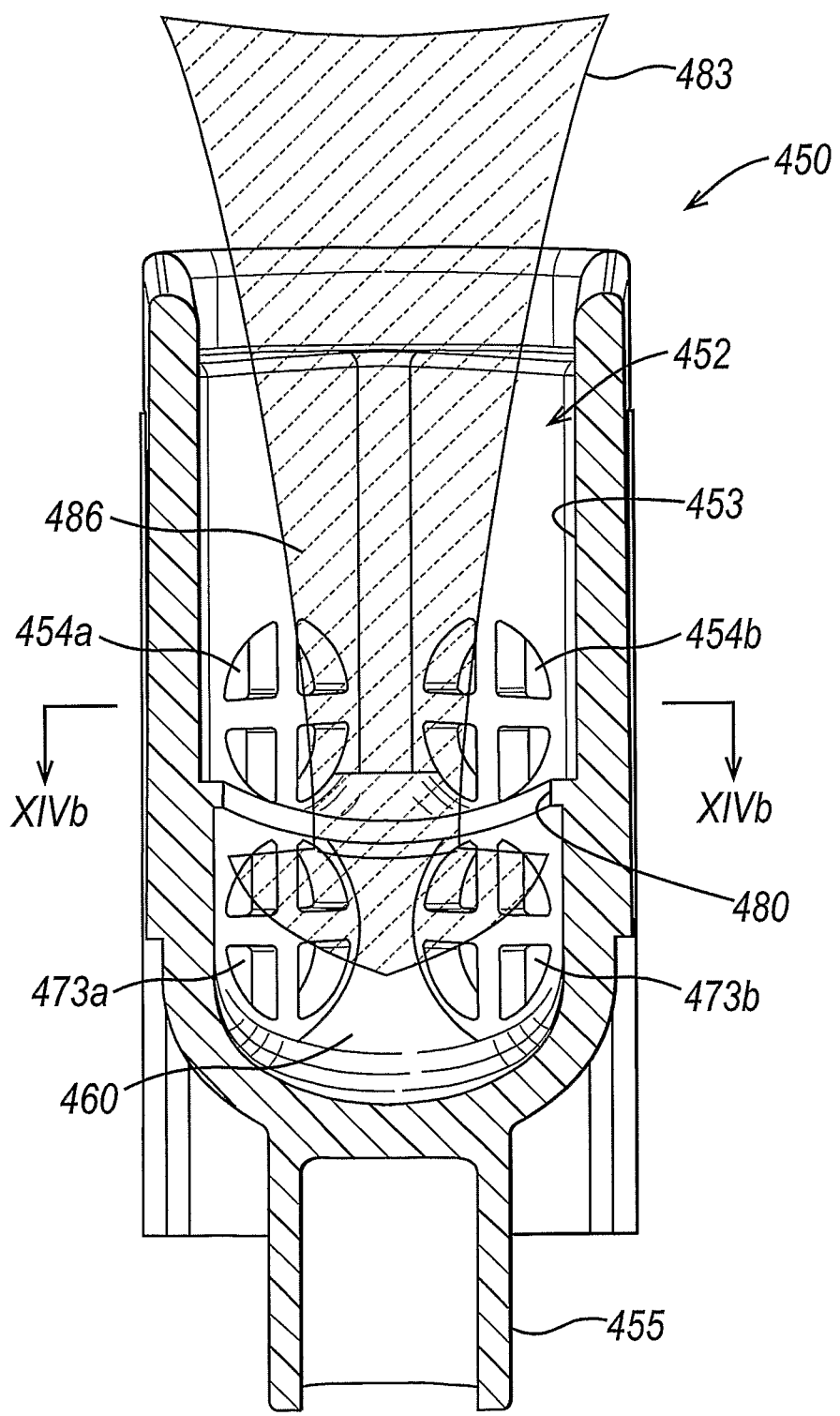

It is to be noted that FIGS. 15a and 15b only selectively show the flow paths of the first 485 and second 486 portions of the airstream 483 for ease of illustration. As the skilled person will appreciate, the first and second portions 485, 486 are created concurrently in the manifold 450 upon patient inhalation at the mouthpiece 426, as indicated in FIGS. 13 and 15c.

FIGS. 16 and 17 shows a second manifold 550 for the third medicament dispenser device that is a variation of (and alternative to) the manifold 450 with 'D-hole' type bleed hole 480. Those features in the second manifold 550 which correspond to features in the first manifold 450 are designated with like reference numerals.

It will be appreciated that the overall shape and form of this second manifold 550 corresponds to that of the 'D-hole' manifold 450 such that one may be readily substituted for the other in the third medicament dispenser device. However, instead of the 'D-hole' type bleed hole 480, the second manifold 550 has two elongate slot form bleed holes 580a, 580b provided to the wall 559, which separates the chimney 552 from the chamber 560.

Figure 17A:
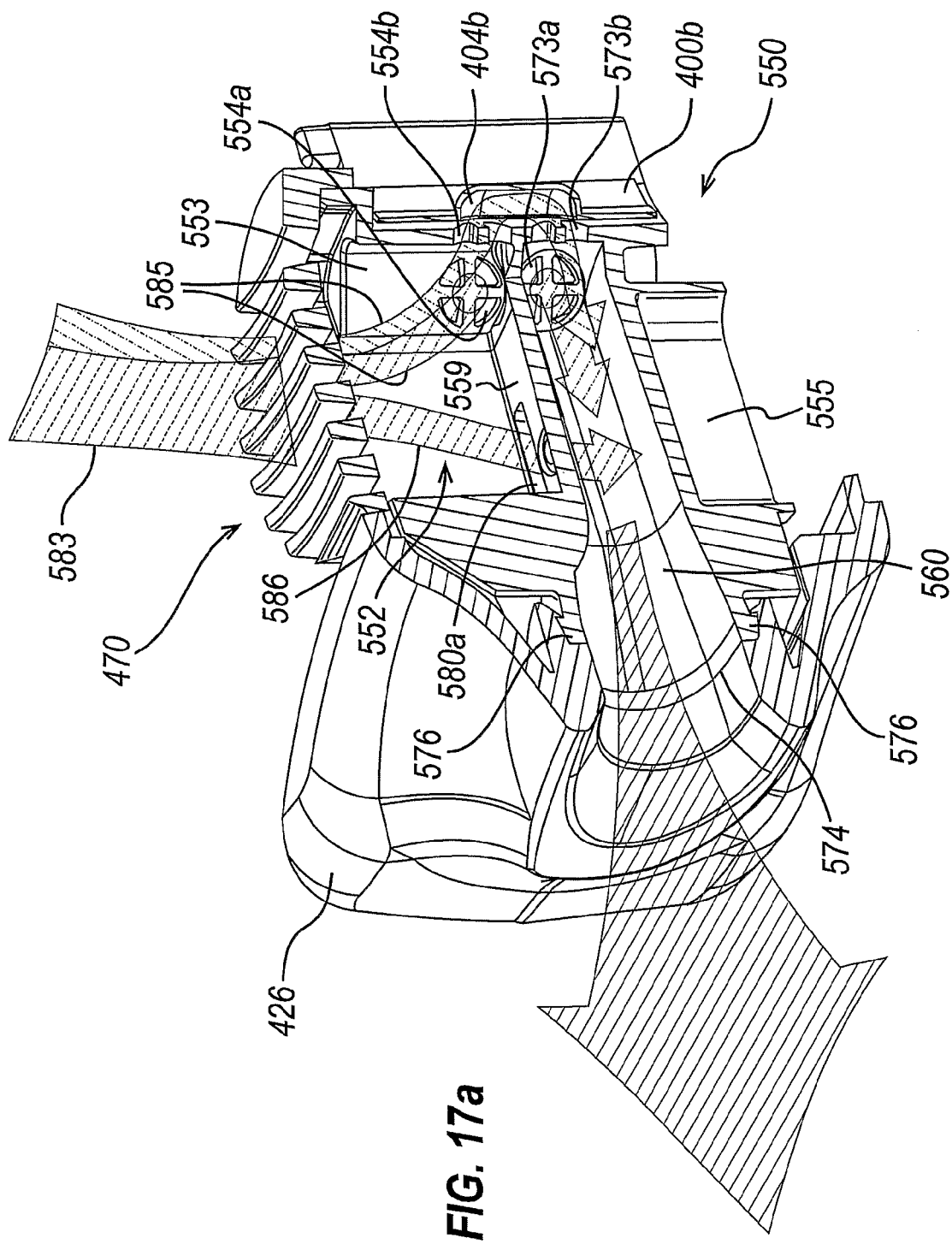

In more detail, second manifold 550 has an inner structure in which chimney 552 locates above chamber 560 and partly shares a wall 559 therewith, which wall 559 forms the bottom wall of the chimney 552 and part of the top wall of the chamber 560. The terms "above", "bottom" and "top" are only used to describe the relative positioning of features in the manifold 550 in the orientation that the manifold 550 is shown in FIG. 17a. Wings 556a, 556b are provided to the manifold as before.

The chimney 552 has a chimney inlet 553 and dual chimney exits 554a, 554b. In use, the chimney 552 directs inward airflow 583 (again, as exclusively received through the air inlet grille 470 as shown in FIG. 17a) from the chimney inlet 553 to the chimney exits 554a, 554b. The chamber 560 has dual chamber inlets 573a, 573b and a chamber exit 564. The chimney exits 554a, 554b and chamber inlets 573a, 573b are both defined by circular holes of diameter about 3 mm, and each is provided with a respective cruciform feature 551, 561.

Figure 17B:
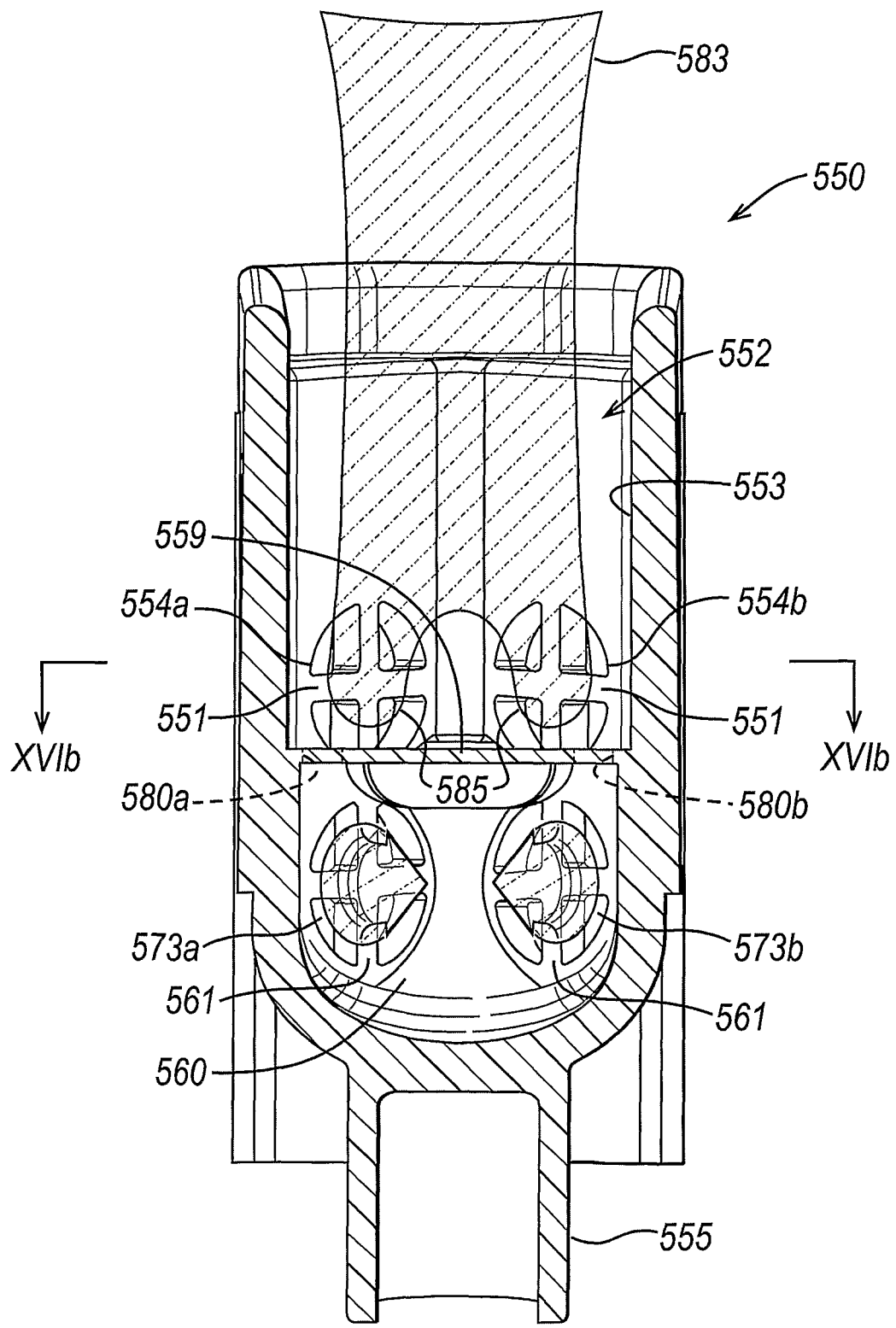

As shown in FIGS. 17a and 17b, the chimney exits 554a, 554b and chamber inlets 573a, 573b are positioned to be adjacent to each other such that when an open blister pocket 404a, 404b (see FIGS. 16b and 17a) lies adjacent thereto at an opening station 427 (e.g. FIG. 11), first portions 585 of the inward airflow 583 are directed via the open pockets 404a, 404b from the chimney exits 554a, 554b to the chamber inlets 573a, 573b and into the chamber 560. This airflow at the open blister pockets 404a, 404b entrains the powder contents of the respective pockets 404a, 404b and enables the transport thereof in the inhalation airflow 583 from the chamber inlets 573a, 573b to the chamber outlet 564, and thence to the inhaling patient via the mouthpiece 426.

Elongate slot form bleed holes 580a, 580b are provided to the wall 559, which separates the chimney 552 from the chamber 560. The elongate slot form bleed holes 580a, 580b locate distal from both the chimney exits 554a, 554b and chamber inlets 573a, 573b. As graphically represented in FIGS. 17a and 17c, in use, the bleed holes 580a, 580b act such as to direct second portions 586 of the airflow 583 (the "bleed portions") from the chimney 552 directly into the chamber 560 to disruptively impact the first portions 585 of the airflow 583 that transport the entrained medicament powder and thereby break up any powder agglomerate components thereof.

Figure 16A:
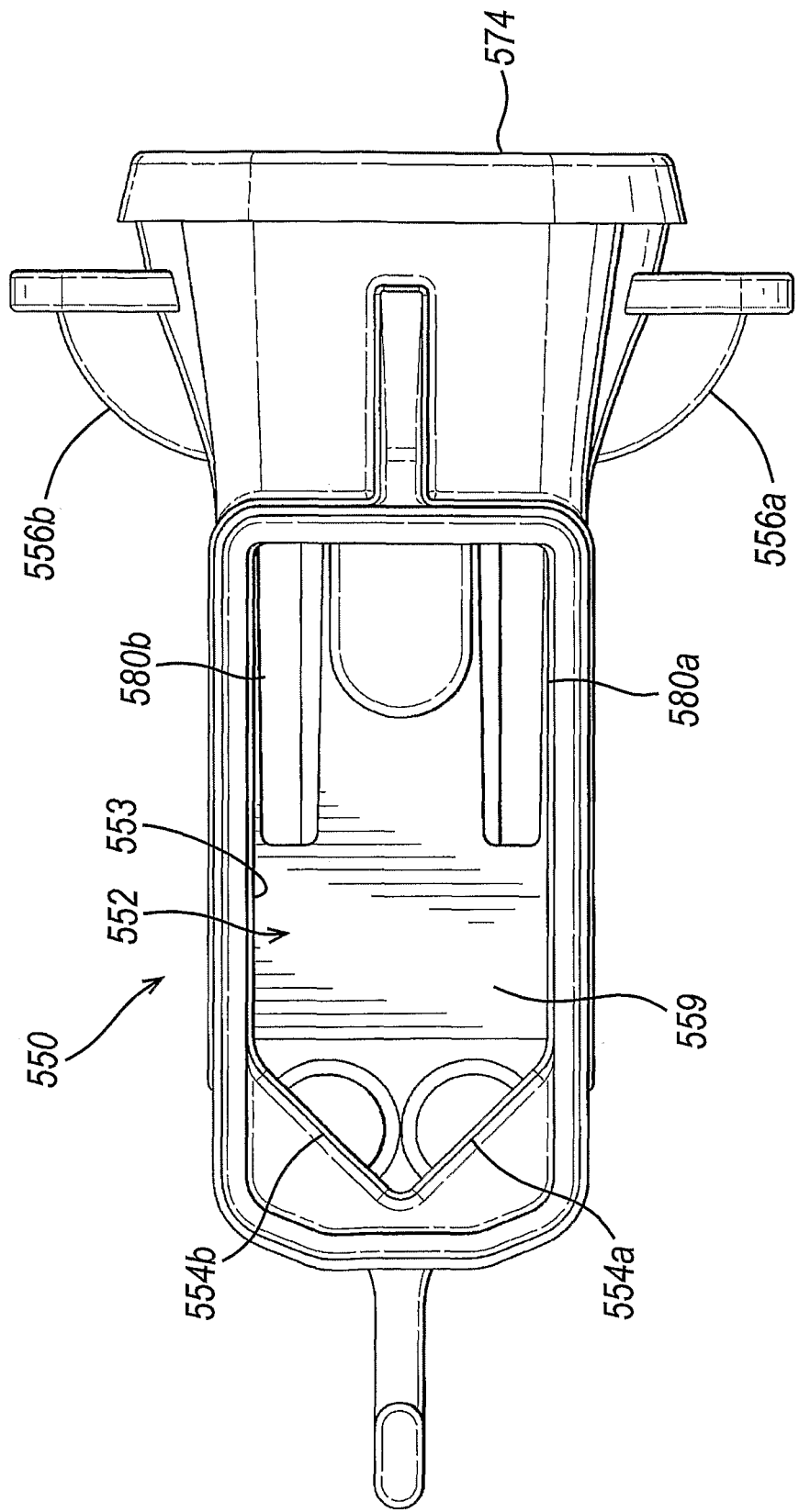
Figure 16B:
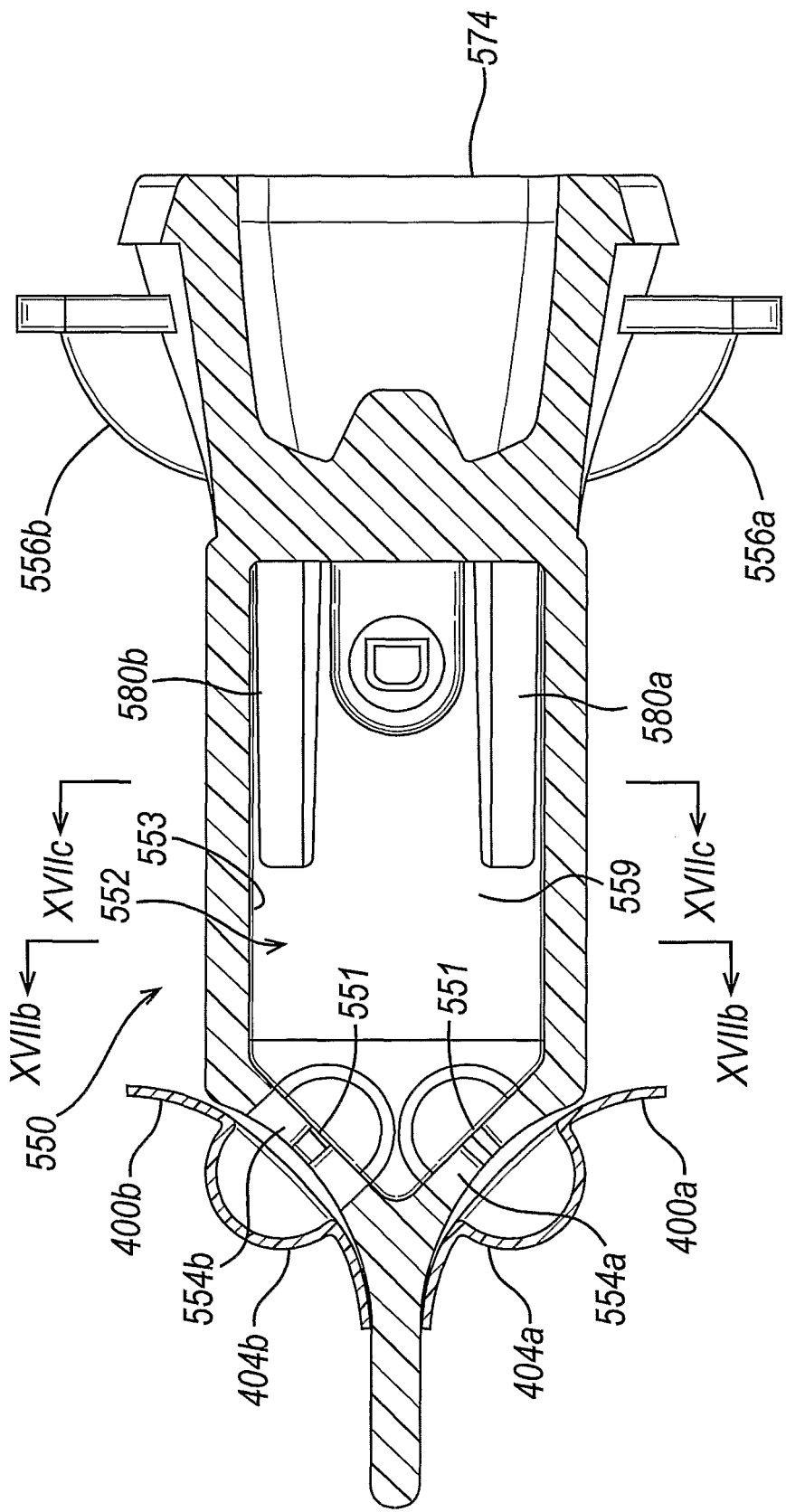

Referring to FIG. 16a, each bleed hole 580a, 580b has a width at its first end nearest the chamber exit 574 of 1.32 mm (±0.15 mm), a width at the opposite second end nearest the chimney exits 554a, 554b of 1.11 mm (±0.15 mm), and a length from the first end to the second end of 6.465 mm (±0.1 mm). The cross-sectional area of each bleed hole 580a, 580b is 7.8 mm$^2$. The bleed holes 580a, 580b therefore have a tapering profile, narrowing from the first end to the second end. Of course, these dimensions may be changed depending on the medicaments to be delivered from the blister strips 402a, 402b.

As will be appreciated, the first and second portions 585, 586 of the airstream 583 are produced concurrently in the manifold 550 as a result of patient inhalation at the mouthpiece 426.

Figure 17C:
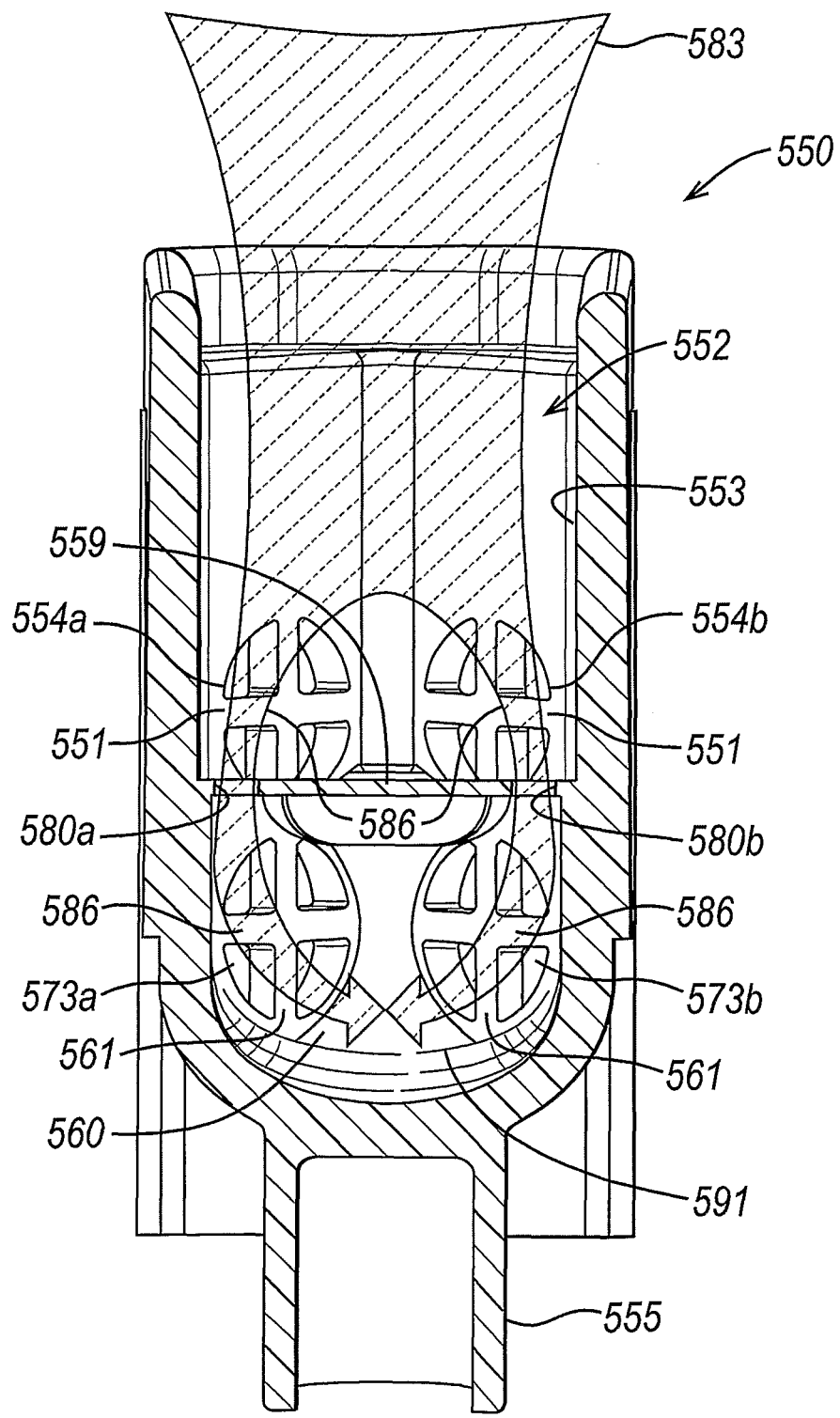

As will also be observed from FIG. 17c, the bleed holes 580a, 580b are configured and arranged so that the second portions 586 of the airstream 583 additionally flow around the boundary surface 591 of the chamber 560, forming a sheath-like air blanket adjacent the boundary surface 591. This helps alleviates deposition of the medicament powder on the boundary surface 591 as the powder is carried towards the mouthpiece 426.

It will be observed that the internal structure of the manifolds 450; 550 is such the longitudinal axis of the chimney 452; 552, which extends from the chimney inlet 453; 553 to the partition wall 459; 559, is perpendicular or generally perpendicular to the longitudinal axis of the chamber 460; 560, which extends from the chamber inlets 473a, b; 573a, b to the chamber exit 474; 574. Thus, the bleed portions 486; 586 of the inhalation airstream 483; 583 impact the first, medicament carrying portions 485; 585 in the chamber 460; 560 at right-angles thereto or generally at right-angles thereto.

It will also be observed that the manifolds 450; 550 require all airflow into the manifold to be via the chimney inlet 453; 553, which then acts such as to 'separate' that total airflow 483; 583 into the 'open blister directed' air portion 485; 585 (via the chimney exits 454a,b; 554a,b and the chamber inlets 473a,b; 573a,b) and a 'bleed' air portion 486; 586 (via the one or more bleed holes 480; 580a,b) to the chamber 460; 560. Good control over the amount of bleed air 486; 586 and, in particular, the percentage thereof (relative to the total airflow entering the manifold 450; 550 via the chimney inlet 453; 553) is therefore possible with a manifold having this arrangement. For the third medicament dispenser device, having a pair of medicament carriers 400a, 400b, the bleed air portion 486; 586 of the total airflow 483; 583 is ideally 80%, or substantially 80%, the balance passing through the opened pockets 404a, 404b.

It will be appreciated that there will likely be some air leakage into the manifolds 450; 550 upon patient inhalation at the mouthpiece 426, particularly via the chimney exits 454a, b; 554a,b and, perhaps more particularly, via the chimney inlets 473a,b; 573a,b, since the blister strips 402a, 402b will not form a complete sealing fit over these openings into the manifold 450; 550. Nonetheless, any such air leakage is negligible compared to the intended total inhalation airflow 483; 583 drawn into the manifold 450; 550 through the chimney inlet 453; 553 via the air inlet grille 470.

In the above-described embodiments, the manifolds 450; 550 are one-piece, injection moulded plastic components. More particularly, the manifolds 450; 550 are made from high density polyethylene (HDPE), since this material is suitable for injection moulding the manifold 450; 550, in particular high-speed injection moulding, while having a sufficiently low surface energy to minimise or inhibit deposition of the medicament powder thereon. However, other materials and manufacturing or moulding processes could be used. As other possible materials there may be mentioned fluoropolymers, for instance fluorinated ethylene-propylene (FEP), and other non-fluoropolymers, for instance polypropylene (PP).

It may be appreciated that any of the parts of the device or any component thereof which contacts medicament may be comprised of or coated with materials such as fluoropolymer materials (e.g. PTFE or FEP) that reduce the tendency of medicament to adhere thereto. Any movable parts may also have coatings applied thereto which enhance their desired movement characteristics. Frictional coatings may therefore be applied to enhance frictional contact and lubricants (e.g. silicone oil) used to reduce frictional contact as necessary.

In particular, the manifold itself may be wholly or partly comprised of or alternatively coated partially or wholly with materials that reduce the tendency of medicament to adhere thereto. Such materials may for example, lower the surface energy of the relevant manifold surface. Suitably, fluoropolymer materials are employed. High density polyethylene (HDPE) and/or modified acetal materials are also suitable.

Suitable fluoropolymer materials include those comprising multiples of one or more of the following monomeric units: tetrafluoroethylene (PTFE), fluorinated ethylene propylene (FEP), perfluoroalkoxyalkane (PFA), ethylene tetrafluoroethylene (ETFE), vinyldienefluoride (PVDF), and chlorinated ethylene tetrafluoroethylene. Fluorinated polymers, which have a relatively high ratio of fluorine to carbon, such as perfluorocarbon polymers, e.g., PTFE, PFA and FEP are particularly suitable. Particularly when used as a coating, the fluoropolymer is optionally blended with a non-fluorinated polymer such as polyamides, polyimides, polyamide imides, polyethersulfones, polyphenylene sulfides, and amine-formaldehyde thermosetting resins. These added polymers often improve adhesion of the polymer coating to the substrate. Preferred polymer blends are PTFE/FEP/polyamideimide, PTFE/polyether sulphone (PES) and FEP-benzoguanamine.

It will further be appreciated that the 'Summary of the invention' section discloses additional details, modifications or adaptations for the exemplary medicament dispenser devices, medicament carrier(s) and manifolds described with reference to the accompanying Figures.

Where not stated, the components of the medicament dispenser devices herein may be made from conventional engineering materials, especially conventional engineering plastics materials, more especially those which allow moulding of the component.

The manifold herein is suitable for use in a medicament dispenser device for dispensing powdered medicament formulations, particularly for the treatment of respiratory disorders such as asthma and chronic obstructive pulmonary disease (COPD), bronchitis and chest infections.

In particular, the manifold may be used in delivery of a medicament powder formulation based on one or more of the medicaments listed hereinbelow. Where the manifold is to be used with just a single blister pack, the medicament formulation in that pack may comprise just one of the listed medicaments (a monotherapy) or a plurality of the listed medicaments (combination therapy). Where the manifold is for use with plural (in particular two) blister packs, each pack may contain a medicament powder formulation comprising one or more of the listed medicaments, one pack containing at least one medicament not found in the or at least one of the other packs. Where the manifold is for use with two blister packs, the medicament powder formulation in one pack comprises a medicament not found in the other pack. Typically, each pack will have different medicament(s) than the other pack.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), salmefamol, carbuterol, mabuterol, etanterol, naminterol, clenbuterol, flerbuterol, bambuterol, indacaterol, formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino] ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); α$_4$ integrin inhibitors e.g. (2S)-3-[4-({[4-(aminocarbonyl)-1-piperidinyl] carbonyl}oxy)phenyl]-2-[((2S)-4-methyl-2-{[2-(2-methylphenoxy)acetyl]amino}pentanoyl)amino] propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

The formulated medicament product may in aspects, be a mono-therapy (i.e. single active medicament containing) product or it may be a combination therapy (i.e. plural active medicaments containing) product.

Suitable medicaments or medicament components of a combination therapy product are typically selected from the group consisting of anti-inflammatory agents (for example a corticosteroid or an NSAID), anticholinergic agents (for example, an $M_1$, $M_2$, $M_1/M_2$ or $M_3$ receptor antagonist), other β$_2$-adrenoreceptor agonists, antiinfective agents (e.g. an antibiotic or an antiviral), and antihistamines. All suitable combinations are envisaged.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1, 4-diene-17β-carbothioic acid S-(2-oxo-tetrahydro-furan-3S-yl)ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester, 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester and 9α, 21 dichloro-11β, 17α methyl-1,4 pregnadiene 3, 20 dione-17-[2'] furoate (mometasone furoate).

Further corticosteroids are described in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful in combination therapy through the manifold herein are disclosed WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398 and WO06/015870.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists), inhibitors of cytokine synthesis or 5-lipoxygenase inhibitors. Examples of iNOS inhibitors include those disclosed in WO93/13055, WO98/30537, WO02/50021, WO95/34534 and WO99/62875. Examples of CCR3 inhibitors include those disclosed in WO02/26722.

Suitable bronchodilators are β$_2$-adrenoreceptor agonists, including salmeterol (which may be a racemate or a single enantiomer, such as the R-enantiomer), for instance salmeterol xinafoate, salbutamol (which may be a racemate or a single enantiomer, such as the R-enantiomer), for instance salbutamol sulphate or as the free base, formoterol (which may be a racemate or a single diastereomer, such as the R,R-diastereomer), for instance formoterol fumarate or terbutaline and salts thereof. Other suitable β$_2$-adrenoreceptor agonists are 3-(4-{[6-({(2R)-2-hydroxy-2-[4-hydroxy-3-(hydroxymethyl)phenyl]ethyl}amino)hexyl]oxy}butyl)benzenesulfonamide, 3-(3-{[7-({(2R)-2-hydroxy-2-[4-hydroxy-3-hydroxymethyl)phenyl]ethyl}-amino)heptyl]oxy}propyl) benzenesulfonamide, 4-{(1R)-2-[(6-{2-[(2,6-dichlorobenzyl)oxy]ethoxy}hexyl)amino]-1-hydroxyethyl}-2-(hydroxymethyl)phenol, 4-{(1R)-2-[(6-{4-[3-(cyclopentylsulfonyl)phenyl]butoxy}hexyl)amino]-1-hydroxyethyl}-2-(hydroxymethyl)phenol, N-[2-hydroxyl-5-[(1R)-1-hydroxy-2-[[2-4-[[(2R)-2-hydroxy-2-phenylethyl] amino]phenyl]ethyl]amino]ethyl]phenyl]formamide, and N-2{2-[4-(3-phenyl-4-methoxyphenyl)aminophenyl]ethyl}-2-hydroxy-2-(8-hydroxy-2 (1H)-quinolinon-5-yl)ethylamine, and 5-[(R)-2-(2-{4-[4-(2-amino-2-methyl-propoxy)-phenylamino]-phenyl}-ethylamino)-1-hydroxy-ethyl]-8- hydroxy-1H-quinolin-2-one. Preferably, the β$_2$-adrenoreceptor agonist is a long acting β$_2$-adrenoreceptor agonist (LABA), for example a compound which provides effective bronchodilation for about 12 hours or longer.

Other β$_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO 01/42193 and WO 03/042160.

Suitable phosphodiesterase 4 (PDE4) inhibitors include compounds that are known to inhibit the PDE4 enzyme or which are discovered to act as a PDE4 inhibitor, and which are only PDE4 inhibitors, not compounds which inhibit other members of the PDE family as well as PDE4. Generally it is preferred to use a PDE4 inhibitor which has an IC$_{50}$ ratio of about 0.1 or greater as regards the IC$_{50}$ for the PDE4 catalytic form which binds rolipram with a high affinity divided by the IC$_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining IC$_{50}$s ratios is set out in U.S. Pat. No. 5,998,428 which is incorporated herein in full by reference as though set out herein. See also PCT application WO 00/51599 for an another description of said assay.

Suitable PDE4 inhibitors include those compounds that have a salutary therapeutic ratio, i.e., compounds which preferentially inhibit cAMP catalytic activity where the enzyme is in the form that binds rolipram with a low affinity, thereby reducing the side effects that apparently are linked to inhibiting the form that binds rolipram with a high affinity. Another way to state this is that the preferred compounds will have an IC$_{50}$ ratio of about 0.1 or greater as regards the IC$_{50}$ for the PDE4 catalytic form that binds rolipram with a high affinity divided by the IC$_{50}$ for the form that binds rolipram with a low affinity.

A further refinement of this standard is that of one wherein the PDE4 inhibitor has an IC$_{50}$ ratio of about 0.1 or greater; said ratio is the ratio of the IC$_{50}$ value for competing with the binding of 1 nM of [$^3$H]R-rolipram to a form of PDE4 which binds rolipram with a high affinity over the IC$_{50}$ value for inhibiting the PDE4 catalytic activity of a form which binds rolipram with a low affinity using 1 μM[$^3$H]-cAMP as the substrate.

Most suitable are those PDE4 inhibitors which have an IC$_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylicacid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an IC$_{50}$ ratio of 0.1 or greater.

Other suitable medicament compounds include: cis-4-cyano-4-[3-(cyclopentyloxy)-4-methoxyphenyl]cyclohexane-1-carboxylic acid (also known as cilomalast) disclosed in U.S. Pat. No. 5,552,438 and its salts, esters, pro-drugs or physical forms; AWD-12-281 from elbion (Hofgen, N. et al. 15th EFMC Int Symp Med Chem (Sep. 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3, 4,4a,10b-hexahydro-8-methoxy-2-methylbenzo[c][1,6] naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/um565 from Vernalis; or T-440 (Tanabe Seiyaku; Fuji, K. et al. J Pharmacol Exp Ther, 1998, 284(1): 162), and T2585.

Further compounds are disclosed in WO04/024728, WO04/056823 and WO04/103998, all of Glaxo Group Limited.

Suitable anticholinergic agents are those compounds that act as antagonists at the muscarinic receptor, in particular those compounds, which are antagonists of the M$_1$ or M$_3$ receptors, dual antagonists of the M$_1$/M$_3$ or M$_2$/M$_3$, receptors or pan-antagonists of the M$_1$/M$_2$/M$_3$ receptors. Exemplary compounds include the alkaloids of the belladonna plants as illustrated by the likes of atropine, scopolamine, homatropine, hyoscyamine; these compounds are normally administered as a salt, being tertiary amines.

Other suitable anti-cholinergics are muscarinic antagonists, such as (3-endo)-3-(2,2-di-2-thienylethenyl)-8,8-dimethyl-8-azoniabicyclo[3.2.1]octane iodide, (3-endo)-3-(2-cyano-2,2-diphenylethyl)-8,8-dimethyl-8-azoniabicyclo [3.2.1]octane bromide, 4-[hydroxy(diphenyl)methyl]-1-{2-[(phenylmethyl)oxy]ethyl}-1-azonia bicyclo[2.2.2]octane bromide, (1R,5S)-3-(2-cyano-2,2-diphenylethyl)-8-methyl-8-{2-[(phenylmethyl)oxy]ethyl}-8-azoniabicyclo[3.2.1]octane bromide, (endo)-3-(2-methoxy-2,2-di-thiophen-2-yl-ethyl)-8,8-dimethyl-8-azonia-bicyclo[3.2.1]octane iodide, (endo)-3-(2-cyano-2,2-diphenyl-ethyl)-8,8-dimethyl-8-azonia-bicyclo[3.2.1]octane iodide, (endo)-3-(2-carbamoyl-2,2-diphenyl-ethyl)-8,8-dimethyl-8-azonia-bicyclo[3.2.1]octane iodide, (endo)-3-(2-cyano-2,2-di-thiophen-2-yl-ethyl)-8,8-dimethyl-8-azonia-bicyclo[3.2.1]octane iodide, and (endo)-3-{2,2-diphenyl-3-[(1-phenyl-methanoyl)-amino]-propyl}-8,8-dimethyl-8-azonia-bicyclo[3.2.1]octane bromide.

Particularly suitable anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118. Also of interest are revatropate (for example, as the hydrobromide, CAS 262586-79-8) and LAS-34273 which is disclosed in WO01/04118, darifenacin (CAS 133099-04-4, or CAS 133099-07-7 for the hydrobromide sold under the name Enablex), oxybutynin (CAS 5633-

20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other anticholinergic agents include compounds disclosed in U.S. Ser. Nos. 60/487,981 and 60/511,009.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine.

Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine.

Exemplary H1 antagonists are as follows:
Ethanolamines: carbinoxamine maleate, clemastine fumarate, diphenylhydramine hydrochloride, and dimenhydrinate.
Ethylenediamines: pyrilamine amleate, tripelennamine HCl, and tripelennamine citrate.
Alkylamines: chiropheniramine and its salts such as the maleate salt, and acrivastine.
Piperazines: hydroxyzine HCl, hydroxyzine pamoate, cyclizine HCl, cyclizine lactate, meclizine HCl, and cetirizine HCl.
Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

The medicament, or one of the medicaments, may be an H3 antagonist (and/or inverse agonist). Examples of H3 antagonists include, for example, those compounds disclosed in WO2004/035556 and in WO2006/045416.

Other histamine receptor antagonists which may be used include antagonists (and/or inverse agonists) of the H4 receptor, for example, the compounds disclosed in Jablonowski et al., *J. Med. Chem.* 46:3957-3960 (2003).

In respect of combination products, co-formulation compatibility is generally determined on an experimental basis by known methods and may depend on chosen type of medicament dispenser device action.

The medicament components of a combination product are suitably selected from the group consisting of anti-inflammatory agents (for example a corticosteroid or an NSAID), anti-cholinergic agents (for example, an $M_1$, $M_2$, $M_1/M_2$ or $M_3$ receptor antagonist), other $\beta_2$-adrenoreceptor agonists, anti-infective agents (e.g. an antibiotic or an antiviral), and antihistamines. All suitable combinations are envisaged.

Suitably, the co-formulation compatible components comprise a $\beta_2$-adrenoreceptor agonist and a corticosteroid; and the co-formulation incompatible component comprises a PDE-4 inhibitor, an anti-cholinergic or a mixture thereof. The $\beta_2$-adrenoreceptoragonists may for example be salbutamol (e.g., as the free base or the sulphate salt) or salmeterol (e.g., as the xinafoate salt) or formoterol (eg as the fumarate salt). The corticosteroid may for example, be a beclomethasone ester (e.g., the dipropionate) or a fluticasone ester (e.g., the propionate) or budesonide.

In one example, the co-formulation compatible components comprise fluticasone propionate and salmeterol, or a salt thereof (particularly the xinafoate salt) and the co-formulation incompatible component comprises a PDE-4 inhibitor, an anti-cholinergic (e.g. ipratropium bromide or tiotropium bromide) or a mixture thereof.

In another example, the co-formulation compatible components comprise budesonide and formoterol (e.g. as the fumarate salt) and the co-formulation incompatible component comprises a PDE-4 inhibitor, an anti-cholinergic (e.g. ipratropium bromide or tiotropium bromide) or a mixture thereof.

Generally, powdered medicament particles suitable for delivery to the bronchial or alveolar region of the lung have an aerodynamic diameter of less than 10 micrometers, preferably from 1-6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

The medicament dispenser device described herein is in one aspect suitable for dispensing medicament for the treatment of respiratory disorders such as disorders of the lungs and bronchial tracts including asthma and chronic obstructive pulmonary disorder (COPD). In another aspect, the invention is suitable for dispensing medicament for the treatment of a condition requiring treatment by the systemic circulation of medicament, for example migraine, diabetes, pain relief e.g. inhaled morphine.

Accordingly, there is provided the use of the medicament dispenser device herein for the treatment of a respiratory disorder, such as asthma and COPD. Alternatively, the present invention provides a method of treating a respiratory disorder such as, for example, asthma and COPD, which comprises administration by inhalation of an effective amount of medicament product as herein described from a medicament dispenser device herein.

The amount of any particular medicament compound or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The medicaments for treatment of respiratory disorders herein may for example, be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1.5 mg per day.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A manifold for use in a medicament dispenser device for the delivery of medicament powder from an open blister pocket of each of plural blister packs, the manifold comprising
   a body,
   said body defining a chimney having only a single chimney inlet and plural chimney exits for directing airflow from said chimney inlet to said chimney exits;
   the body further defining a chamber having plural chamber inlets and a chamber exit,
   wherein the chimney exits and chamber inlets are arranged to form plural pairings of chimney exit and chamber inlet, each said pairing in use associated with an open blister pocket of a different one of said plural blister packs;
   wherein the chimney exit and chamber inlet of the plural pairings lie side-by-side each other such that when said open blister pocket of the associated blister packs are positioned adjacent thereto said airflow is directed from chimney exit to chamber inlet via the associated open blister pockets to entrain said medicament powder and enable transport thereof in the airflow from the chamber inlet to said chamber exit, and wherein one or more bleed holes are provided between the chimney and the chamber such that bleed airflow is able to be directed into the chamber to disruptively impact the airflow that transports the entrained medicament powder.

2. The manifold according to claim 1, wherein the manifold is arranged such that in use, from 3 to 50% of the total airflow entering the manifold through the chimney inlet is directed via plural chimney exit towards an open blister pocket and from 50% to 97% of the total airflow is directed through the one or more bleed holes into the chamber.

3. The manifold according to claim 2, wherein the manifold is arranged such that in use, from 5 to 25% of the total airflow entering the manifold through the chimney inlet is directed via plural chimney exit towards an open blister pocket and from 95 to 75% of the total airflow is directed through the one or more bleed holes into the chamber.

4. The manifold according to claim 1, wherein the manifold provides an airflow resistance of from 1 to 5 kPa for a total airflow entering the manifold through the chimney inlet at a rate of 60 liters/minute.

5. The manifold according to claim 1, wherein at least one chimney exit defines an essentially circular profile.

6. The manifold according to claim 1 wherein at least one chimney exit is provided with a cross-piece spanning it.

7. The manifold according to claim 6, wherein said cross-piece is cruciform in shape.

8. The manifold according to claim 1, wherein the chimney and the chamber are positioned side-by-side each other.

9. The manifold according to claim 1, wherein the chimney and the chamber are positioned one on top of each other.

10. The manifold according to claim 1, wherein the chimney and the chamber share a common wall and at least one of the one or more bleed holes are provided to said common wall.

11. The manifold according to claim 10, wherein all of the one or more bleed holes are provided to said common wall.

12. The manifold according to claim 1, wherein the one or more bleed holes have a total cross-sectional area of from 1 to 35 $mm^2$.

13. The manifold according to claim 1, wherein the one or more bleed holes define a profile selected from the group consisting of ovular, circular, D-shaped and elongate slot profiles.

14. The manifold according to claim 13, wherein the one or more bleed holes define an elongate slot profile and each has a length of from 1 to 20 mm and a width of from 0.5 to 3 mm.

15. The manifold according to claim 1, comprising two elongate slot form bleed holes arranged parallel to each other.

16. The manifold according to claim 1, wherein the one or more bleed holes are spaced from the chimney exit.

17. The manifold according to claim 16, wherein the spacing of the one or more bleed holes from the chamber inlet amounts to at least 10% of the length of the chamber measured from the chamber inlet to the chamber exit.

18. The manifold according to claim 1, wherein at least one of the one or more bleed holes is directed towards an inner wall of the chamber.

19. The manifold according to claim 1, wherein the manifold is made from high-density polyethylene.

20. The manifold according to claim 1, wherein the manifold is wholly or partly comprised of and/or coated with a fluoropolymer material.

21. The manifold according to claim 20, wherein said fluoropolymer material comprises multiples of one or more monomeric units selected from the group consisting of tetrafluoroethylene (PTFE), fluorinated ethylene propylene (FEP), perfluoroalkoxyalkane (PFA), ethylene tetrafluoroethylene (ETFE), vinyldienefluoride (PVDF), chlorinated ethylene tetrafluoroethylene and any mixtures thereof.

22. The manifold according to claim 1, wherein the chimney and the chamber are oriented generally perpendicularly to each other.

23. The manifold according to claim 1, wherein the airflow (entraining airflow) and the bleed airflow are respective airflow portions of an inhalation airflow which is drawn into the manifold through the chimney inlet when an inhalation force is applied at the chamber exit.

24. The manifold according to claim 1 adapted such that on application of an inhalation force at the chamber exit, the bleed airflow is greater than the entraining airflow.

25. The manifold according to claim 1, wherein the only air entry points into the chamber are the one or more chamber inlet(s), the one or more bleed holes and the chamber exit.

26. The manifold according to claim 1, wherein the only air entry points into the chimney are the chimney inlet, the one or more bleed holes and the one or more chimney exits.

27. The manifold according to claim 1 which is a one-piece article.

28. The manifold according to claim 1 which is a moulded article.

29. A sub-assembly comprising a manifold according to claim 1 and a mouthpiece fitted thereto to be in communication with the chamber exit such that inhalation at the mouthpiece directs airflow into the manifold through the chimney inlet.

30. The assembly according to claim 29, wherein the mouthpiece is releasably fitted to the manifold.

31. The assembly according to claim 29 wherein the manifold and mouthpiece are in snap-fit engagement.

32. A medicament dispenser device, comprising a manifold according to claim 1, the medicament dispenser device suitable for the delivery of medicament powder from at least one blister pack having at least one blister pocket.

33. The medicament dispenser device according to claim 32 additionally comprising a mouthpiece provided to said manifold.

34. The medicament dispenser device according to claim 33, wherein the manifold locates within a housing at a position intermediate between said mouthpiece and a station for presenting an open blister pocket of said at least one blister pack thereto.

35. The medicament dispenser device according to claim 32, further comprising a housing and, within said housing, a mechanism for opening the or each blister pocket of the at least one blister pack and presenting the or each opened blister pocket to the chimney exit(s) and chamber inlet(s).

36. The medicament dispenser device according to claim 32, wherein said mechanism comprises an indexer for indexing the blister pockets, one at a time, to the manifold.

37. The medicament dispenser device according to claim 36 for use with at least one blister pack in the form of an elongate strip and having multiple distinct pockets for containing distinct medicament doses, wherein said pockets are spaced in series along the length of the strip.

38. The medicament dispenser device according to claim 32, wherein the dispenser device is suitable for the simultaneous delivery of medicament powder from an open blister pocket of each of plural blister packs.

39. The medicament dispenser device according to claim 32 comprising at least one blister pack containing medicament in powder form.

40. The medicament dispenser device according to claim 39, wherein said at least one blister pack comprises plural medicament powder-containing blisters.

41. The medicament dispenser device according to claim 39 wherein said at least one blister pack comprises plural medicament powder containing blisters arranged in series fashion on an elongate strip-form blister pack.

42. The medicament dispenser device according to claim 41, wherein said elongate strip-form blister pack comprises
(a) a base sheet in which blisters are formed to define pockets therein, each containing medicament powder;
(b) a lid sheet which is sealed to the base sheet except in the region of the blisters and mechanically peelable from the base sheet to enable release of said medicament powder.

43. The medicament dispenser device according to claim 39, comprising a blister pack, wherein the medicament powder contained therein comprises both a bronchodilator and an anti-inflammatory as active medicament components thereof.

44. The medicament dispenser device according to claim 39, comprising first and second blister packs, wherein the medicament powder contained in said first blister pack comprises a bronchodilator as the active medicament component and the medicament powder contained in said second blister pack comprises an anti-inflammatory as the active medicament component.

45. The medicament dispenser device according to claim 43, wherein said bronchodilator is a beta-agonist and said anti-inflammatory is a corticosteroid.

46. The medicament dispenser device according to claim 41, wherein the at least one blister pack has a portion which is adapted in use to be separated lengthways from the at least one blister pack to open the blisters.

47. The medicament dispenser device according to claim 46, wherein the separable portion is a first portion of the at least one blister pack and the at least one blister pack further has a second portion from which the first portion is separable, the blisters being defined between the first and second portions.

48. The medicament dispenser device according to claim 47, wherein the second portion is formed with a series of recesses along its length in which the medicament powder is contained and the first portion provides a lid for each of the recesses.

49. The medicament dispenser device according to claim 46, wherein the separable portion has first and second ends which are spaced lengthways from one another and the separable portion is separable from the at least one blister pack by drawing the first end lengthways along the at least one blister pack towards the second end.

50. The medicament dispenser device according to claim 39 comprising first and second blister packs, each pack having at least one pocket each containing an inhalable medicament powder, wherein the at least one pocket of the first pack contains at least one medicament which is not in the at least one pocket of the second pack.

51. The medicament dispenser device according to claim 50, wherein the inhalable medicament powder in each pack is for treatment of respiratory disease.

52. The manifold according to claim 5, wherein essentially circular profile has a diameter of from 1 to 7 mm.

53. The manifold according to claim 12, wherein the one or more bleed holes have a cross-sectional area of from 10 to 30 $mm^2$.

54. The manifold according to claim 14, wherein the one or more bleed holes each has a length of from 3 to 10 mm and a width of from 0.7 to 2 mm.

55. The manifold according to claim 17, wherein the spacing of the one or more bleed holes from the chamber inlet amounts to at least 20% of the length of the chamber measured from the chamber inlet to the chamber exit.

56. The manifold according to claim 54, wherein the spacing of the one or more bleed holes from the chamber inlet amounts to at least 30% of the length of the chamber measured from the chamber inlet to the chamber exit.

57. The manifold according to claim 1 wherein the chamber has only a single chamber exit.

58. The manifold according to claim 1 wherein manifold comprises a pair of curved walls for receiving the open blister pocket of each of the plural blister packs.

59. The manifold according to claim 58 wherein each curved wall defines one of the plural pairings of chimney exit and chamber inlet.

60. The manifold according to claim 15, wherein the elongate slots have a tapering profile, narrowing from a first end nearest the chamber exit to a second end nearest the chimney exits.

61. The manifold according to claim 60 wherein the bleed holes are configured and arranged so that, in use, the second portion of the airstream additionally flow around the boundary surface of the chamber forming a sheath-like blanket adjacent the boundary surface.

* * * * *